(12) United States Patent
Smith et al.

(10) Patent No.: US 9,155,451 B2
(45) Date of Patent: *Oct. 13, 2015

(54) VARIABLY FLEXIBLE INSERTION DEVICE AND METHOD FOR VARIABLY FLEXING AN INSERTION DEVICE

(71) Applicant: Syntheon, LLC, Miami, FL (US)

(72) Inventors: Kevin W. Smith, Coral Gables, FL (US); Derek Dee Deville, Coral Gables, FL (US); Korey Kline, Miami, FL (US); Matthew A. Palmer, Miami, FL (US)

(73) Assignee: Syntheon, LLC, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/021,266

(22) Filed: Sep. 9, 2013

(65) Prior Publication Data

US 2014/0012085 A1   Jan. 9, 2014

Related U.S. Application Data

(63) Continuation-in-part of application No. 11/367,607, filed on Mar. 2, 2006, now Pat. No. 8,092,374, and a continuation-in-part of application No. 11/502,322, filed on Aug. 10, 2006, now Pat. No. 7,988,621, and a (Continued)

(51) Int. Cl.
*A61B 1/005* (2006.01)
*A61B 1/00* (2006.01)
(Continued)

(52) U.S. Cl.
CPC ............... *A61B 1/0051* (2013.01); *A61B 1/005* (2013.01); *A61B 1/0055* (2013.01);
(Continued)

(58) Field of Classification Search
CPC ...... A61B 1/0055; A61B 1/31; A61B 1/0051; A61B 1/00135; A61B 1/018; A61B 1/01; A61B 1/005; A61B 1/00078; A61B 17/3417; A61B 17/3421; A61B 17/00318; A61B 17/00323; A61B 17/00336; A61B 17/345; A61B 1/045; A61B 1/0052; A61B 1/00154; A61M 29/00
USPC .......... 606/108, 191; 600/585, 201, 139, 114, 600/144, 149, 118, 121, 123–125, 184, 146, 600/115, 141, 138, 140; 604/523–528, 604/95.04, 95.01, 97.01, 98.01, 104, 171, 604/173, 176
See application file for complete search history.

(56) References Cited

U.S. PATENT DOCUMENTS 3,557,780 A    1/1971  Sato
3,998,216 A    12/1976 Hosono
(Continued)

FOREIGN PATENT DOCUMENTS

WO    2005048814 A2    6/2005

OTHER PUBLICATIONS

International Search Report for PCT/US07/012179 dated Sep. 12, 2008.
(Continued)

*Primary Examiner* — Jocelin Tanner
(74) *Attorney, Agent, or Firm* — Mayback & Hoffman, P.A.; Gregory L. Mayback; Rebecca A. Tie

(57) ABSTRACT

A torque-transmitting, variably-flexible device, comprising a hollow body having a proximal end and a distal end, a torque-transmitting element operable to transmit torque from the proximal end towards the distal end of the hollow body, and a steering element operable to steer the distal end of the hollow body.

15 Claims, 72 Drawing Sheets

Related U.S. Application Data continuation-in-part of application No. 11/804,843, filed on May 21, 2007, now Pat. No. 8,556,804, and a continuation-in-part of application No. 11/823,247, filed on Jun. 27, 2007, and a continuation-in-part of application No. 12/432,351, filed on Apr. 29, 2009, now Pat. No. 7,914,445, and a continuation-in-part of application No. 13/006,745, filed on Jan. 14, 2011, now Pat. No. 8,292,802, and a continuation-in-part of application No. 13/006,760, filed on Jan. 14, 2011, now Pat. No. 8,298,137, and a continuation-in-part of application No. 13/311,145, filed on Dec. 5, 2011, now Pat. No. 8,696,639, and a continuation-in-part of application No. 13/622,240, filed on Sep. 18, 2012, now Pat. No. 8,708,894.

(51) Int. Cl.
    *A61M 29/00*     (2006.01)
    *A61B 17/34*     (2006.01)
    *A61B 17/00*     (2006.01)
    *A61B 17/29*     (2006.01)

(52) U.S. Cl.
    CPC ........ *A61B 1/00078* (2013.01); *A61B 1/00135* (2013.01); *A61B 1/00154* (2013.01); *A61M 29/00* (2013.01); *A61B 17/3421* (2013.01); *A61B 2017/003* (2013.01); *A61B 2017/00318* (2013.01); *A61B 2017/2929* (2013.01); *A61B 2017/345* (2013.01)

(56) References Cited

U.S. PATENT DOCUMENTS

| | | | |
|---|---|---|---|
| 4,176,662 A | 12/1979 | Frazer | |
| 4,575,185 A | 3/1986 | Wentzell et al. | |
| 4,753,223 A | 6/1988 | Bremer | |
| 4,762,118 A | 8/1988 | Lia | |
| 4,815,450 A | 3/1989 | Patel | |
| 4,817,613 A | 4/1989 | Jaraczewski | |
| 4,838,859 A | 6/1989 | Strassmann | |
| 4,890,602 A | 1/1990 | Hake | |
| 4,893,613 A | 1/1990 | Hake | |
| 4,998,282 A | 3/1991 | Shishido et al. | |
| 5,211,633 A | 5/1993 | Stouder, Jr. | |
| D337,733 S | 7/1993 | Ewing et al. | |
| 5,259,366 A | 11/1993 | Reydel et al. | |
| 5,337,733 A * | 8/1994 | Bauerfeind et al. | 600/139 |
| 5,386,817 A | 2/1995 | Jones | |
| 5,577,992 A | 11/1996 | Chiba et al. | |
| 5,759,151 A | 6/1998 | Sturges | |
| 5,807,237 A | 9/1998 | Tindel | |
| 5,873,816 A | 2/1999 | Kagawa et al. | |
| 6,117,068 A | 9/2000 | Gourley | |
| 6,196,967 B1 | 3/2001 | Lim | |
| 6,346,077 B1 | 2/2002 | Taylor | |
| 6,375,654 B1 | 4/2002 | McIntyre | |
| 6,387,044 B1 | 5/2002 | Tachibana | |
| 6,468,203 B2 | 10/2002 | Belson | |
| 6,478,731 B2 | 11/2002 | Speier | |
| 6,506,150 B1 | 1/2003 | Ouchi | |
| 6,517,477 B1 | 2/2003 | Wendlandt | |
| 6,610,007 B2 | 8/2003 | Belson et al. | |
| 6,645,223 B2 | 11/2003 | Boyle et al. | |
| 6,800,056 B2 | 10/2004 | Tartaglia et al. | |
| 6,802,809 B2 | 10/2004 | Okada | |
| 6,858,005 B2 | 2/2005 | Ohline et al. | |
| 6,942,613 B2 | 9/2005 | Ewers et al. | |
| 6,974,411 B2 | 12/2005 | Belson | |
| 6,984,203 B2 * | 1/2006 | Tartaglia et al. | 600/114 |
| 7,066,880 B2 | 6/2006 | Wendlandt | |
| 7,104,951 B2 | 9/2006 | Hasegawa et al. | |
| 7,435,214 B2 | 10/2008 | Kucklick | |
| 7,811,228 B2 | 10/2010 | Adams | |
| 8,556,804 B2 * | 10/2013 | Smith et al. | 600/139 |
| 2002/0002323 A1 | 1/2002 | Moriyama | |
| 2002/0082585 A1 * | 6/2002 | Carroll et al. | 604/528 |
| 2002/0177750 A1 | 11/2002 | Pilvisto | |
| 2003/0135198 A1 | 7/2003 | Berhow et al. | |
| 2004/0044350 A1 * | 3/2004 | Martin et al. | 606/139 |
| 2004/0138529 A1 | 7/2004 | Wiltshire et al. | |
| 2004/0182393 A1 | 9/2004 | MacMillan | |
| 2004/0186350 A1 | 9/2004 | Brenneman et al. | |
| 2005/0075538 A1 | 4/2005 | Banik et al. | |
| 2005/0131279 A1 | 6/2005 | Boulais | |
| 2005/0165275 A1 * | 7/2005 | Von Felten et al. | 600/140 |
| 2006/0025652 A1 | 2/2006 | Vargas | |
| 2006/0069346 A1 | 3/2006 | Smith et al. | |
| 2007/0088367 A1 | 4/2007 | Von Weymarn-Scharli | |
| 2007/0179339 A1 | 8/2007 | Gorini et al. | |
| 2007/0208300 A1 | 9/2007 | Pravong et al. | |
| 2007/0270648 A1 | 11/2007 | Smith | |
| 2008/0091170 A1 | 4/2008 | Vargas et al. | |
| 2009/0149710 A1 | 6/2009 | Stefanchik | |

OTHER PUBLICATIONS

International Search Report for PCT/US07/05478 dated Dec. 17, 2007.
International Search Report for PCT/US07/075701 dated Aug. 29, 2008.
International Search Report for PCT/US08/064084 dated Dec. 9, 2008.
International Search Report for PCT/US/068348 dated Oct. 30, 2008.
ASGE Abstract 136: "A Split Overtube for Easier Colonoscopy" dated May 4, 2009 (author not named).

* cited by examiner

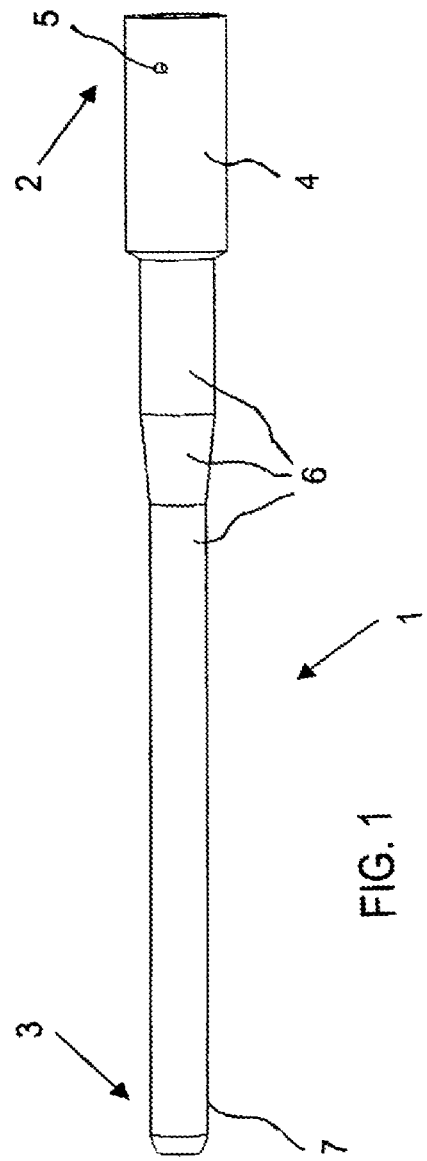
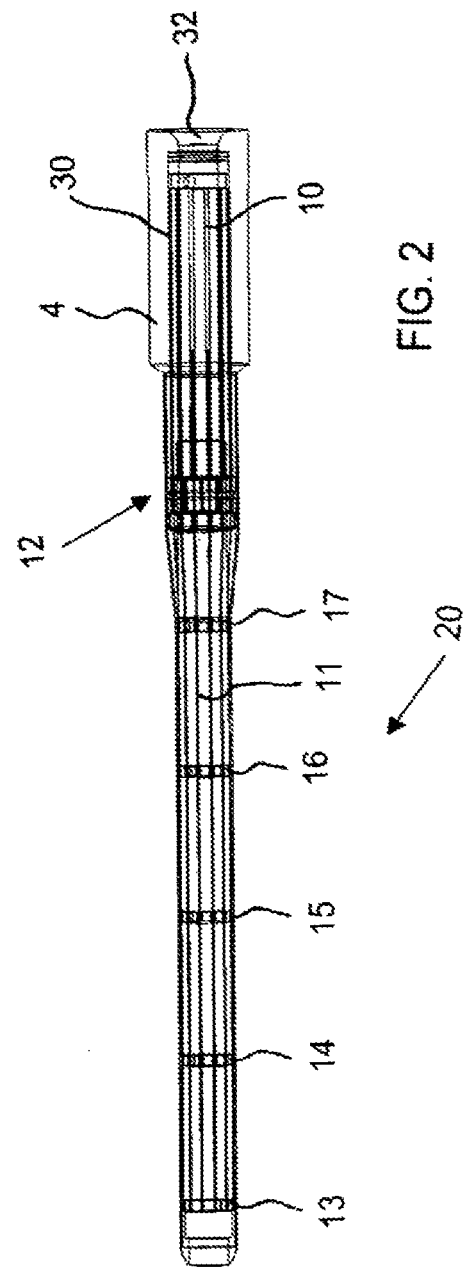
FIG. 1
FIG. 2

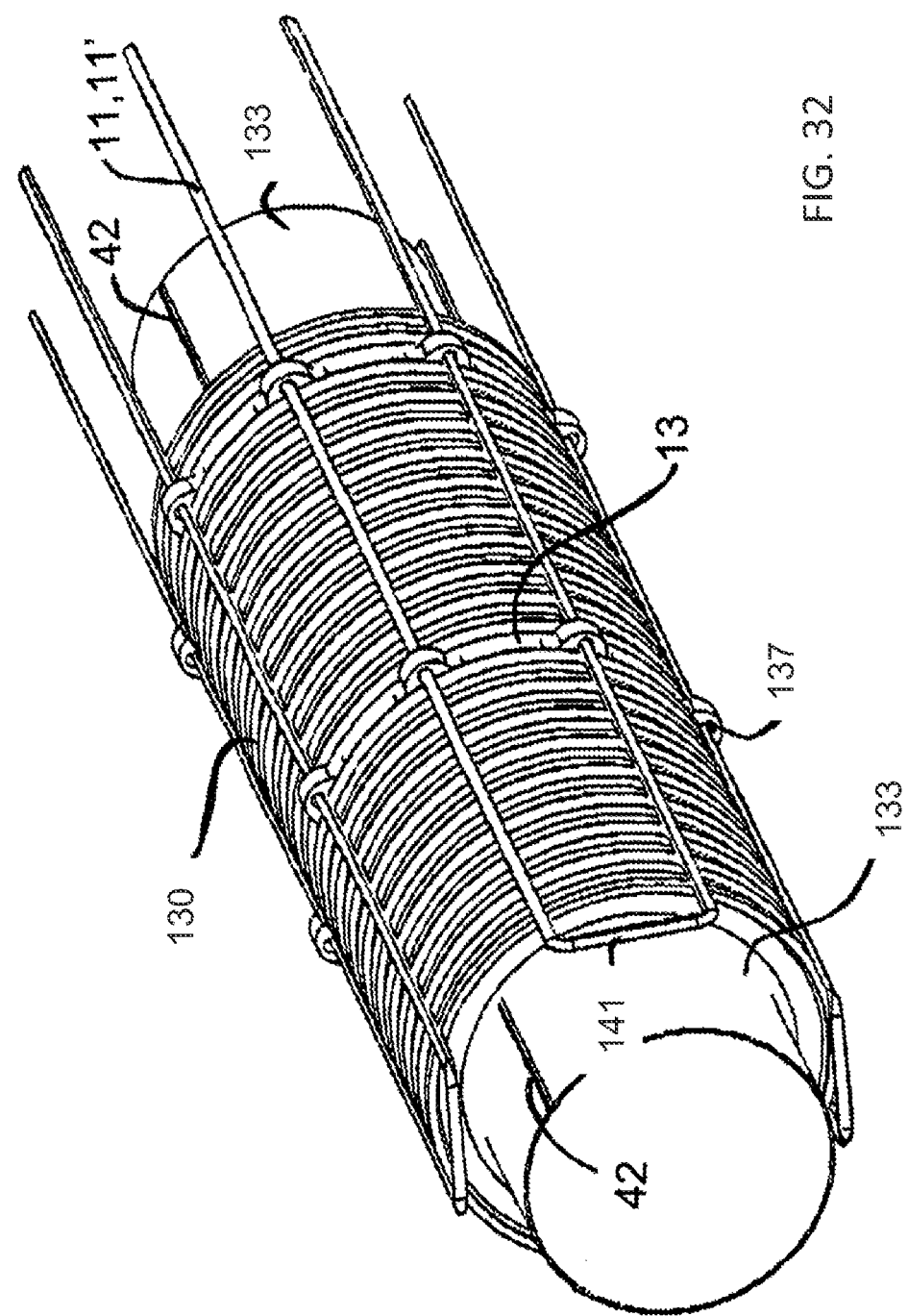

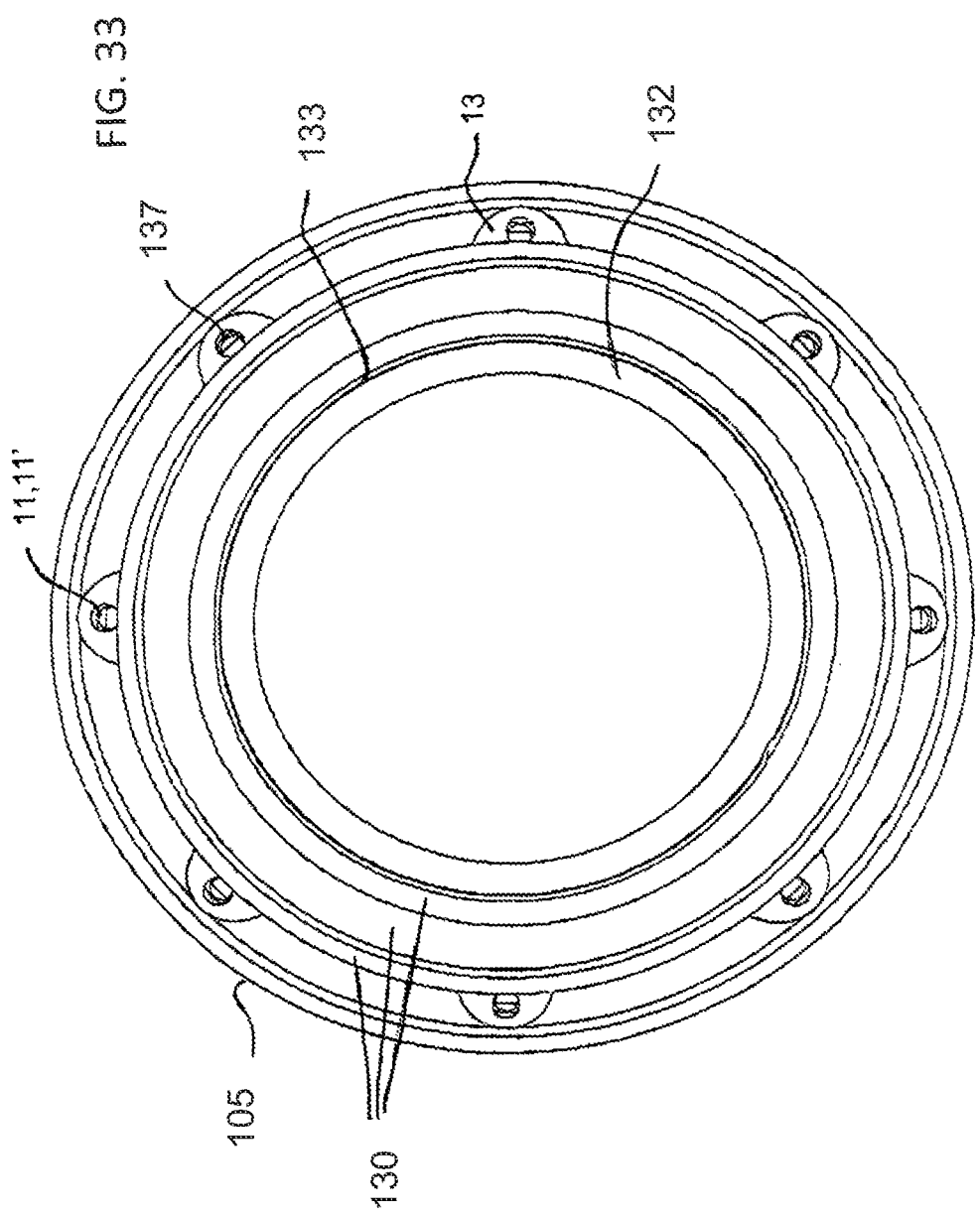

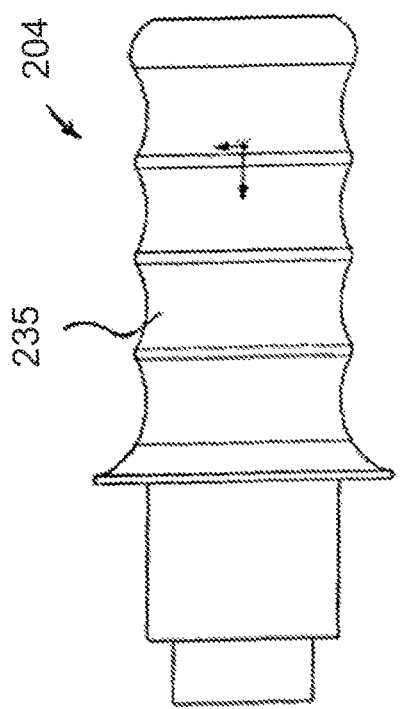
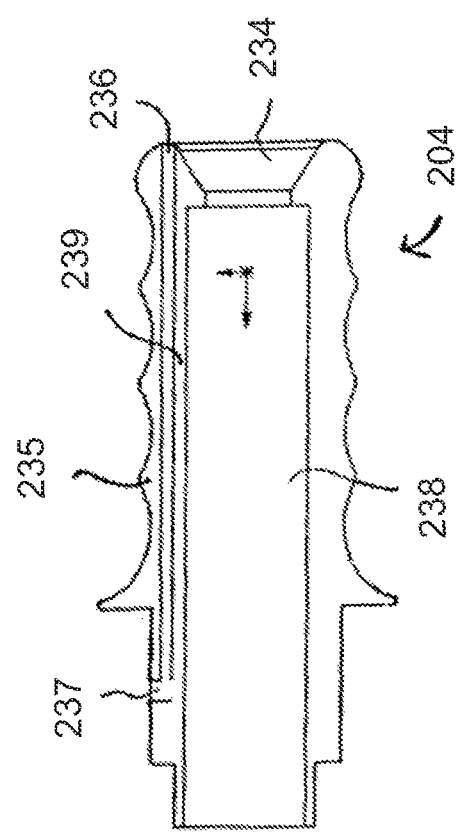

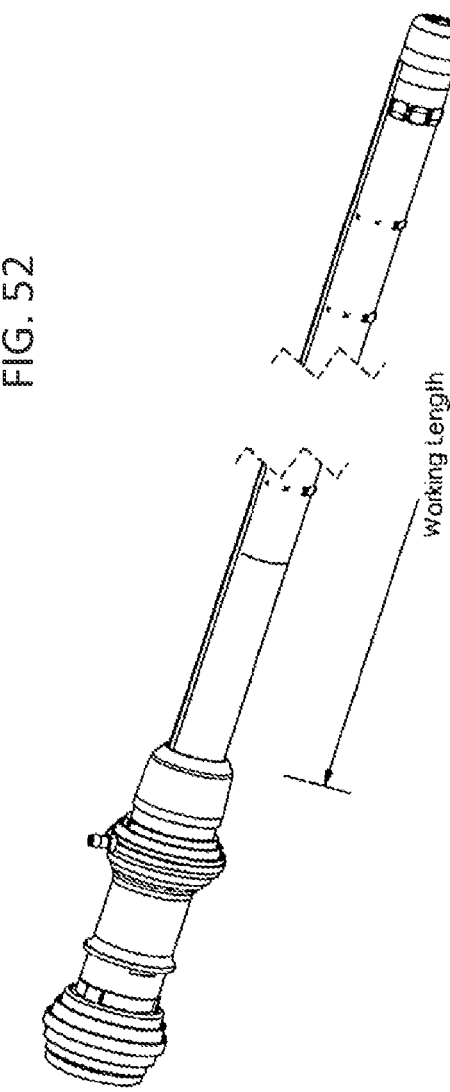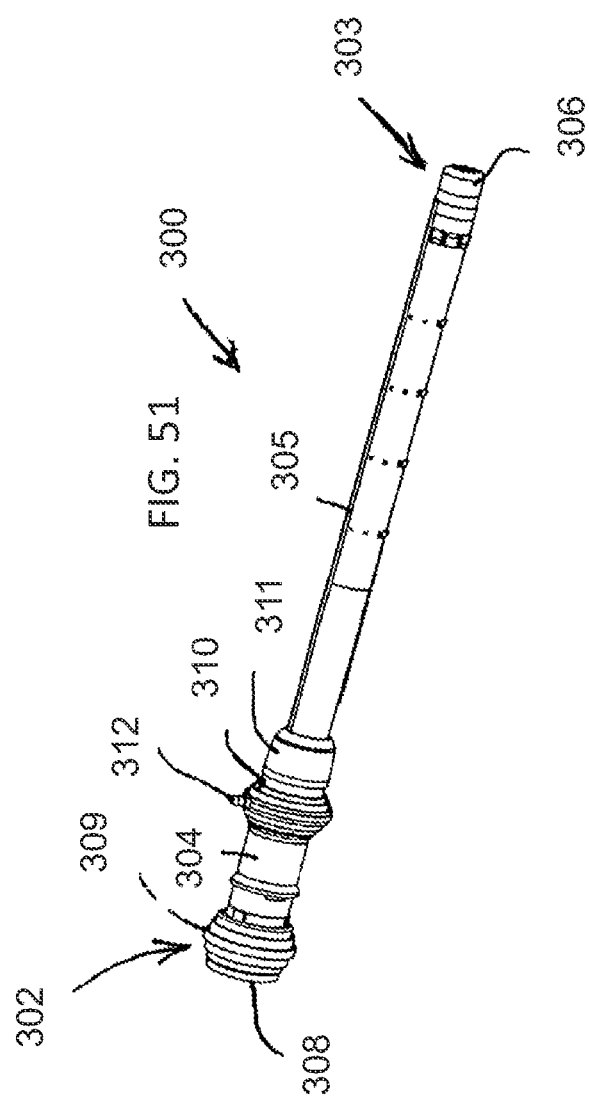

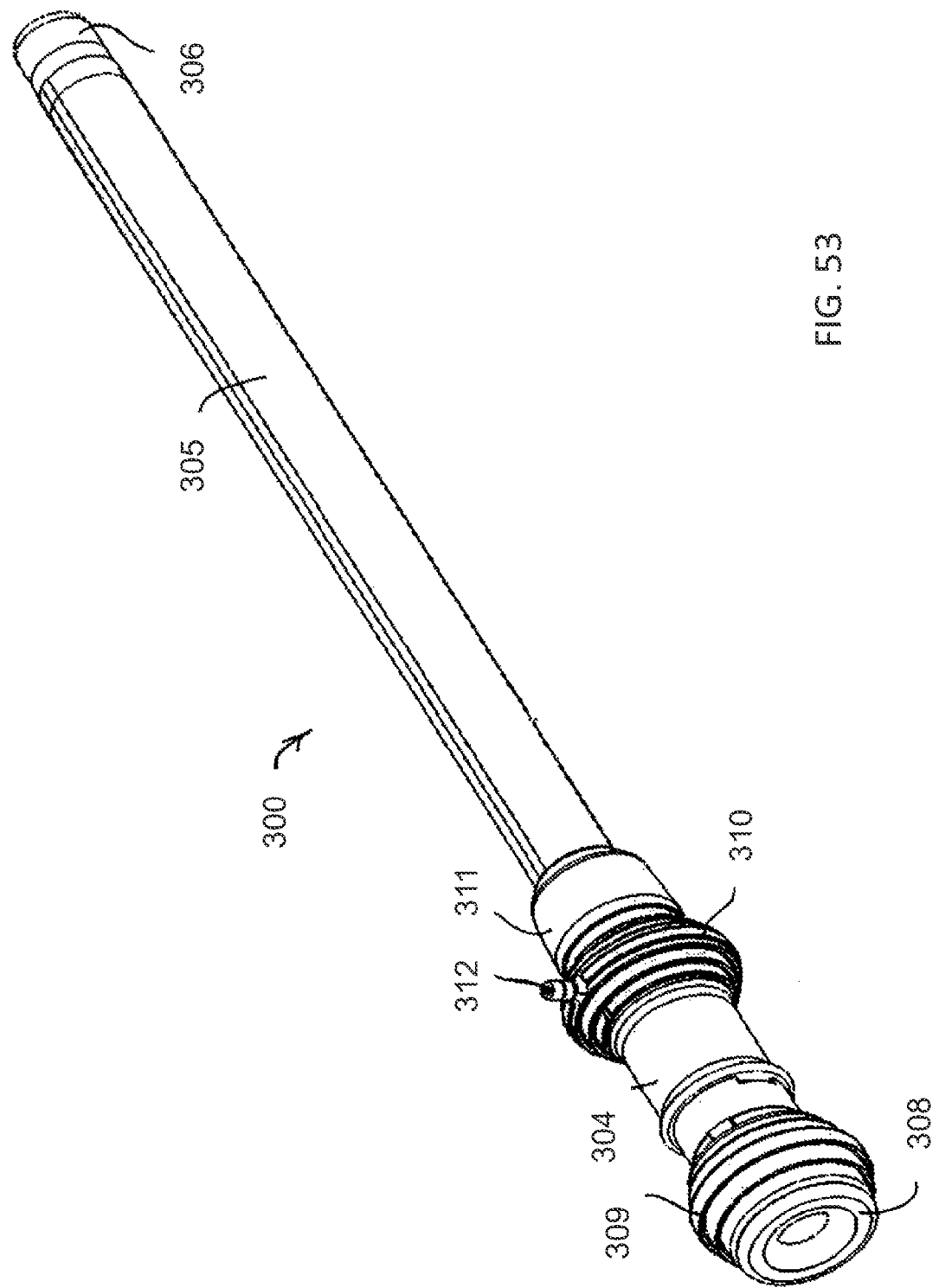

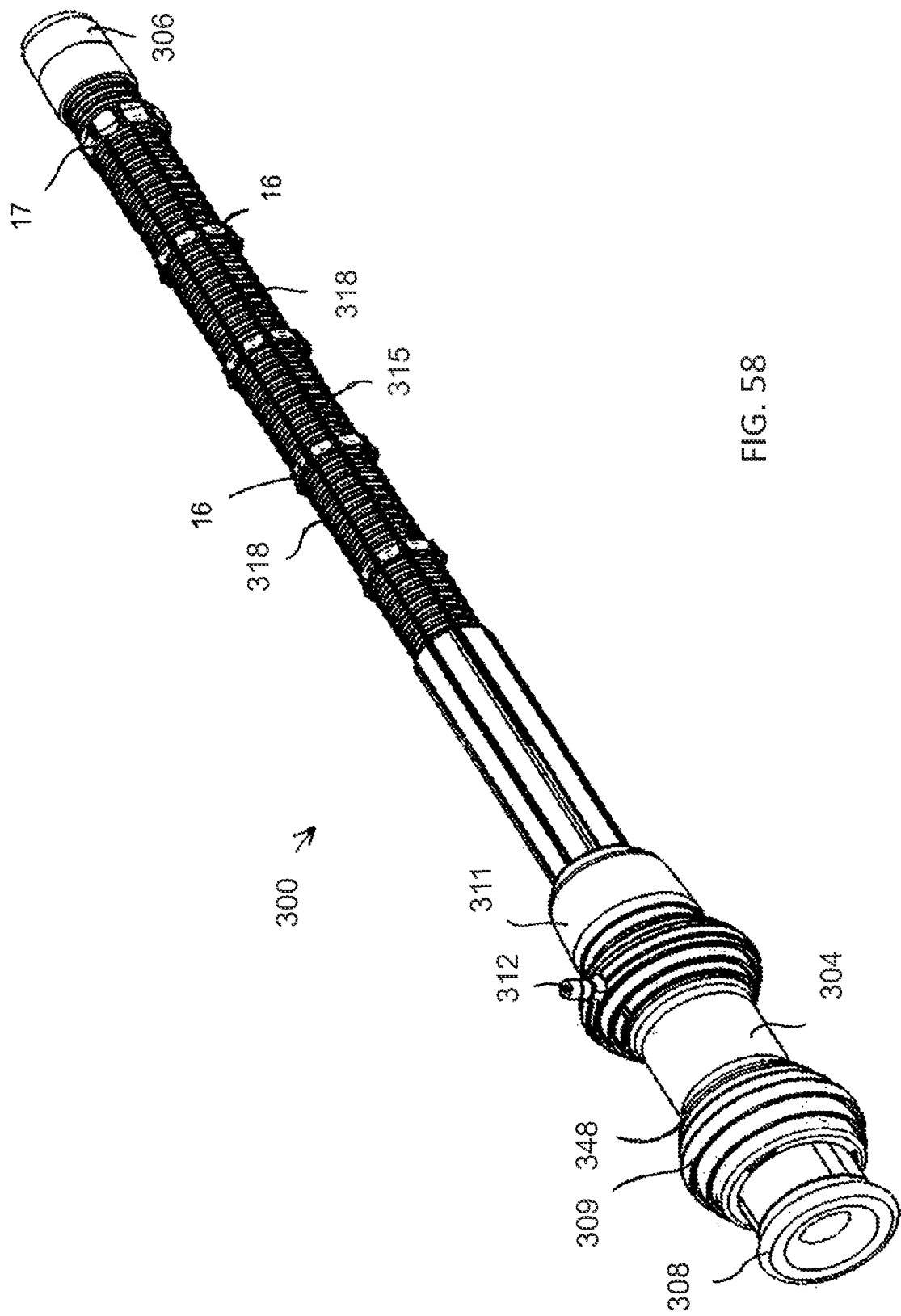

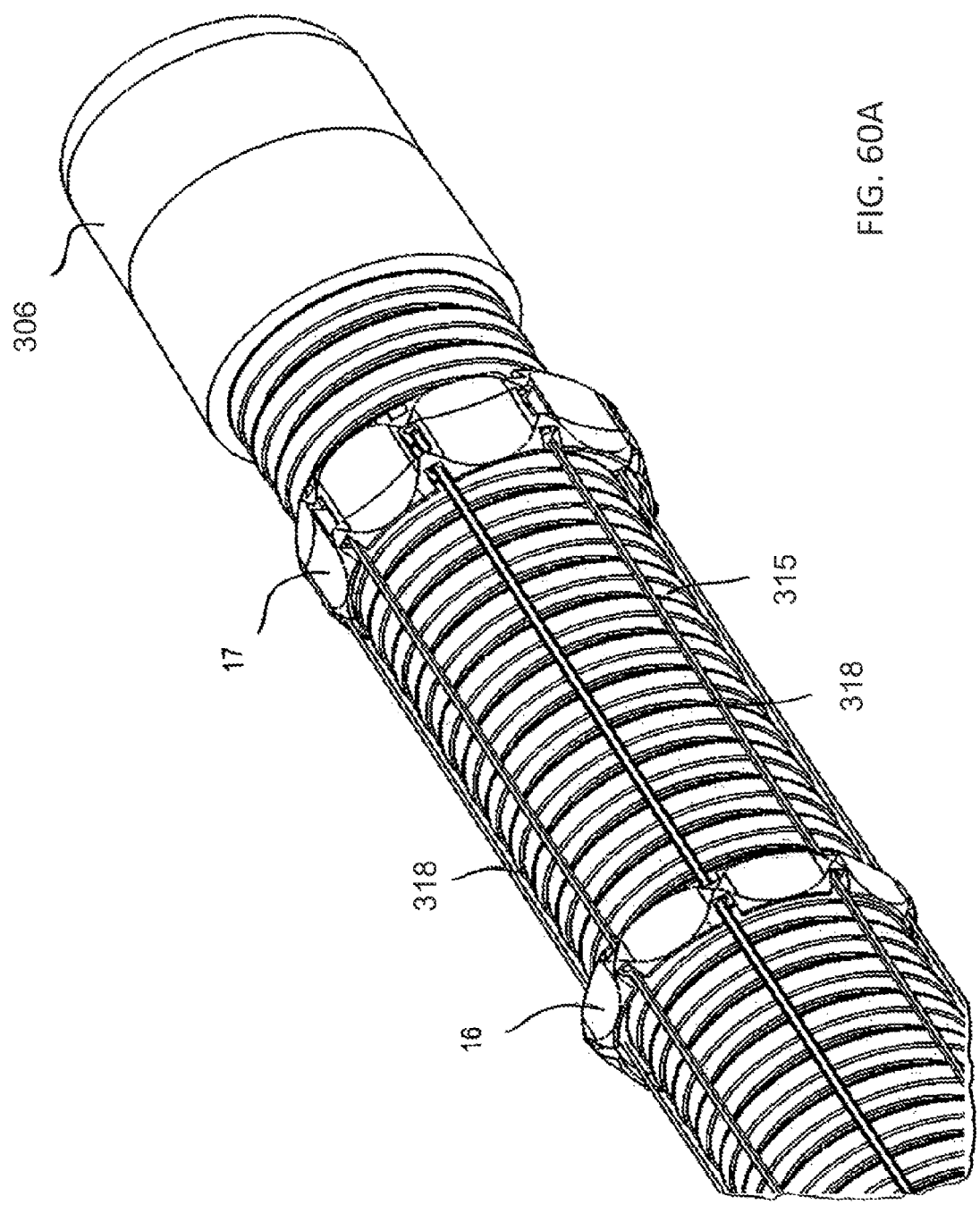

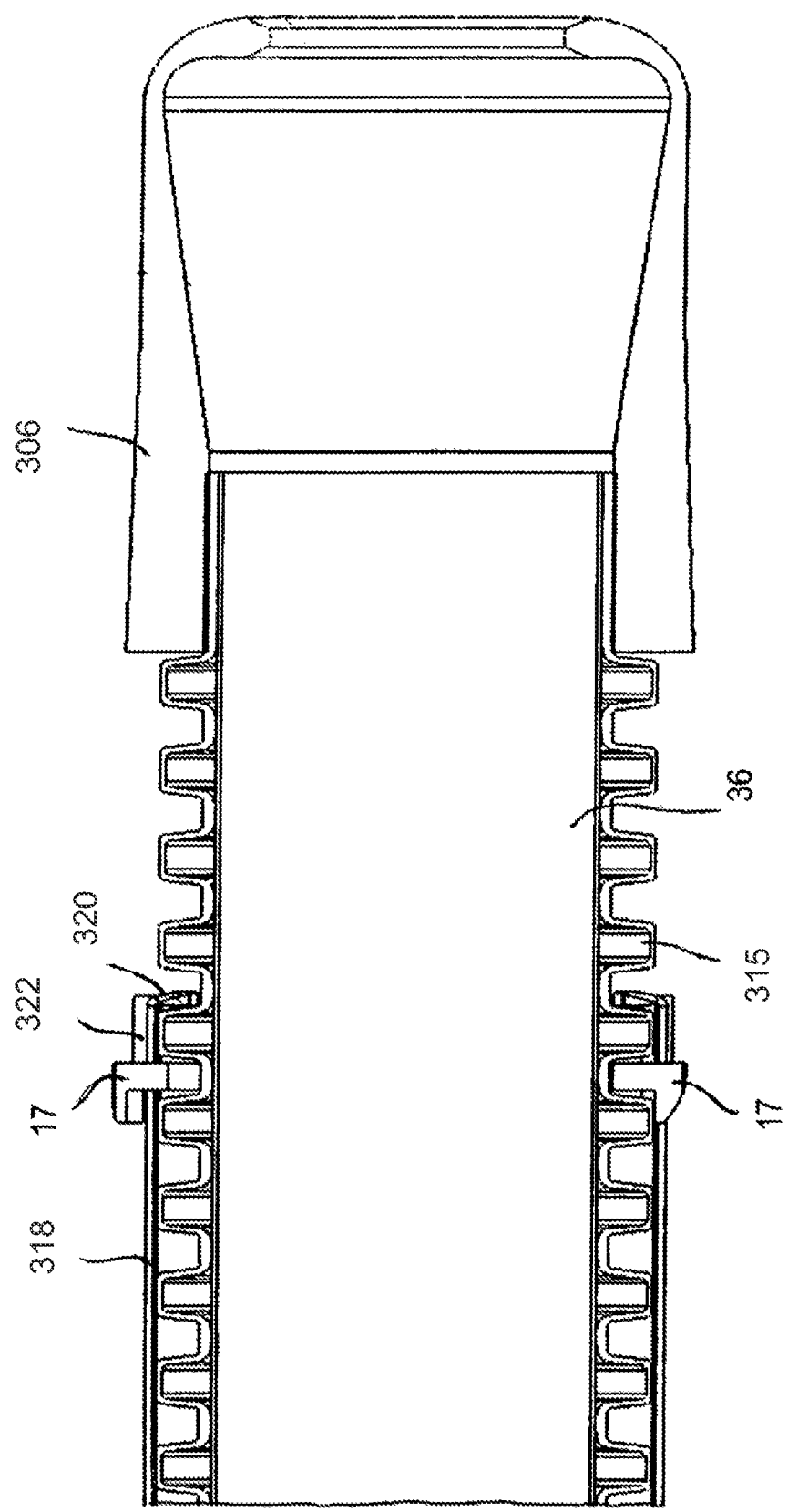

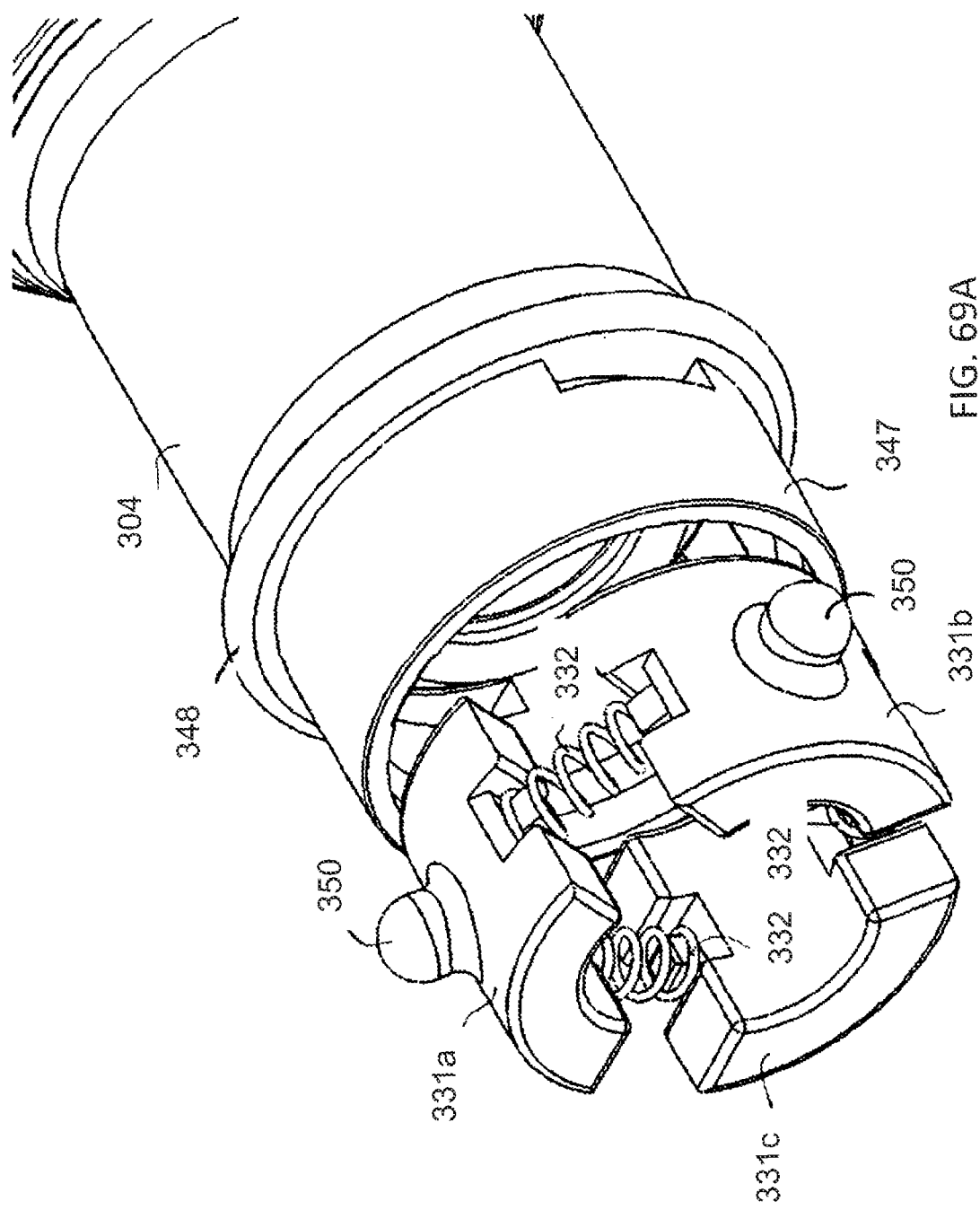

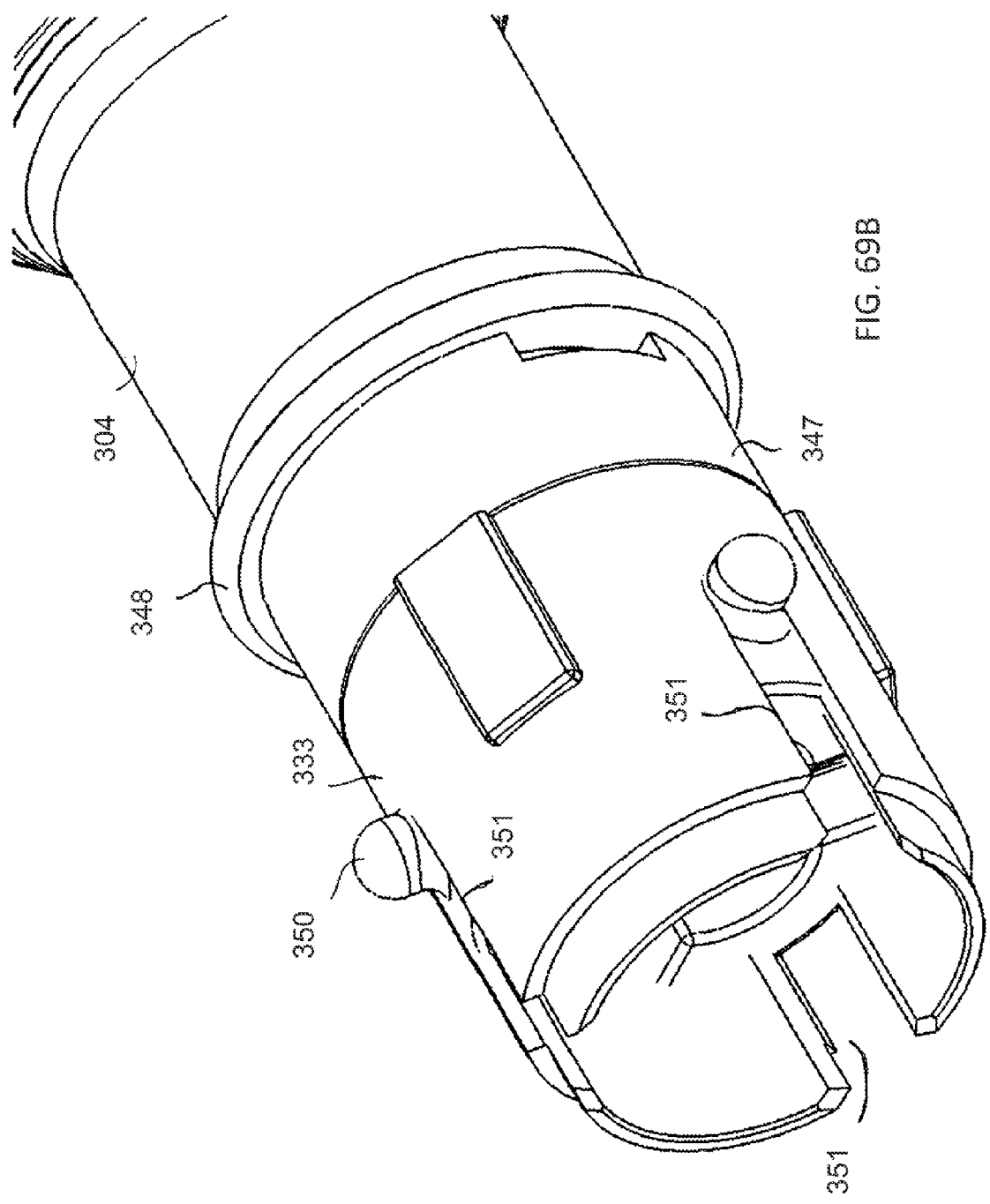

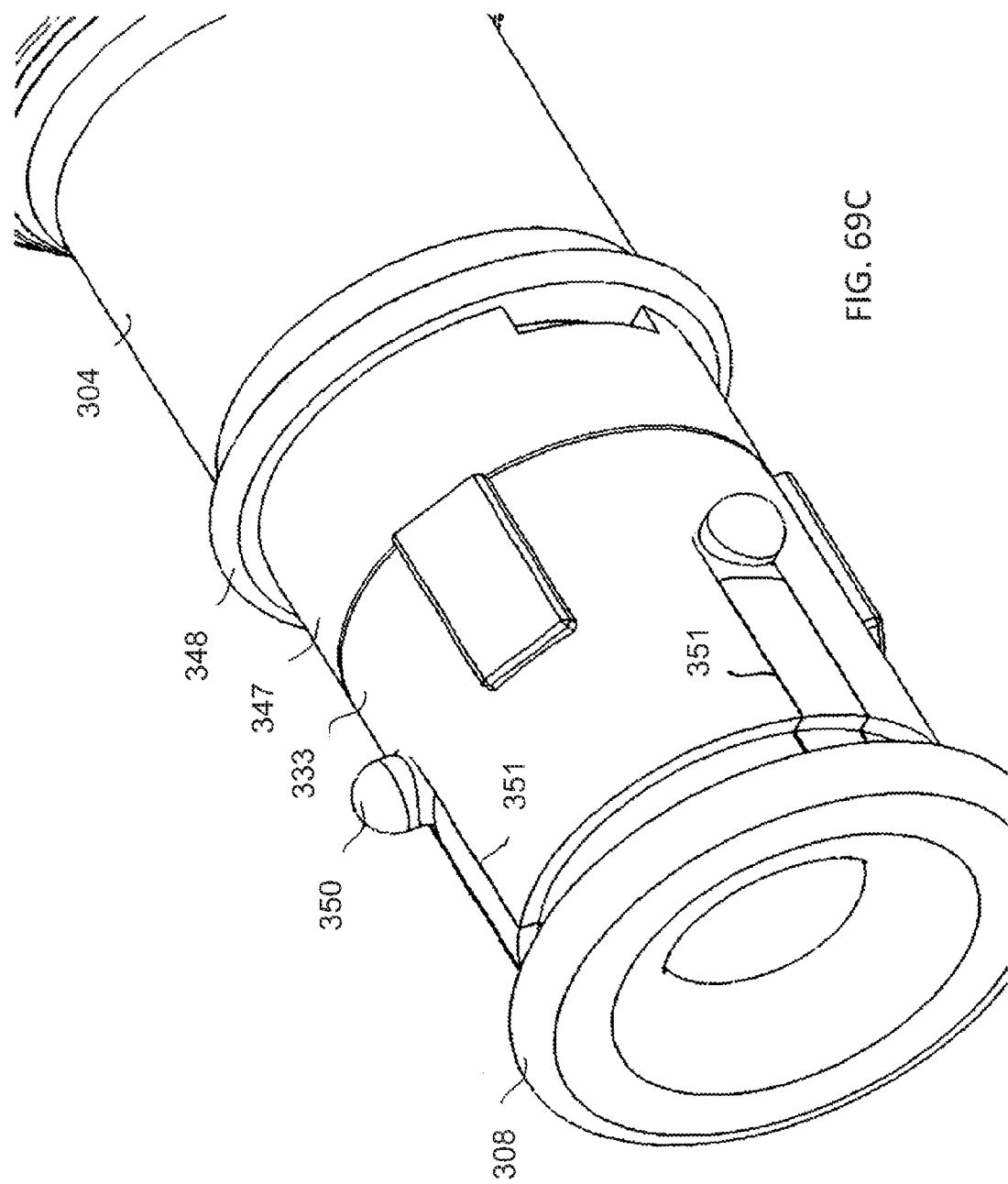

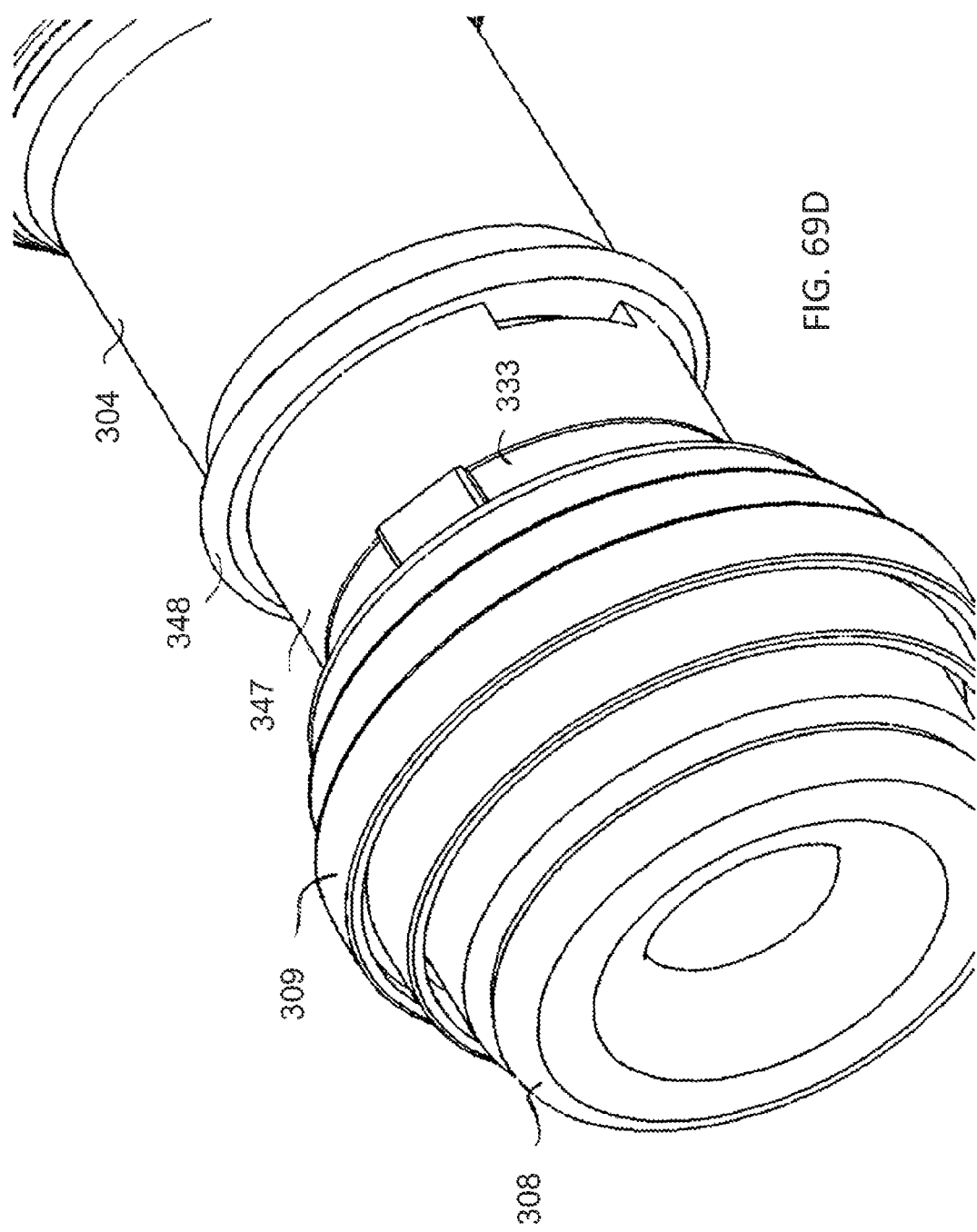

VARIABLY FLEXIBLE INSERTION DEVICE AND METHOD FOR VARIABLY FLEXING AN INSERTION DEVICE

CROSS-REFERENCE TO RELATED APPLICATIONS

This application is a continuation-in-part of U.S. Patent Application Nos.:
Ser. No. 11/367,607, filed on Mar. 2, 2006, now U.S. Pat. No. 8,092,374;
Ser. No. 11/502,322, filed on Aug. 10, 2006, now U.S. Pat. No. 7,988,621;
Ser. No. 11/804,843, filed on May 21, 2007;
Ser. No. 11/823,247, filed on Jun. 27, 2007;
Ser. No. 12/432,351, filed on Apr. 29, 2009, now U.S. Pat. No. 7,914,445;
Ser. No. 13/006,745, filed on Jan. 14, 2011, now U.S. Pat. No. 8,292,802;
Ser. No. 13/006,760, filed on Jan. 14, 2011, now U.S. Pat. No. 8,298,137;
Ser. No. 13/311,145, filed on Dec. 5, 2011; and
Ser. No. 13/622,240, filed on Sep. 18, 2012,
the entire disclosures of which are all hereby incorporated herein by reference in their entireties.

STATEMENT REGARDING FEDERALLY SPONSORED RESEARCH OR DEVELOPMENT

Not applicable.

FIELD OF INVENTION

The invention relates to a variably flexible insertion device and to a method for variably flexing an insertion device. The invention also relates to a method for transmitting torque and variably flexing a corrugated insertion device. The invention further relates to a torque-transmitting, variably-flexible, locking insertion device. The insertion device may be used to insert an instrument, in particular a scope, such as an endoscope or a colonoscope, into a patient.

BACKGROUND OF THE INVENTION

Insertion devices for surgical instruments are known in the art. Prior art insertion devices of this general type have been quite complicated, cumbersome and difficult to use. Such devices have a relatively large diameter, a limited maximum length, a limited transmission of torque and present obstacles to insertion of instruments. For example, a disadvantage of such variably flexing insertion devices is that the device twists when applying torque to the proximal end and therefore the torque is not transmitted along the device toward the distal end. This makes it difficult or impossible to impart a circumferential movement along the device when needed to traverse the body.

In addition, prior art devices of this general type cannot be connected to an instrument, such as an endoscope or a colonoscope, in such a manner as to be reliable and sufficiently torque-transmitting, while at the same time being easily releasable therefrom and variably flexible. The operator of the device must have the ability to manipulate the instrument when necessary with the insertion device and yet free the instrument easily when necessary.

SUMMARY OF THE INVENTION

It is accordingly an object of the invention to provide a variably flexible insertion device and a method for variably flexing an insertion device, and to provide a torque-transmitting, corrugated insertion device and method for transmitting torque and variably flexing a corrugated insertion device, which overcome the hereinafore-mentioned disadvantages of the heretofore-known devices and methods of this general type, and which are simpler (e.g., to construct), have more varied uses, have a smaller diameter, a greater torque transmission, may be made longer and allow smooth insertion of an instrument, and are more reliable than the prior art. It is another object of the invention to provide a simple yet effective measure for steering the insertion device. It is further object of the invention to provide a torque-transmitting, variably-flexible, locking insertion device and a method for operating the insertion device, which permit an operator of the device to easily and reliably lock the insertion device to and unlock the insertion device from an instrument while varying stiffness.

With the foregoing and other objects in view, there is provided, in accordance with the invention, a torque-transmitting, variably-flexible device, comprising a hollow body having a proximal end and a distal end, a torque-transmitting element operable to transmit torque from the proximal end towards the distal end of the hollow body, and a steering element operable to steer the distal end of the hollow body.

In accordance with another feature, the proximal end of the hollow body has an entrance for receiving an instrument and the distal end of the hollow body has a tip for protrusion of the instrument.

In accordance with a further feature, the torque-transmitting element is a torque braid.

In accordance with an added feature, the hollow body has a given length and the torque braid is disposed within the hollow body and extends substantially entirely over the given length.

In accordance with an additional feature, the steering element is comprised of tendons disposed within the hollow body, wherein at least some of the tendons are individually adjustable in length for steering the distal end of the hollow body.

In accordance with yet a further feature, the device further comprises vertebrae disposed within the hollow body for guiding the tendons.

In accordance with yet an added feature, some of the vertebrae have channels formed therein that permit movement of some of the tendons.

In accordance with yet an additional feature, the device further comprises a transitioning device operable to selectively transition the hollow body between a relatively flexible condition and a relatively stiff condition.

In accordance with again another feature, the transitioning device is a vacuum-activated device operable to apply suction to the hollow body to place the hollow body in the relatively stiff condition.

In accordance with again a further feature, the device further comprises tendons disposed within the hollow body, wherein suction applied by the vacuum-activated device frictionally locks the tendons in place to selectively maintain the hollow body in the relatively stiff condition.

In accordance with again an added feature, the tendons are not under tension in both the relatively flexible and relatively stiff conditions.

In accordance with again an additional feature, the tendons vary in number along the hollow body for providing zones of varying stiffness.

In accordance with yet another added feature, the number of tendons is greater toward the distal end than toward the proximal end for increasing stiffness at the distal end.

In accordance with yet another further feature, the hollow body of the device has an outer jacket and an inner sleeve defining a space therebetween, the tendons are at least partly disposed in the space, and the vacuum-activated device applies suction to the space for frictionally locking the tendons in place.

In accordance with yet another additional feature, the device further comprises a coil disposed within the hollow body, the coil tending to maintain the hollow body with an approximately round cross section and in a straight condition when in the relatively flexible condition.

In accordance with an added feature, the vacuum-activated device is a vacuum connection communicating with the space.

In accordance with a further feature, the hollow body has a handle at the proximal end, the handle has an outer handle and an inner handle defining a vacuum plenum volume therebetween communicating with the space, and the handle has a vacuum port communicating with the vacuum plenum volume.

Other features that are considered as characteristic for the invention are set forth in the appended claims.

Although the invention is illustrated and described herein as embodied in a torque-transmitting, variably flexible insertion device and a method for variably flexing an insertion device, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

Advantages of embodiments of the present invention will be apparent from the following detailed description of the preferred embodiments thereof, which description should be considered in conjunction with the accompanying drawings in which:

FIG. 1 is a diagrammatic, side-elevational view of an exemplary embodiment of a variably flexible insertion device according to the invention;

FIG. 2 is a view similar to FIG. 1 showing details of the interior of the insertion device of the embodiment of FIG. 1;

FIG. 32 is a view of the insertion device similar to FIGS. 30 and 31, in which the tip and a termination bushing have been removed;

FIG. 33 is a cross-sectional view of the insertion device, which is taken along a line IVX-IVX of FIG. 30, in the direction of the arrows;

FIG. 42 is an elevational view of an ergonomically constructed valve handle to be used with the insertion device of the embodiment of FIG. 36;

FIG. 43 is a longitudinal-sectional view of the handle of FIG. 42;

FIG. 51 is a diagrammatic, perspective view of a torque-transmitting, variably-flexible, locking insertion device according to another exemplary embodiment of the invention;

FIG. 52 is a perspective view similar to FIG. 51, showing a working length of the insertion device;

FIG. 53 is an enlarged, perspective view of the insertion device of the embodiment of FIG. 51, showing details of a proximal end;

FIG. 58 is a view similar to FIG. 56, of the insertion device with a lock in an actuated condition;

FIGS. 60A and 60B are fragmentary, perspective views of the distal end of the insertion device in which the locking ring is respectively shown and omitted for clarity and in which the outer jacket has been removed;

FIGS. 61A, 61B and 61C are fragmentary, longitudinal-sectional views of the distal end of the insertion device with the outer jacket removed and respectively showing two locking rings, one locking ring and no locking ring;

FIGS. 69A, 69B, 69C and 69D are enlarged, fragmentary, perspective views of the proximal end of the insertion device respectively showing a handle with a clamping plate, a body tube slid over the clamping plate, an end cap at the proximal end and a bobbin distally of the end cap.

DETAILED DESCRIPTION OF THE INVENTION

Figure 3:
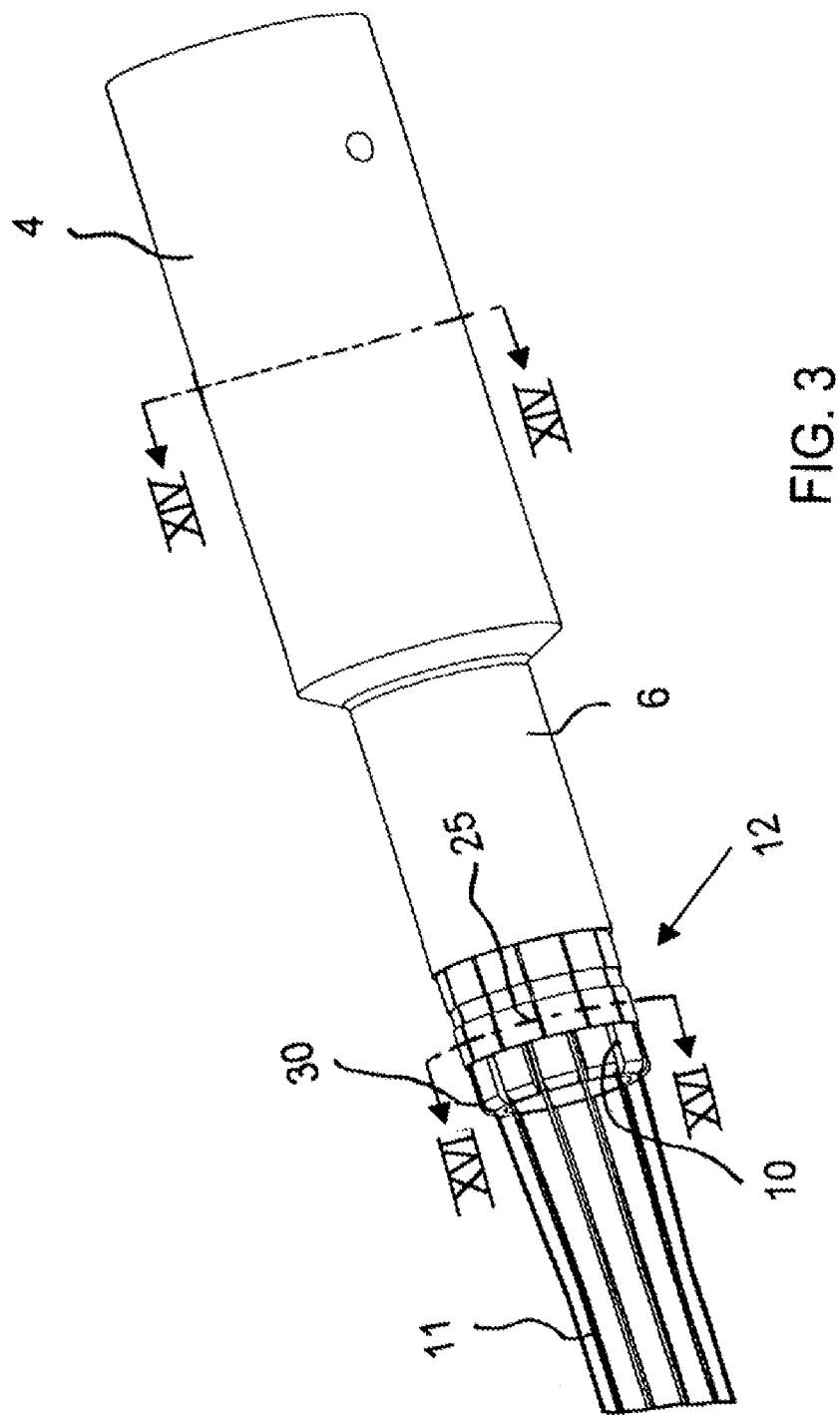
FIG. 3 is an enlarged, fragmentary, perspective view showing inner and outer handles, locking pads and tendons of the insertion device of the embodiment of FIG. 1.

Referring now to the figures of the drawings in detail and first, particularly to FIG. 1 thereof, there is seen a variably flexible insertion device 1 according to an exemplary embodiment of the invention. The insertion device 1 has a hollow body with a proximal end 2 for manipulation by an operator and for receiving an instrument 32 such as an endoscope or colonoscope seen in FIG. 5. The insertion device 1 also has a distal end 3 for insertion into a patient and for protrusion of the instrument 32. An outer handle 4 of the hollow body for the operator is disposed at the proximal end 2. The handle 4 has a vacuum port 5 formed therein. An outer sleeve 6 of the hollow body is disposed between the outer handle 4 and a nose tip 7 of the hollow body at the distal end 3. The outer sleeve 6 provides a flexible section with a given length extending beyond the handle 4.

FIG. 2 shows that the outer handle 4 contains an inner handle 30 of the hollow body having channel grooves 10 which permit movement of tendons 11. The tendons 11 extend substantially entirely over the given length of the flexible section provided by the outer sleeve 6. The tendons 11 may have a rounded or flattened cross section or a flattened cross section twisted along its length. A friction lock area 12 is disposed within the outer sleeve 6 for locking the tendons 11 in a manner to be discussed below. Vertebrae 13-17 are distributed along a flexible area 20 which is approximately 30 inches long. Whereas the vertebrae 14-17 allow movement of the tendons 11, the first vertebra 13 closest to the distal end 3 is fixed to the tendons 11. Although six vertebrae are shown, it is understood that more or fewer vertebrae may be provided, for example eight vertebrae, depending on the length of the device 1. The number of tendons 11 is also variable, although twelve is used as an example.

Figure 4:
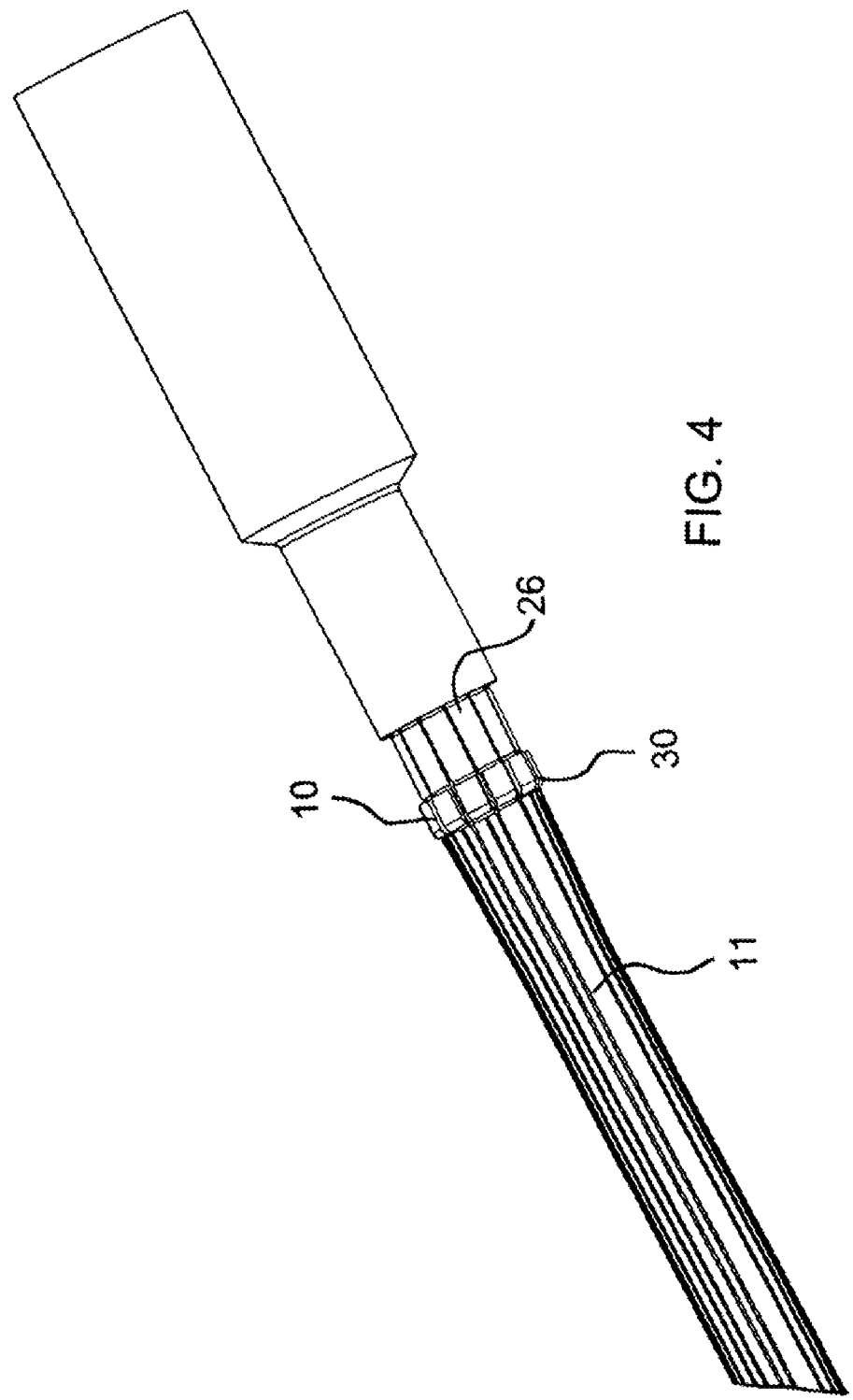
FIG. 4 is a view similar to FIG. 3, showing the inner and outer handles and a friction surface and grooves for the tendons.
Figure 16:
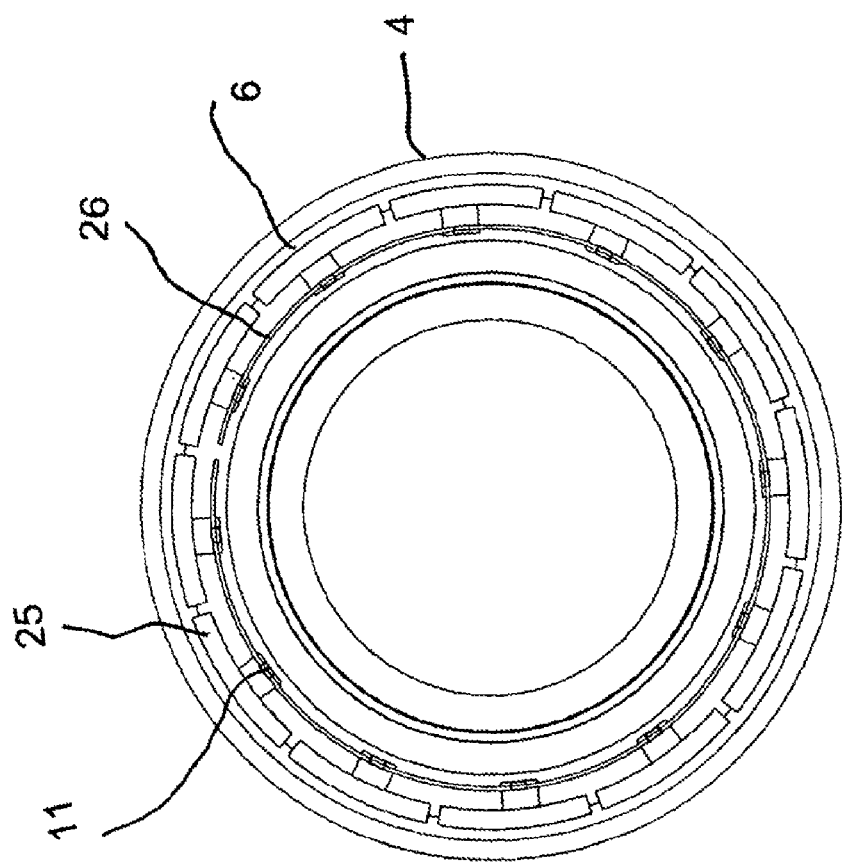
FIG. 16 is a cross-sectional view taken along a line XVI-XVI of FIG. 3, through the vertebrae with the tendons.

As seen in FIG. 3, a ring of locking pads 25 encircles the friction lock area 12. Each tendon 11 is assigned a respective locking pad 25, which is clearly shown in FIG. 16. The tendons 11 are disposed between the locking pads 25 and a friction surface 26 shown in FIGS. 4 and 16. The friction surface 26 is part of the inner handle 30 having the grooves 10 in which the tendons 11 move.

Figure 5:
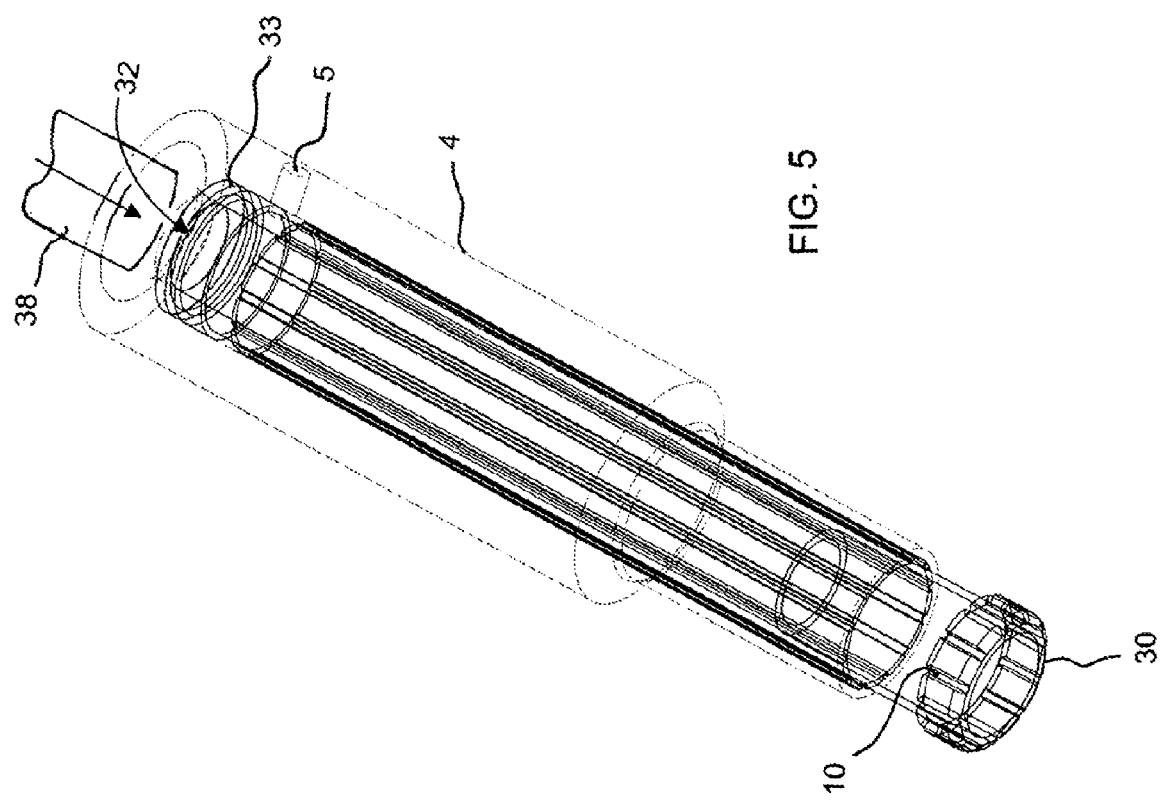
FIG. 5 is a perspective view of a portion of the insertion device of the embodiment of FIG. 1, showing details of the inner and outer handles.

FIG. 5 illustrates the outer handle 4 as well as the inner handle 30 with the channel grooves 10 for the tendons 11. The outer handle 4 is shown as being transparent in FIG. 5, so as to be able to illustrate an entrance 32 for the surgical instrument 38, such as an endoscope or colonoscope, a groove 33 for receiving an O-ring and the vacuum port 5.

Figure 6:
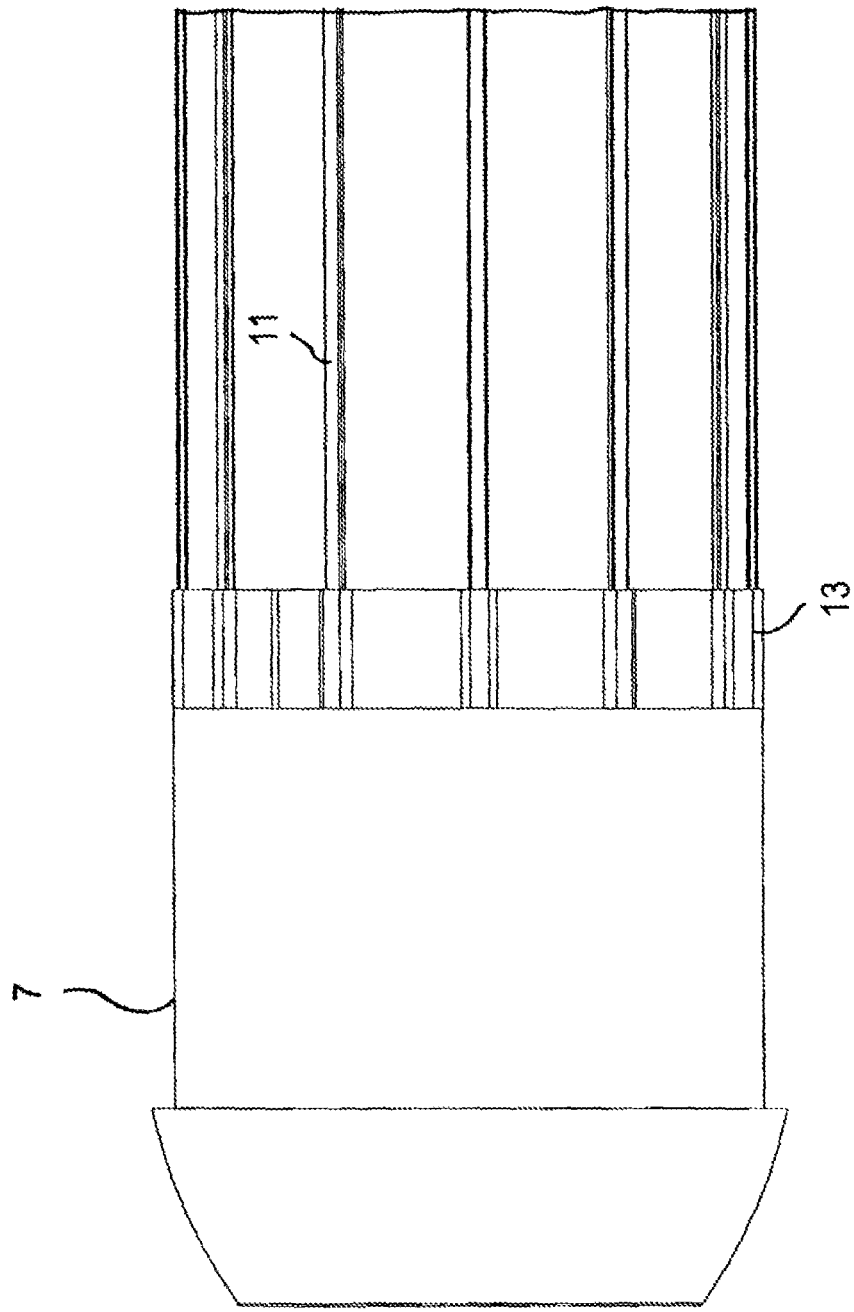
FIG. 6 is an enlarged, fragmentary, side-elevational view of a nose tip and tendons of the insertion device of the embodiment in FIG. 1.
Figure 7:
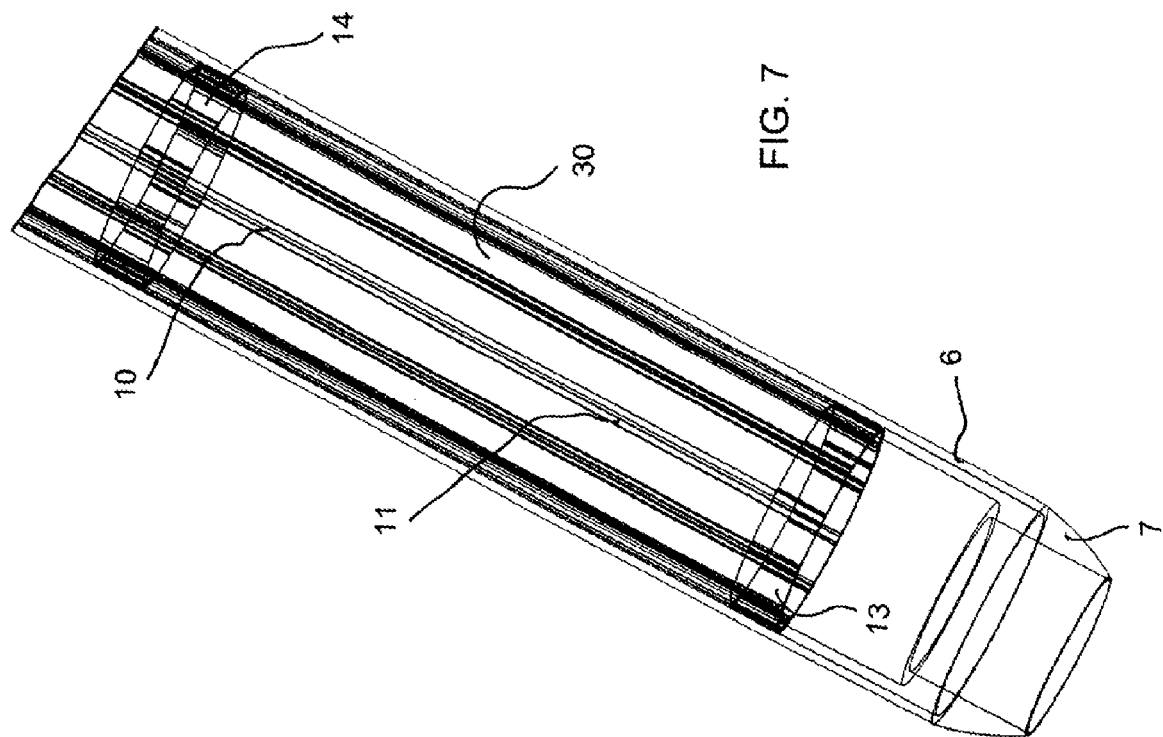
FIG. 7 is a fragmentary, perspective view of the nose tip showing details of the tendons and vertebrae.

FIG. 6 shows the region of the nose tip 7. The tendons 11 are fixed and welded to the first vertebra 13. FIG. 7 also shows the tendons 11 fixed to the first vertebra 13 as well as the second vertebra 14 under which the tendons are free to move in the channel grooves 10 formed in the inner handle 30.

Figure 8:
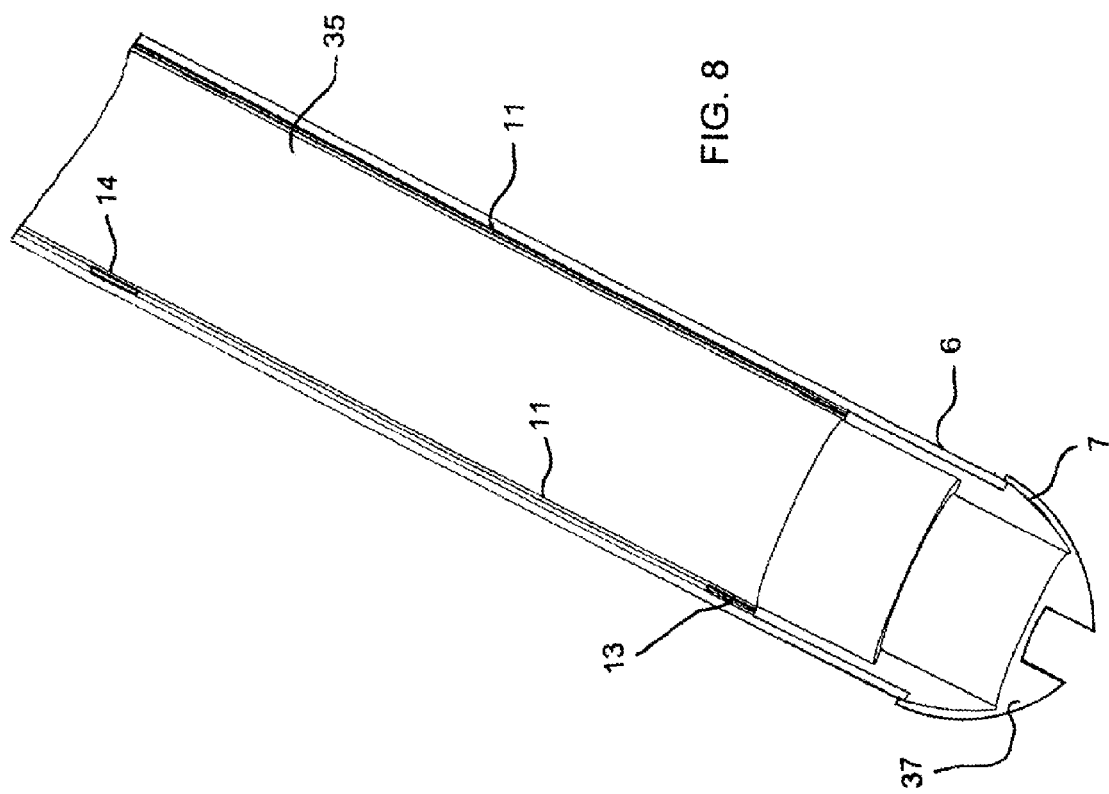
FIG. 8 is a fragmentary, longitudinal-sectional view of the nose tip and vertebrae.

The sectional view of FIG. 8 illustrates the outer sleeve 6, the nose tip 7, two tendons 11, as well as the tendons being welded to the first vertebra 13 and being freely movable in the second vertebra 14. An inner sleeve 35 of the hollow body is also shown in FIG. 8. FIG. 8 additionally shows an end cap 37 to be snapped-on at the distal end to accommodate different sized instruments or scopes 38.

Figure 9:
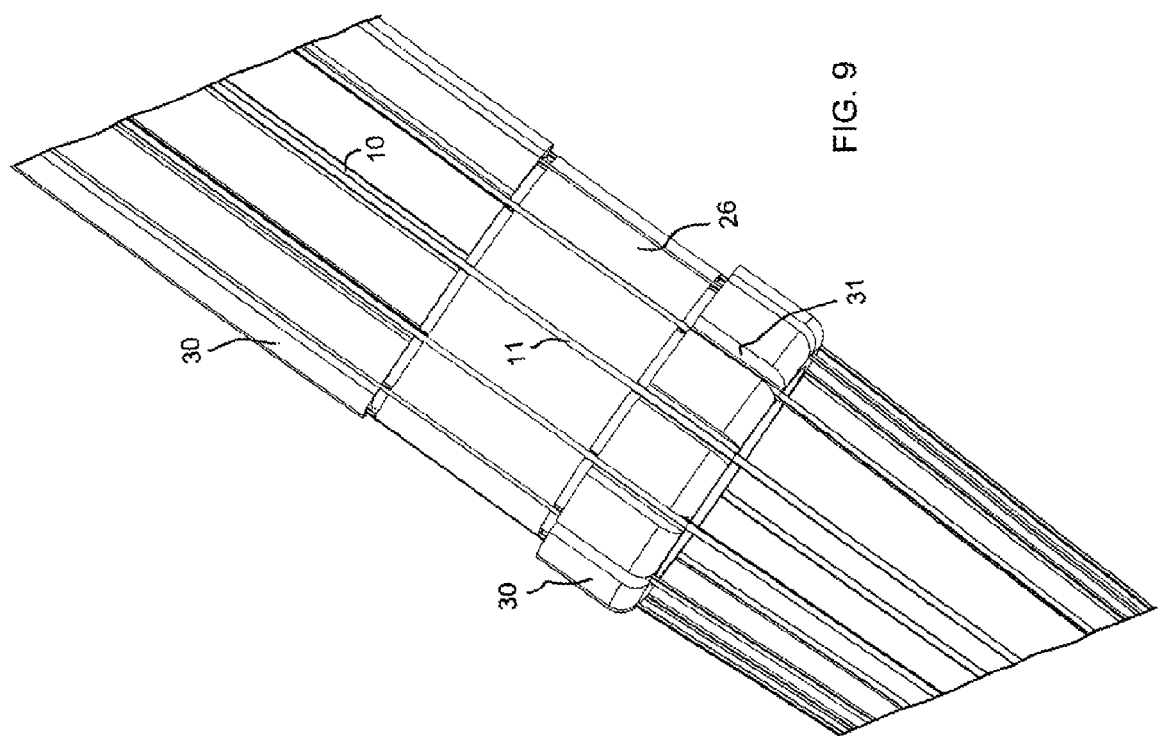
FIG. 9 is an enlarged, fragmentary, perspective view of the tendons over a friction zone.

FIG. 9 shows how the tendons 11 are freely movable in the channel grooves 10 in the inner handle 30 and pass over the friction surface 26.

Figure 10:
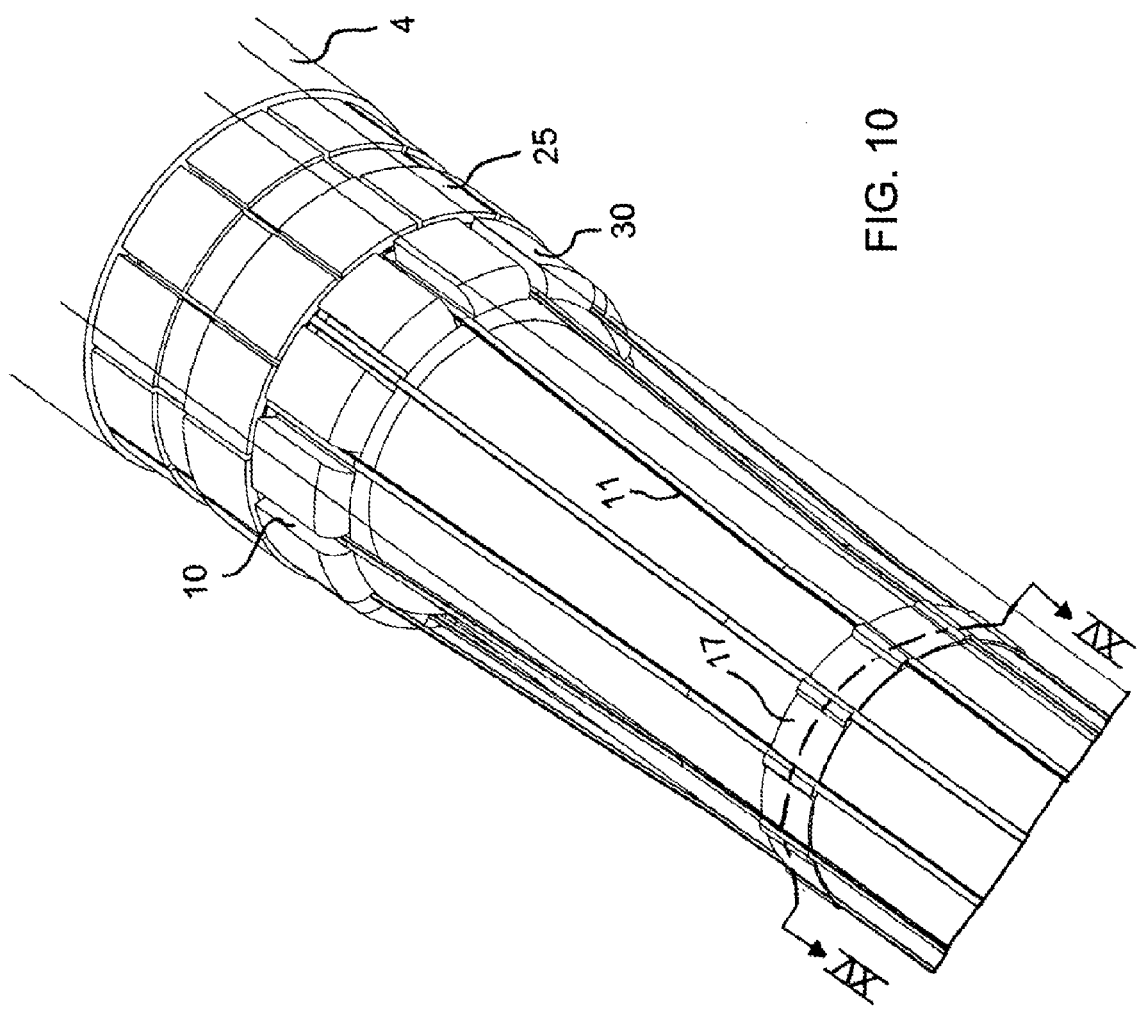
FIG. 10 is a fragmentary, perspective view illustrating the tendons in transition and locking.
Figure 15:
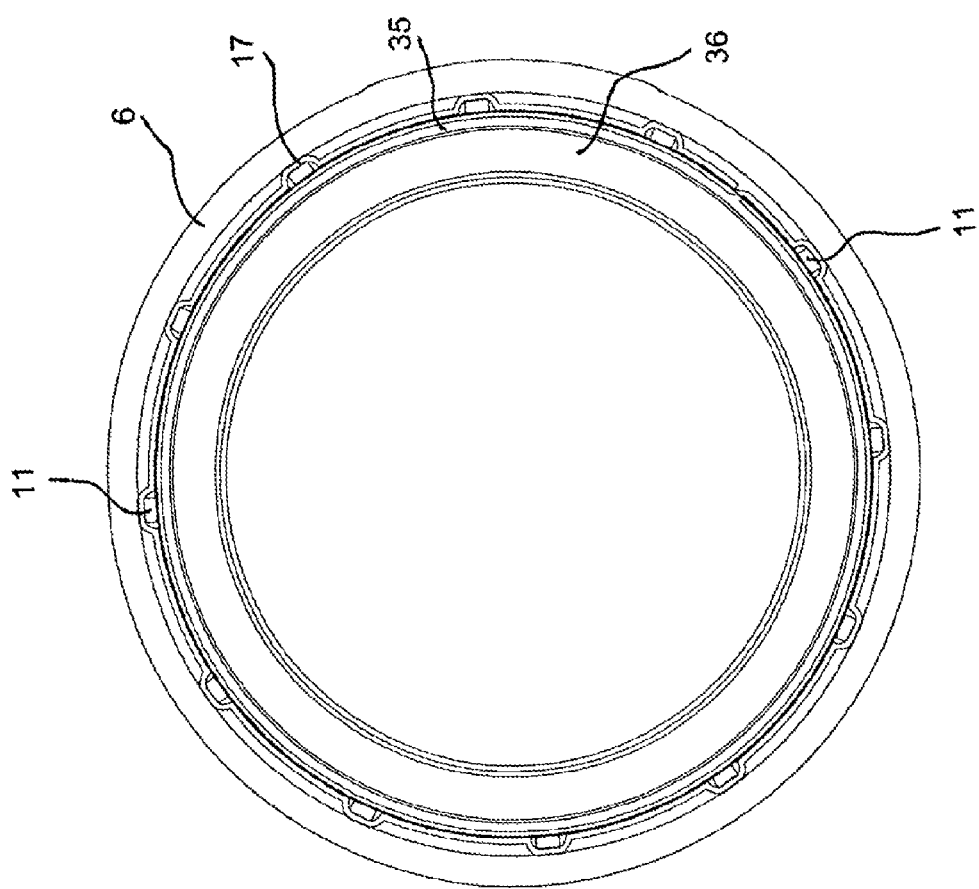
FIG. 15 is a cross-sectional view taken along a line XV-XV of FIG. 10, through the vertebrae with the tendons.

FIG. 10 also shows the friction locking pads 25, the inner handle 30 with the grooves 10 and the tendons 11 passing through the grooves 10 and under the fifth vertebra 17. The cross section of the vertebra 17 illustrated in FIG. 15 additionally shows a coil 36 of the hollow body disposed within and supporting the inner sleeve 35. The coil may be a wire which is TEFLON- or hydrophilic-coated to ease insertion of an endoscope or colonoscope. The stiffness or spring constant k of the coil 36 tends to maintain the device 1 in a straight condition. However, as will be explained in detail below, the device 1 does not remain straight when held horizontal in its flexible state. The coil 36 is used to maintain the round cross section of the device 1 while it is flexed.

Figure 11:
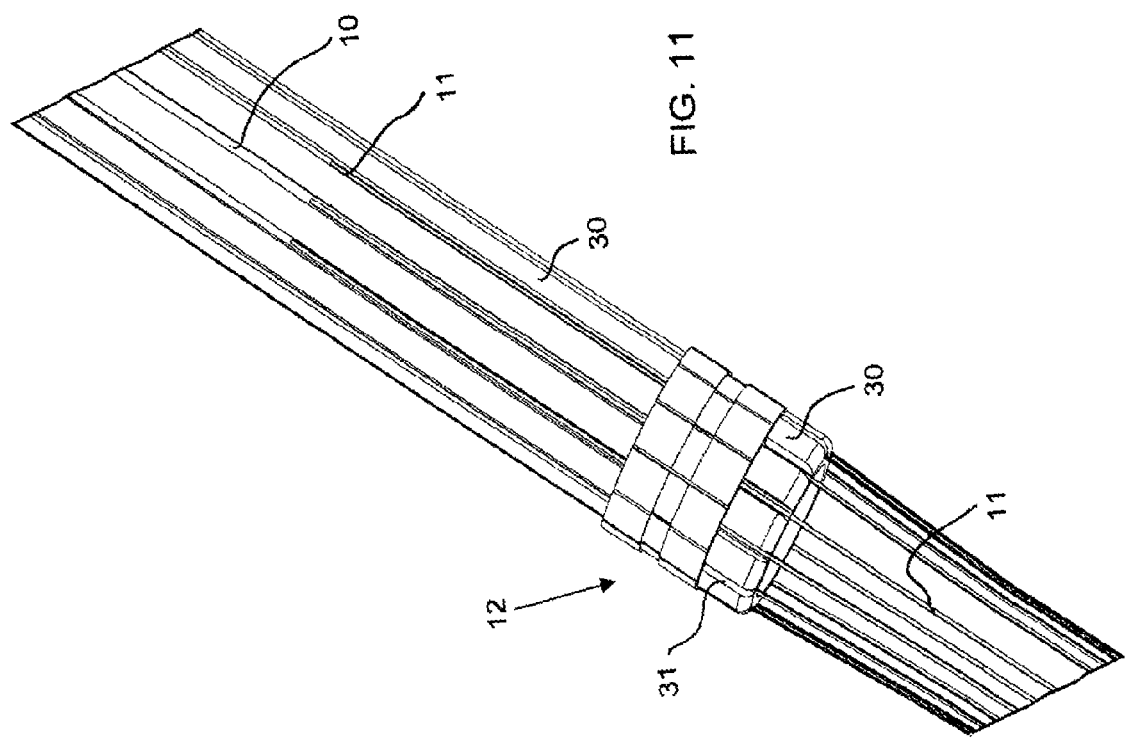
FIG. 11 is a fragmentary, perspective view showing the locking pads for the tendons.

The view of FIG. 11 shows the tendons 11 passing through the channel grooves 10 formed in the inner handle 30 and under the friction locking pads 25. The tendons 11 are freely movable in the channel grooves 10, except when pinched between the friction locking pads 25 and the friction surface 26 in the friction lock area 12.

Figure 12:
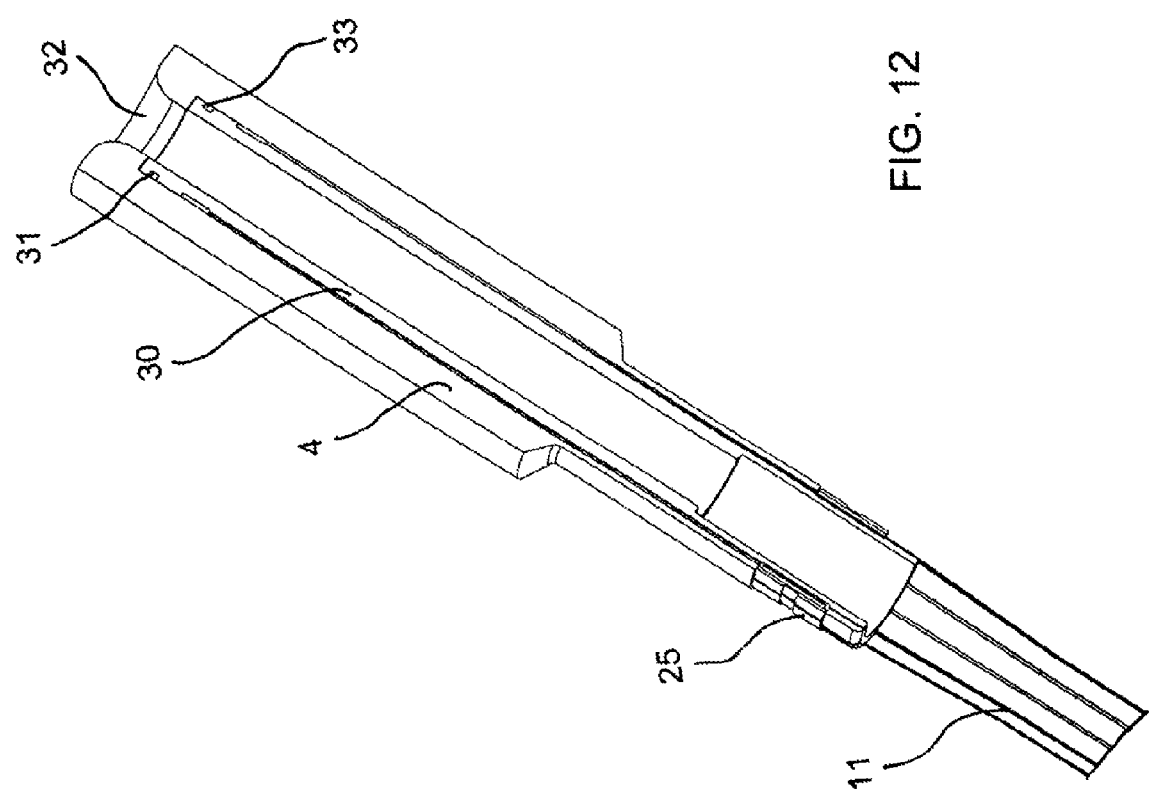
FIG. 12 is a fragmentary, longitudinal-sectional view of the handle of the embodiment of FIG. 1.
Figure 14:
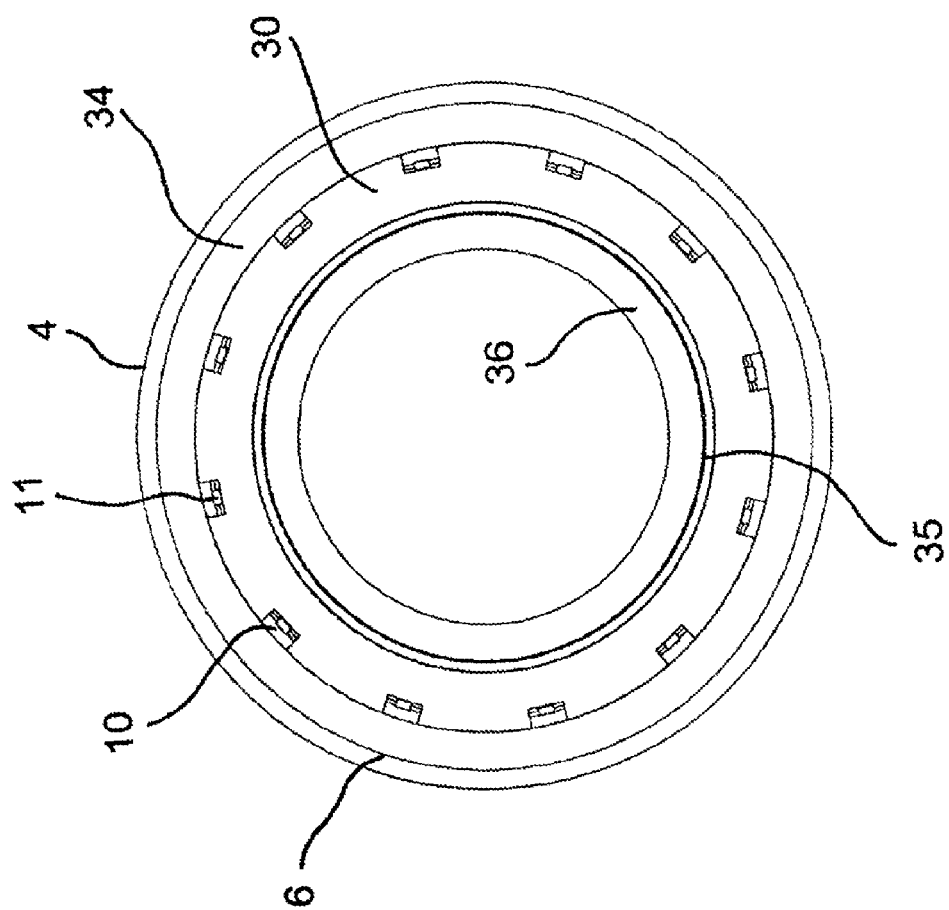
FIG. 14 is a cross-sectional view taken along a line XIV-XIV of FIG. 3, through the handle assembly during transition.

The cross-sectional view of FIG. 12 shows an O-ring 31 disposed in the groove 33. FIG. 14 shows a space 34 between the outer handle 4 and the inner handle 30. The space 34 is sealed by the O-ring 31 and communicates with the vacuum port 5 for applying positive and negative pressure (vacuum) to the space.

Figure 13:
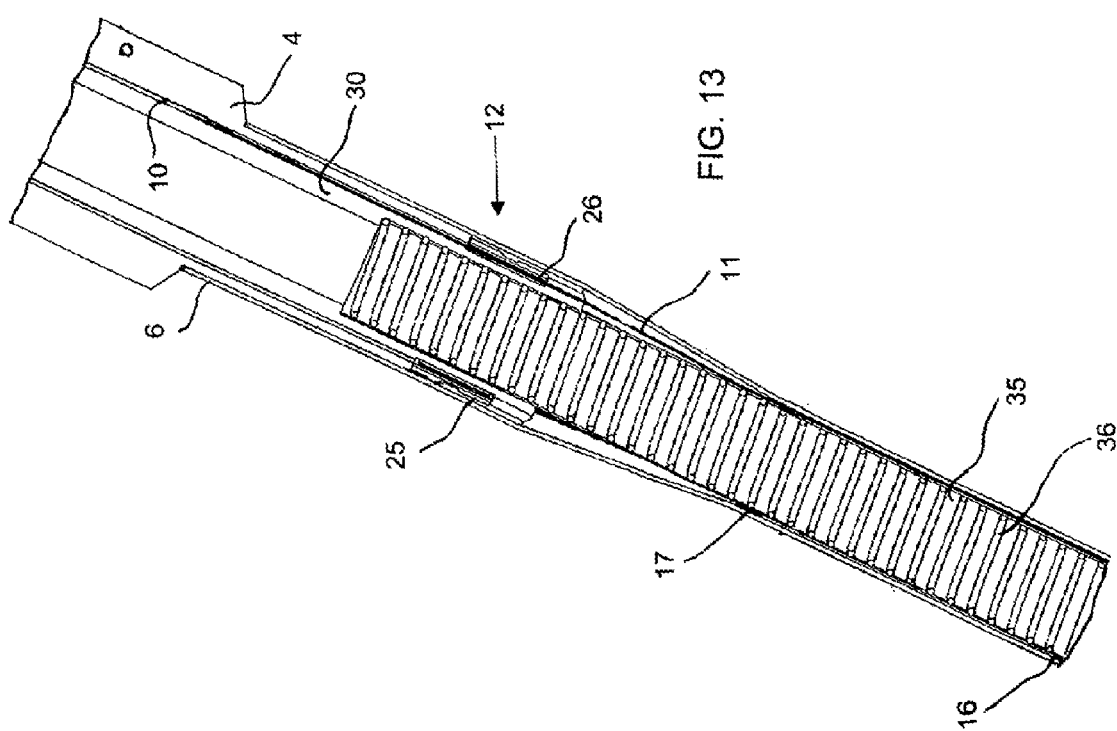
FIG. 13 is a fragmentary, longitudinal-sectional view of a handle locking area.

FIG. 13 is a cross-sectional view illustrating details of the friction lock area 12. It may be seen that the tendons 11 which pass below the vertebrae 16, 17 are pinched between the friction locking pads 25 and the friction surface 26 in the friction area 12.

Figure 18:
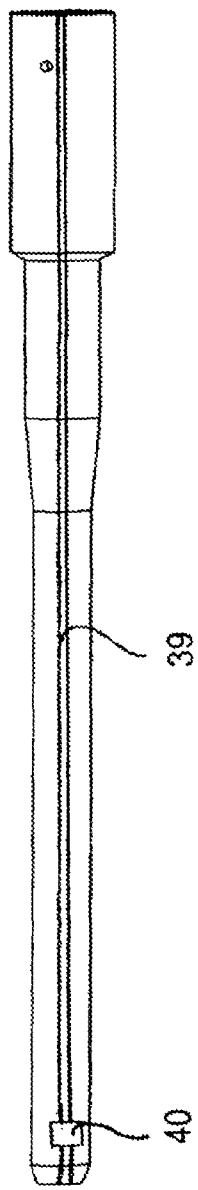
FIG. 18 is a view similar to FIG. 11 showing a slit hollow body with a zipper closure.
Figure 19:
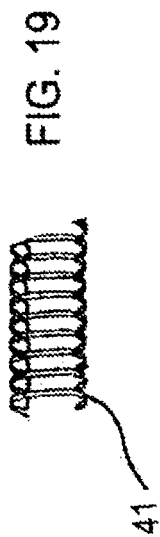
FIG. 19 is a perspective view of a coil used with the device of FIG. 18.

According to another embodiment of the invention which is illustrated in FIG. 18, the hollow body 4, 6, 7, 30, 35, 36 has a longitudinal slit 39 formed therein for radially loading the hollow body onto the instrument 38. The slit has a closure 40, such as a slide or press zipper used for plastic storage bags, permitting the device to be resealed after the hollow body has been loaded. The coil in this case is a ring wire, double wire, double loop or twin loop binding 41 seen in FIG. 19, such as is used for notebooks.

Figure 17:
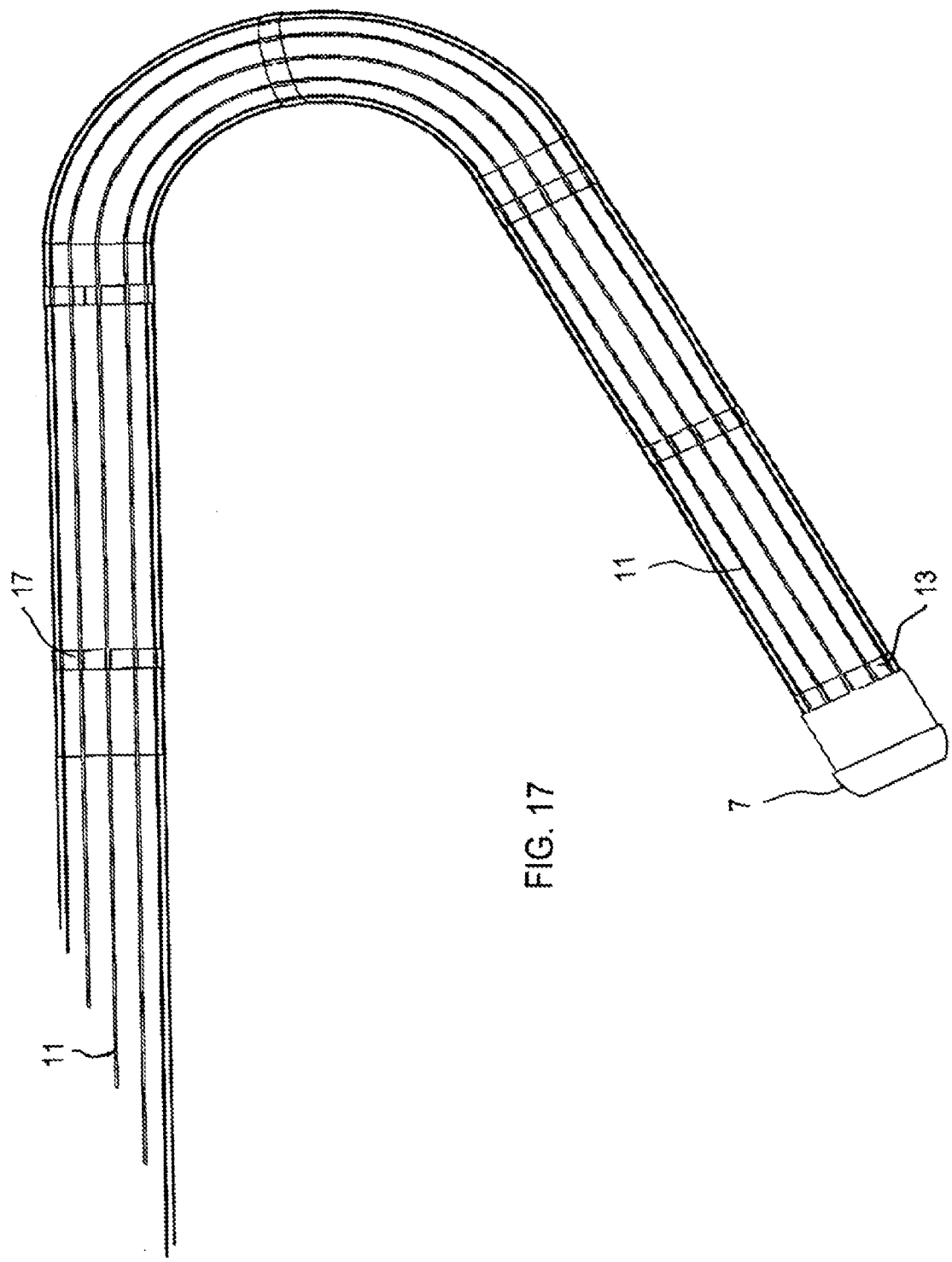
FIG. 17 is a fragmentary, side-elevational view of the device of the embodiment of FIG. 1 in a flexed condition, showing the nose tip, the vertebrae and the effect of bending on the tendons.

The operation of the variably flexible insertion device 1 is best understood by making reference to FIG. 17 in conjunction with the above-described figures. After the device 1 is forced into a flexed condition against the stiffness or spring constant k of the coil 36 as seen in FIG. 17, for example upon traversing the rectosigmoid junction, and it is desired to maintain that flexed condition for guiding an endoscope, such as a colonoscope, vacuum is applied to the space 34 through the vacuum port 5. When suction is applied to create the vacuum, it causes the inner sleeve 35 and the outer sleeve 6 to firmly contact each other with the tendons 11 sandwiched and frictionally locked therebetween. Therefore, the vacuum port 5 acts as a device for transitioning the hollow body 4, 6, 7, 30, 35, 36 between the relatively flexible condition and the relatively stiff condition through the application of a vacuum. Most of the stiffness causing the device 1 to maintain its flexed condition is accomplished by this interaction of the inner and outer sleeves and the tendons. However, additional stiffness may optionally be accomplished by providing the friction locking pads 25 which contract and hold the tendons 11 against the friction surface 26 in the friction area 12. The device 1 therefore maintains its flexed condition. FIG. 17 shows that in the flexed condition, the tendons 11 at the outer periphery of the bend become shorter and the tendons 11 at the inner periphery of the bend become longer, since they are all fixed in place at the first vertebra 13.

The tendons or wires 11 are passive elements which are not in tension at any time. The tendons float within the hollow body when it is in the flexible condition, except at the distal end. The tendons are frictionally locked by the inner sleeve 35 and the outer sleeve 6 when the hollow body is in the stiff condition. However, in both the relatively flexible condition and the relatively stiff condition, the tendons have no active control imposed on them and are not pulled or constrained.

When it is desired to resume flexibility of the device 1, the vacuum in the space 34 is replaced by air at ambient or positive pressure. This causes the inner sleeve 35 and the outer sleeve 6 to release the tendons 11 and allows the stiffness or spring constant k of the coil 36 to place the device 1 into its normally flexible condition. If friction locking pads 25 are used, they also relax and expand, which in turn releases the tendons 11.

The device is intended to be used in a manner similar to prior art devices. Therefore, the device will be placed over the endoscope. The endoscope will then be inserted into the rectum. The device will then be pushed in its flexible condition, to follow the curvature of the scope. The device will then be stiffened, allowing the scope to be pushed forward with less pressure exerted on the colon of the patient. This procedure can be repeated until the scope reaches the cecum.

An alternative use of the device is to aid in small bowel endoscopy. The device is placed over the endoscope. The endoscope is inserted into the patient transorally, through the stomach and then partially into the small bowel. The device is then pushed in its flexible condition, to follow the curvature of the scope. The device is then stiffened, allowing the scope to be pushed forward without the scope looping in the stomach.

Another use of the device is for aiding in access to internal body parts, such as the gallbladder, through an opening of an internal body cavity, such as the stomach. The device is placed over the endoscope. The endoscope is inserted into the patient transorally, through the stomach and then up against the internal surface of the stomach. The device is then pushed in its flexible condition, to follow the curvature of the scope. The device is then stiffened, allowing the surgeon to create an opening in the stomach wall without the scope looping in the stomach. Once the opening is created, the device and the scope can be advanced outside the stomach. The device can then be stiffened to create a stable platform to perform surgical procedures outside of the stomach. The device could contain one or more features (i.e. balloons) for sealing the outer periphery of the device to the stomach wall to prevent gastric fluids from exiting the stomach.

According to the other embodiment of the invention, the device is capable of being loaded on the instrument or scope after the scope is inserted into the patient. In this embodiment, the slit down the length of the device allows it to be loaded on the scope so that the scope is inserted radially into the hollow body.

Figure 20:
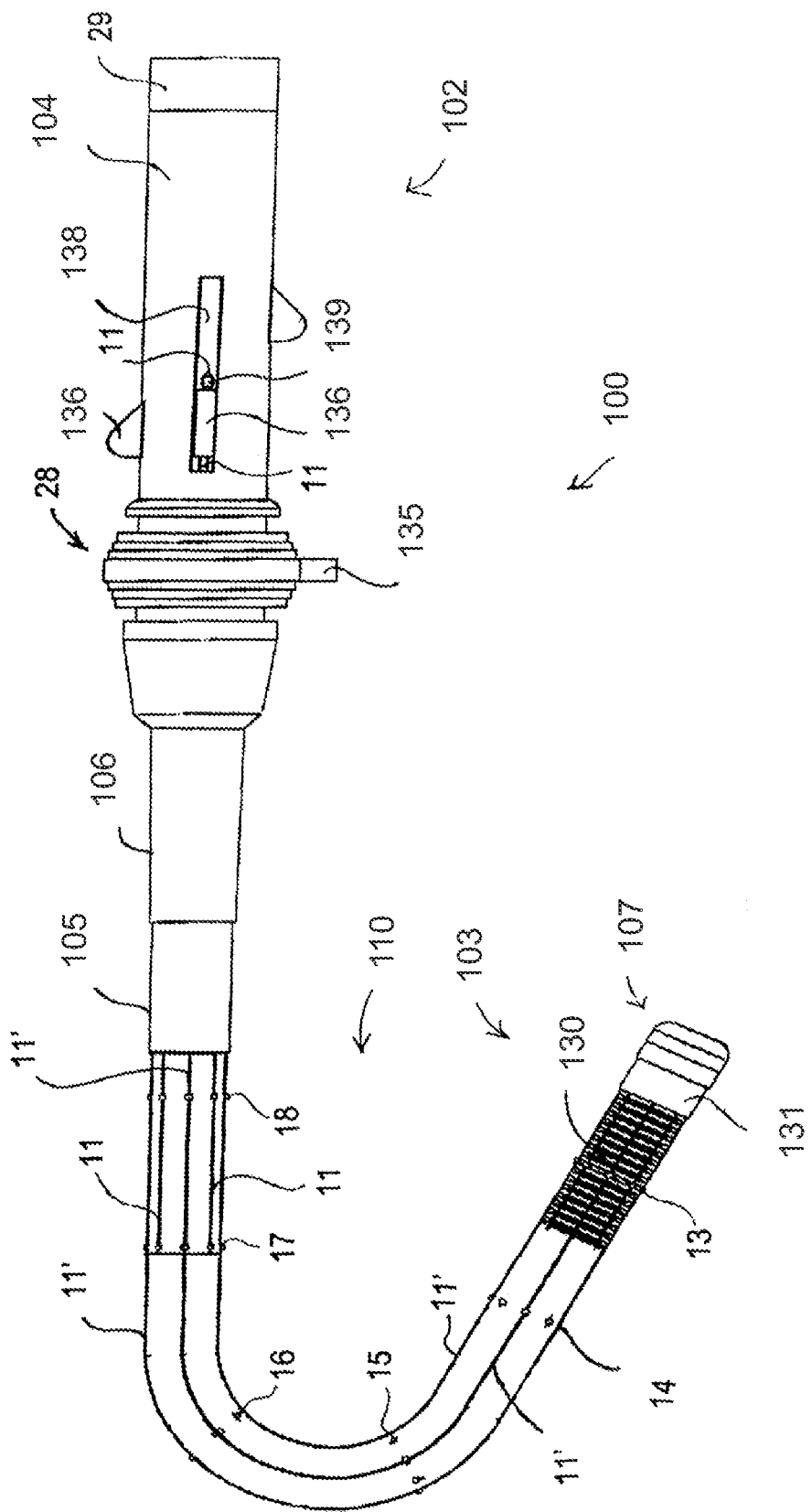
FIG. 20 is a diagrammatic, side-elevational view of a torque-transmitting, variably-flexible, corrugated insertion device according to another exemplary embodiment of the invention, in which an outer jacket has been partly removed to show corrugations, tendons and vertebrae and in which the device has been steered to the right.

Referring now to FIG. 20, there is seen a torque-transmitting, variably-flexible, corrugated insertion device 100 according to another exemplary embodiment of the invention. The insertion device 100 has a hollow body with a proximal end 102 for manipulation by an operator and for receiving an instrument such as an endoscope or a colonoscope. The insertion device 100 also has a distal end 103 for insertion into a patient and for protrusion of the instrument. A handle 104 of the hollow body for control by the operator is disposed at the proximal end 102. An outer jacket 105 of the hollow body extends to a tip 107, which may be formed of rubber, at the distal end 103, but only a portion of the outer jacket has been shown in order to illustrate other details of the device disposed within the outer jacket 105. A flexible strain relief retainer 106 is disposed between the handle 104 and the outer jacket 105. The outer jacket 105 and the flexible strain relief retainer 106 provide a flexible section with a given length extending beyond the handle 104. The handle 104 has a sliding valve 28 and a septum valve assembly 29, which will be explained in greater detail below with regard to FIG. 21. The handle 4 also has a vacuum connection or nipple 135 for controlling stiffness of the device, as will be explained below as well. A corrugated tube 130, which is only illustrated in the region of the distal tip 107, actually extends to the flexible strain relief retainer 106.

The insertion device 100 may be steerable or non-steerable. If the device is steerable, a steering assembly 110 is provided which includes six vertebrae 13-18 shown as being disposed along the hollow body. However, more or fewer vertebrae can be provided in dependence on the length, diameter and use of the hollow body. Eight tendons 11, 11' are equally spaced apart about the circumference of the hollow body between the vertebra 17 and the handle 104, although only five can be seen in FIG. 20. Four of the tendons which extend from a tendon termination bushing 131 at the tip 107 to the handle 104 are so-called steering tendons 11'. Other tendons which only extend between the vertebra 17 and the handle 104 are so-called non-steering tendons 11.

Each of the four steering tendons 11' is attached at its proximal end to a respective knob 136 which slides within a respective slot 138 in the handle 104. A stop 139 is also disposed on each tendon 11'. When a knob 136 is slid proximally, it pushes a stop 139 and pulls a tendon 11' to steer the hollow body. In the condition shown in FIG. 20, the knob 136 at the bottom has been slid proximally so that the tip 107 of the hollow body has been steered downward. If different knobs 136 are moved, the hollow body will be steered in different directions. When the knobs 136 are forced distally, the knobs can freely slide independently of the tendons 11' to prevent buckling of the tendons 11'. It will be readily understood that if two of the knobs are slid proximally, the tip 107 will move in a direction between the two directions that each one of the knobs would have moved the tip if moved individually.

Figure 21:
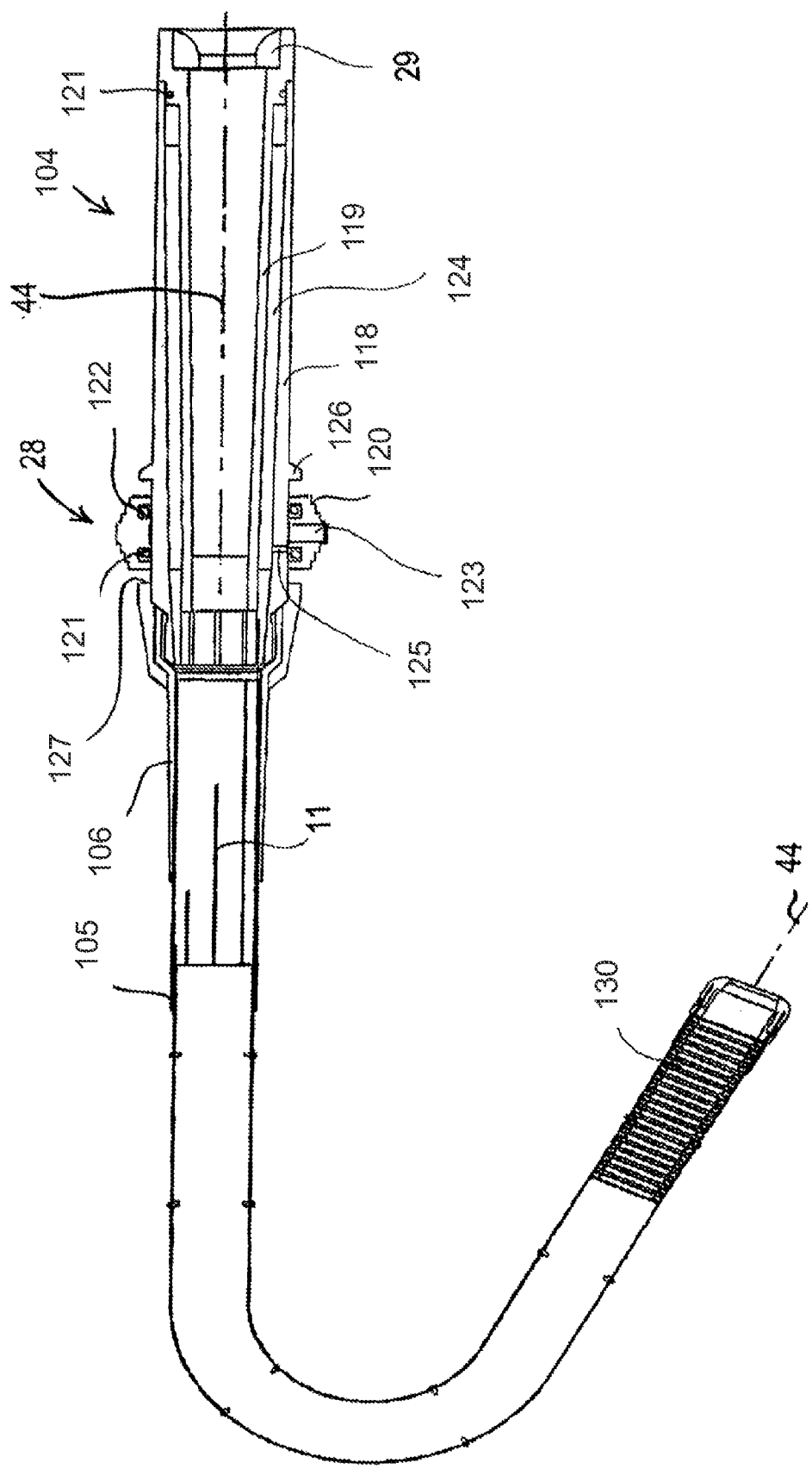
FIG. 21 is a side-elevational view of the insertion device of the embodiment of FIG. 20 in which corrugations are illustrated at the distal tip as in FIG. 20, and in which an outer covering of a handle has been removed.

In FIG. 21, an outer covering of the handle 104 has been removed to show details of the sliding valve 28 and the septum valve assembly 29. The handle 104 has an inner handle 119 disposed within an outer handle 118, defining an annular vacuum plenum volume 124 therebetween which extends in longitudinal direction of the handle 104. A vacuum inlet/outlet hole or port 125 is formed in the body of the outer handle 118 and communicates with the volume 124. A sliding so-called tire valve thumb grip 120 encircles the outer handle 118 and is sealed thereto by O-ring seals having O-rings 121 in recesses 122 in the grip 120. An O-ring seal is also disposed at the proximal end of the handle 104. The grip 120 also has a vacuum inlet/outlet 123 for the connection or nipple 135. When the grip 120 is slid toward an annular stop 126, the vacuum inlet/outlet 123 is not in alignment with the vacuum inlet/outlet hole 125. However, when the grip 120 is slid toward an annular stop 127, the vacuum inlet/outlet 123 and the vacuum inlet/outlet hole 125 are aligned, providing communication between the connection or nipple 135 and the volume 124. Therefore, during operation, the grip 120 is slid toward the stop 127 to apply vacuum to stiffen the hollow body or to vent the vacuum to the atmosphere or supply air at atmospheric pressure to make the hollow body flexible again. The grip 120 is slid toward the stop 126 to maintain the stiffened or flexible condition of the hollow body attained by vacuum or venting or air supply through the connection or nipple 135. The septum valve assembly 29 is in the form of an end cap which is inserted into the proximal end of the outer handle 118 and provides a so-called septum seal for insertion of an instrument 44, such as an endoscopy or a colonoscopy, represented by a dot-dash line. End caps with various sized openings may be used in dependence on the instrument being used. The instrument passes through the hollow body and emerges at the distal tip 107. A diaphragm seal is provided between the septum valve assembly 29 and the inner handle 119.

Figure 22:
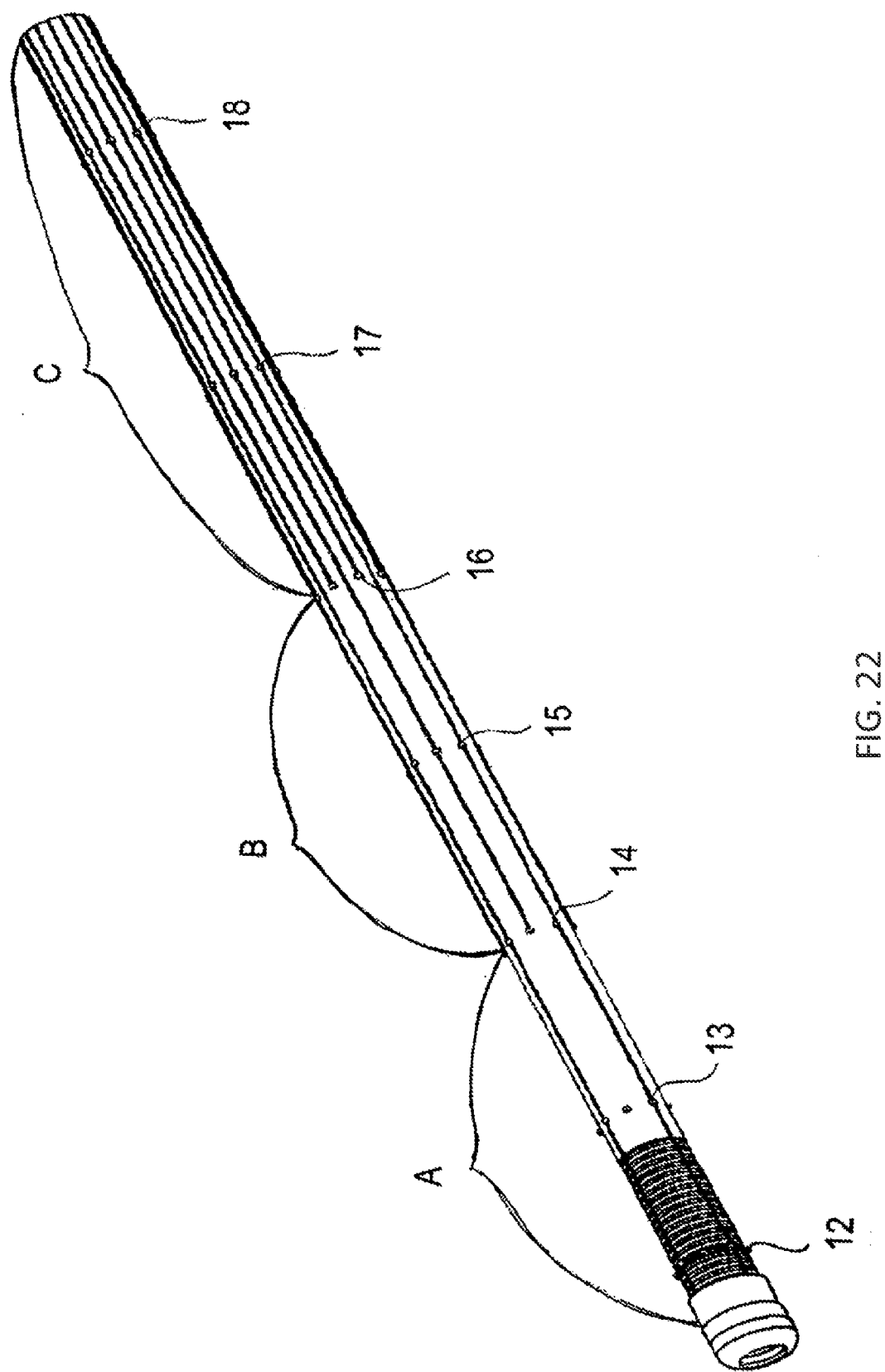
FIG. 22 is a perspective view showing stiffener zones of the insertion device of the embodiment of FIG. 20 and illustrating corrugations at the distal tip.

If the insertion device 100 is non-steerable, the number of tendons 11 may also be varied as shown in FIG. 22 to provide stiffness zones. For example, a stiffness zone A closest to the distal tip 107 has four tendons, a stiffness zone B has eight tendons and a stiffness zone C closest to the handle 104 has sixteen tendons. A zone with more tendons will be stiffer than a zone with fewer tendons. The number of tendons and their location within the zones as well as the number of zones can be increased or decreased, depending on the application of the device. Vertebrae 12-18, which in this case are seven in number, are also shown. The four tendons in the zone A all end at the termination bushing 131 but are free to slide elsewhere. Four of the eight tendons in zone B, which do not extend to zone A, are fixed at the vertebra 14 between zones A and B, which is therefore referred to as a termination vertebra, but are free to slide elsewhere. Similarly, eight of the sixteen tendons in zone C, which do not extend into zones A and B, are fixed at the termination vertebra 16 between zones B and C but are free to slide elsewhere.

Figure 23:
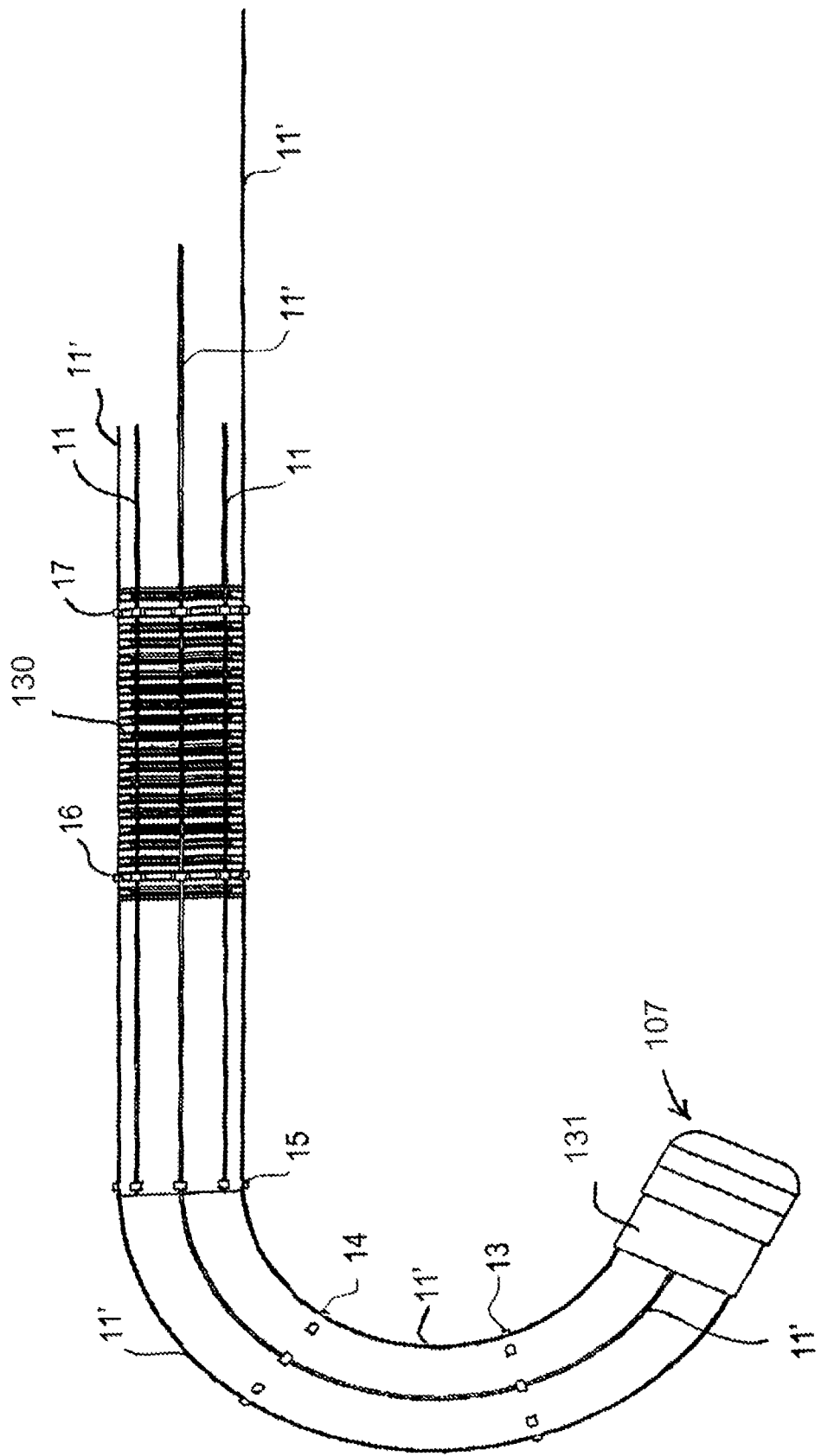
FIGS. 23 and 24 are fragmentary, side-elevational views of a steering assembly of the insertion device of the embodiment of FIG. 20 with corrugations illustrated in different locations.
Figure 24:
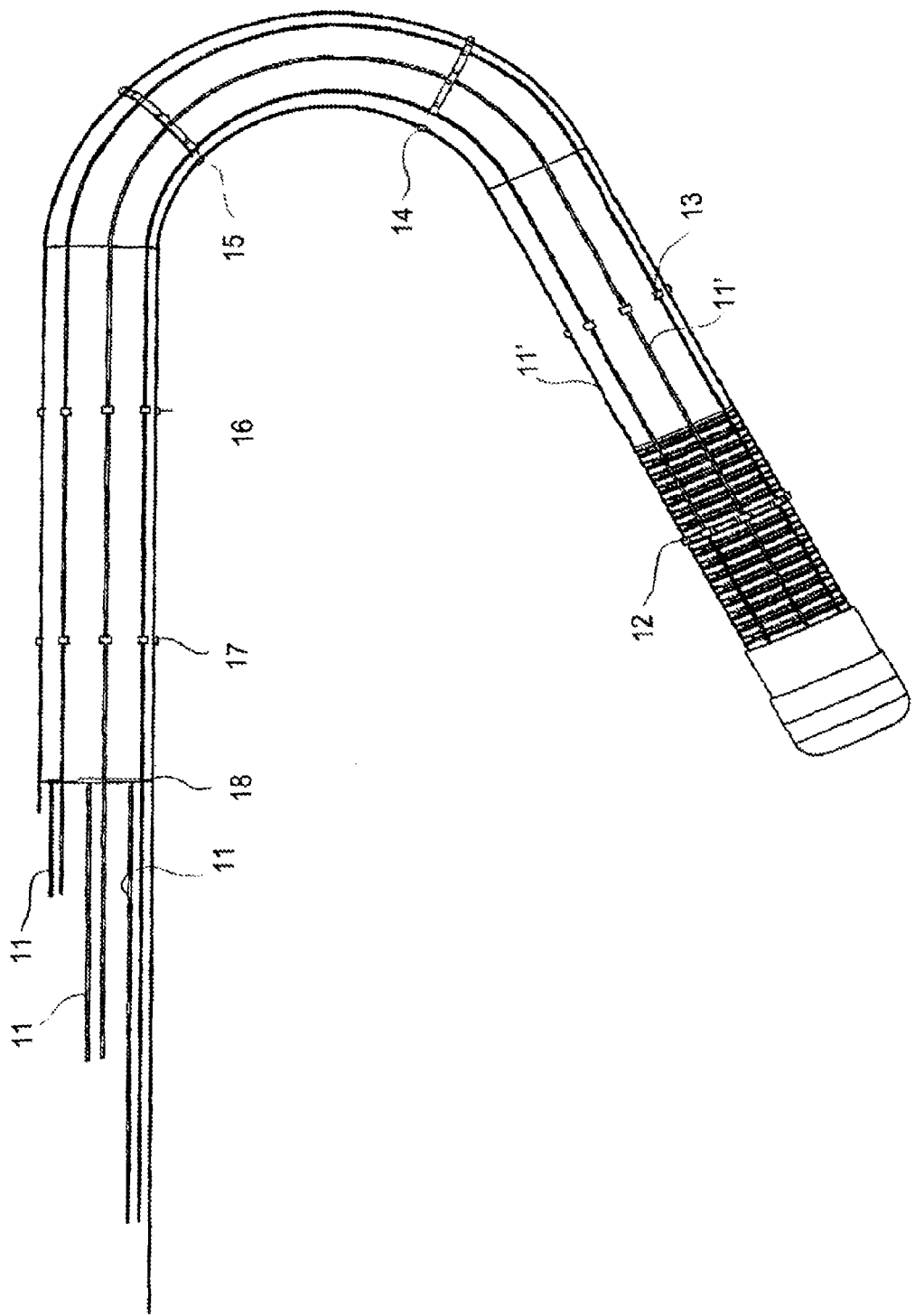

FIG. 23 shows the device 100 with the handle 104 removed, from which it can be seen that the four steering tendons 11' of the steering assembly 110 continue toward the handle from the tip 107, whereas the non-steering tendons 11 only run from the termination vertebra 15 to the handle. It is also seen that as the insertion device is steered, the steering tendons 11' on the outside of the bend become shorter and the steering tendons 11' on the inside of the bend become longer. FIG. 24 shows a similar view to FIG. 23, in which it can be seen how a greater number of vertebrae react to bending. In the case of FIG. 24, eight steering tendons 11' extend to the termination bushing 131, whereas six non-steering tendons 11 extend from the termination vertebra 18 to the handle.

Figure 25:
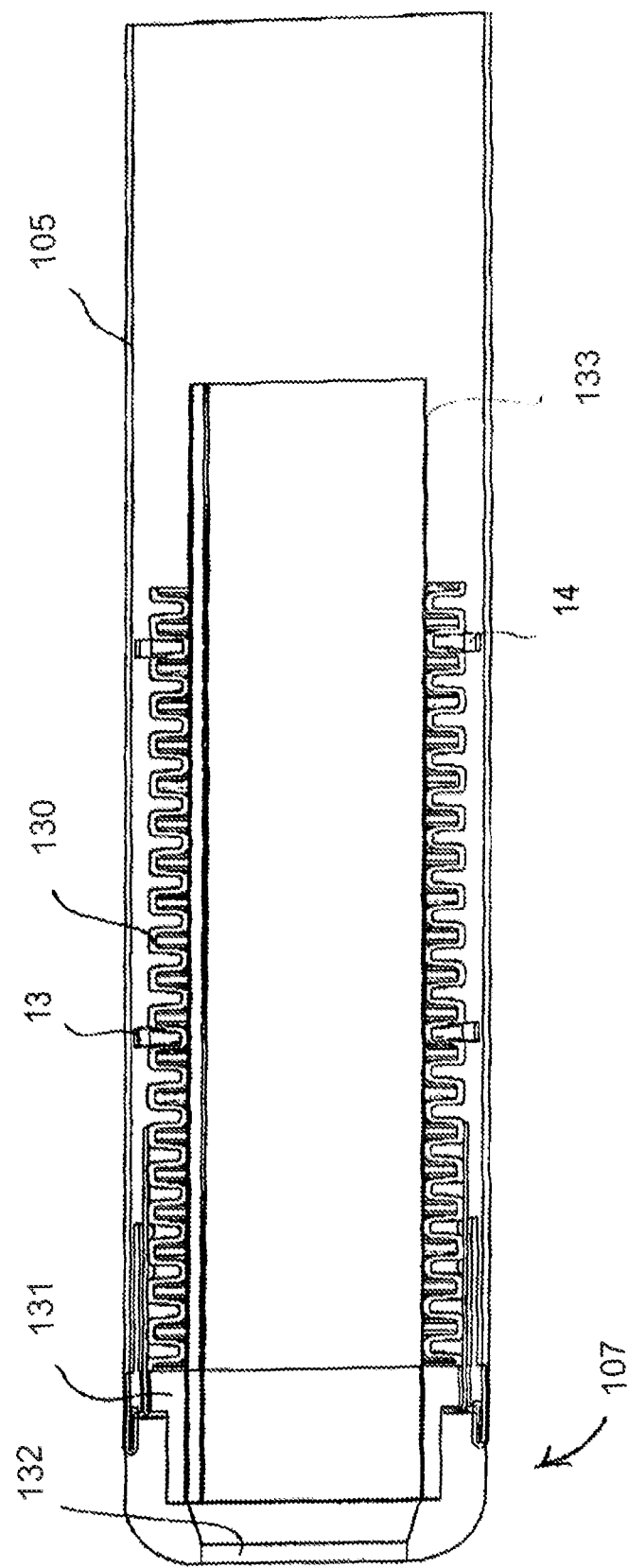
FIG. 25 is an enlarged, fragmentary, longitudinal-sectional view of a distal tip region of the insertion device of the embodiment of FIG. 20.
Figure 26:
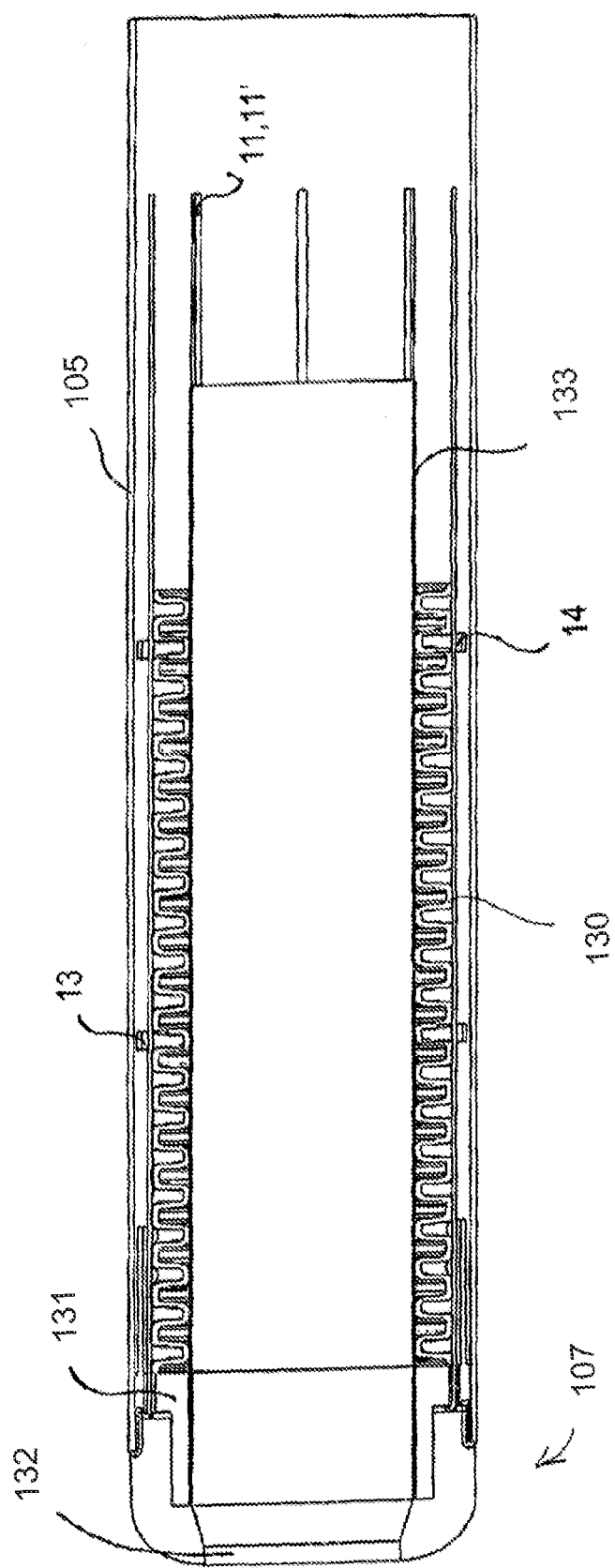
FIG. 26 is a view of the insertion device similar to FIG. 25, in which tendons have been shown.

In the enlarged view of FIG. 25, a portion of the corrugated tube 130 in the region of the tip 107 and the termination bushing 131 are shown. The tendons 11, 11', which have been omitted in FIG. 25 for the sake of clarity, are shown in FIG. 26 as extending through the vertebrae 13, 14 to the termination bushing 131. A tip restrictor 132 can also be seen at the tip 107. It may also be seen that an inner liner 133 extends within the corrugated tube 130. One purpose of the inner liner is to provide a surface on which the instrument will pass smoothly within the corrugated tube. The corrugated tube 130 may be formed of nylon or another suitable material. The inner liner 133 is made from a sheet of white plastic material which has an adhesive coating on one side. The inner liner 133 is rolled around an inflatable mandrel and heated in an oven, to form a bonded seam 42 (shown in FIGS. 30-32) and is sealed to an inner surface of the corrugated tube 130. The corrugations of the corrugated tube 130 have peaks and valleys. As viewed from within the corrugated tube 130, the inner liner 133 adheres to the peaks and extends somewhat into the valleys of the corrugations as dimples. Therefore, as the insertion device bends, the inner liner 133 stays tight along the corrugations on the outside of the bend and crinkles at the inside of the bend. The peaks and valleys of the corrugations also need not be of equal length along the length of the corrugated tube 130. For example, 70% of the length may be peaks and 30% valleys or 80% of the length may be peaks and 20% valleys. These variations will add to the adhesion of the inner liner to the corrugated tube and reduce the formation of dimples. However, a 50/50 corrugation ratio is shown in the figures. The outer jacket 105 may be formed of polyurethane or another suitable material which is similarly a flat sheet that is rolled and seamed. The outer jacket 105 and the inner liner 133 both extend to the termination bushing 131, which may be formed of polycarbonate.

Figure 27:
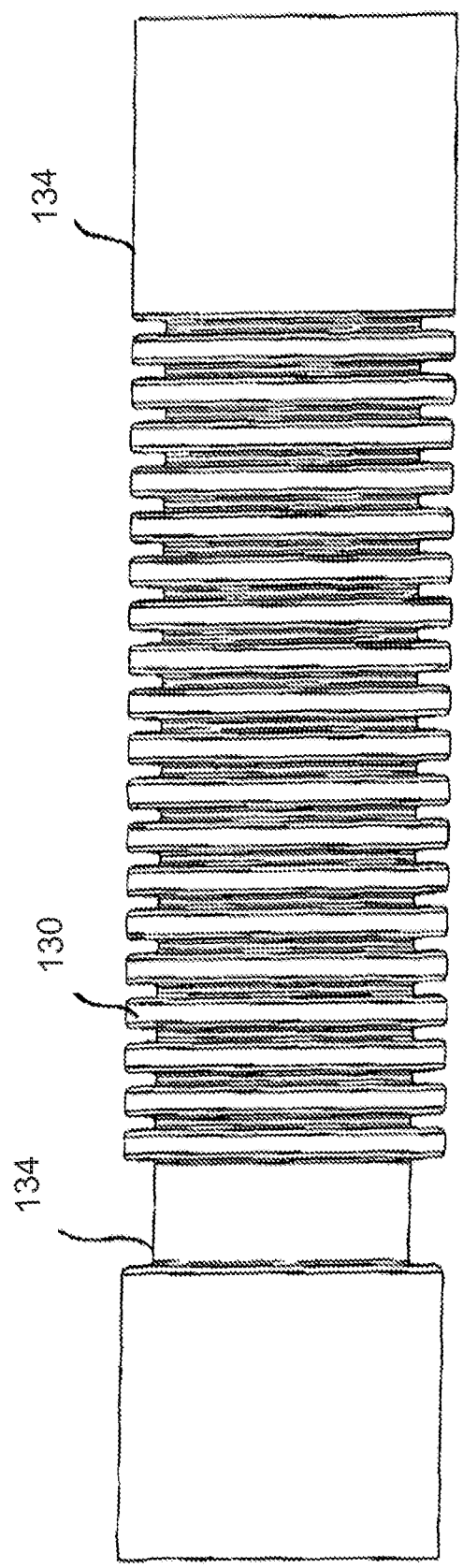
FIG. 27 is an elevational view of a corrugated tube of the insertion device of the embodiment of FIG. 20 in which straight and stepped cuffs have been shown.
Figure 28:
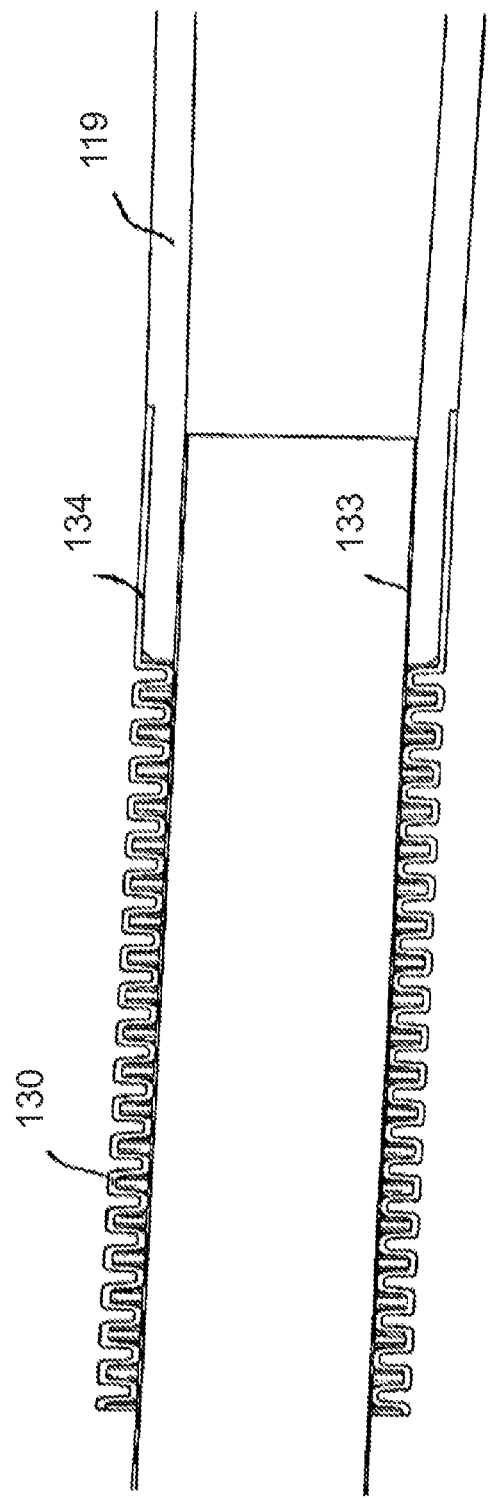
FIG. 28 is a fragmentary, longitudinal-sectional view of the insertion device of the embodiment of FIG. 20 in which an inner liner, an inner handle and a corrugation cuff have been shown.

The corrugated tube is cuffed in order to prevent leakage paths for the vacuum applied within the hollow body and to protect the material of the inner liner. FIG. 27 illustrates two types of molded corrugation cuffs 134, namely a straight cuff on the left and a stepped cuff on the right, of the figure, both with a 50/50 corrugation ratio. FIG. 28 shows the inner handle 119 which is attached to a corrugation cuff 134, as well as the inner liner 133 that is sealed to the corrugated tube 130 and to the inner handle 119 to prevent a vacuum leakage path.

Figure 29:
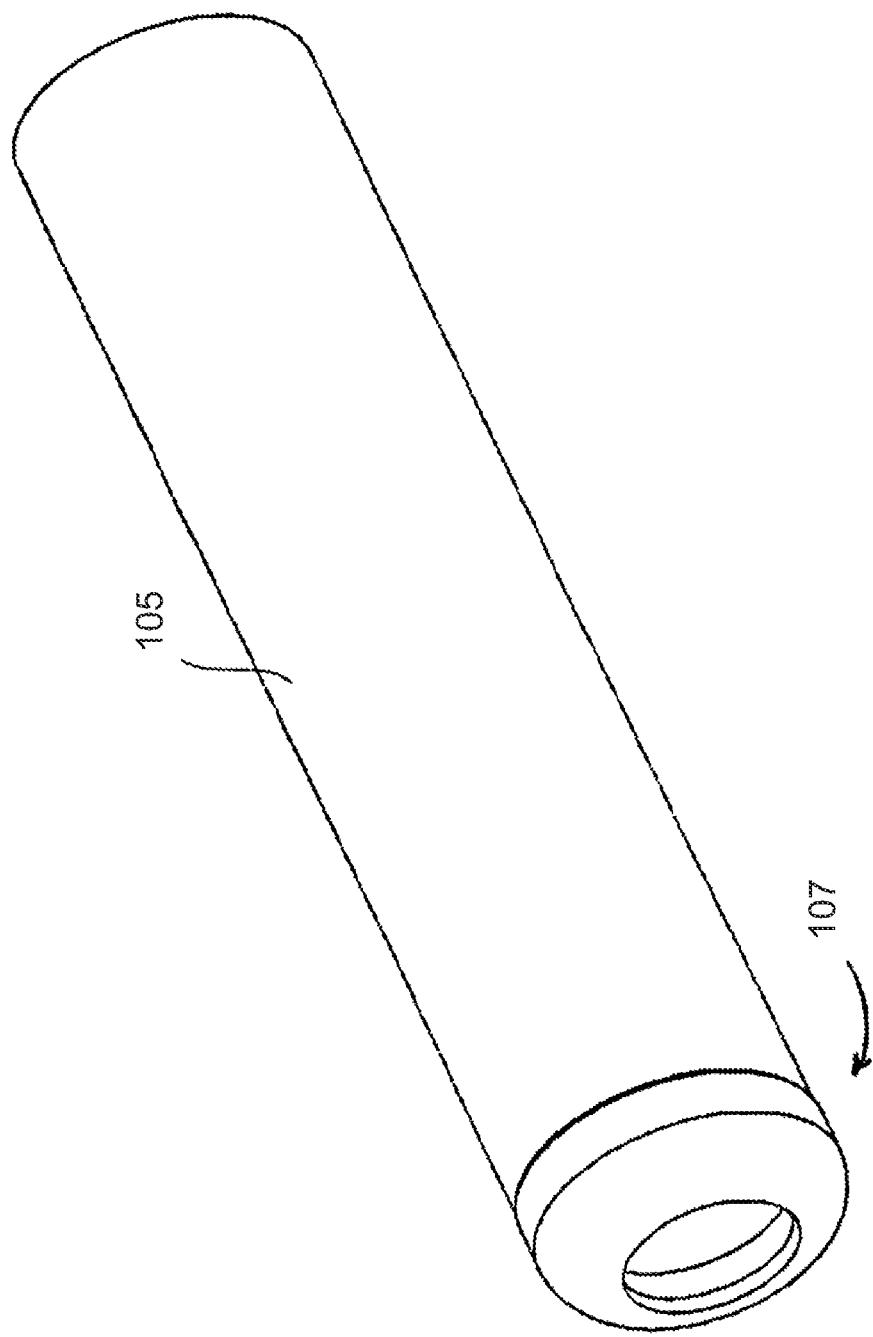
FIG. 29 is a fragmentary, perspective view of the distal tip region of the insertion device of the embodiment of FIG. 20.

The perspective view of FIG. 29 illustrates the insertion device 100 in the region of the tip 107, including the outer jacket 105 extending to the tip, which is not shown in the other figures.

Figure 30:
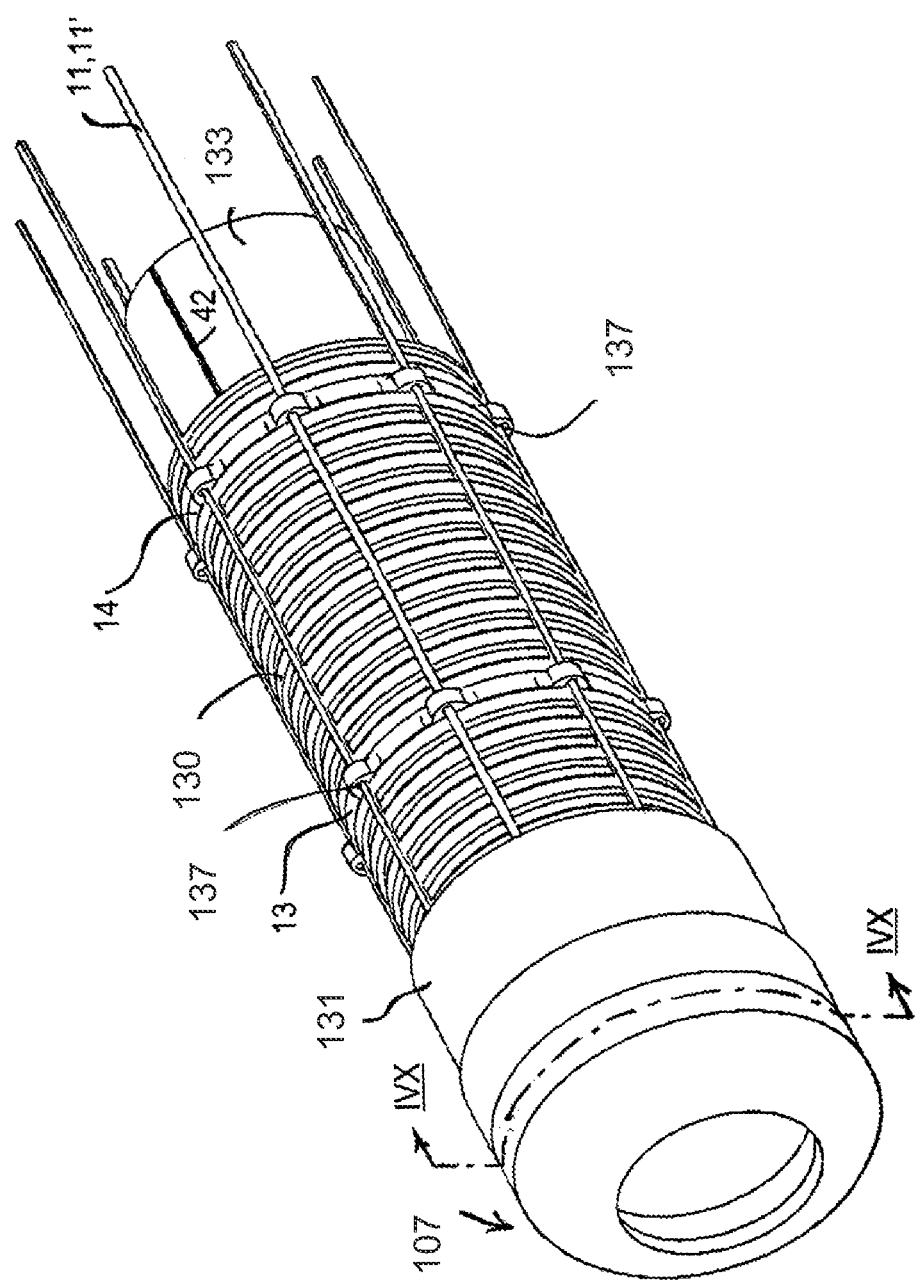
FIG. 30 is a fragmentary, perspective view of the distal tip region of the insertion device of the embodiment of FIG. 20 in which the outer jacket has been removed to show the tendons, the vertebrae and the corrugations.

The fragmentary, perspective view of FIG. 30 illustrates the insertion device 100 in the region of the tip 107, with the outer jacket removed to reveal the termination bushing 131 at the tip 107, the corrugated tube 130, the vertebrae 13, 14, the tendons 11 or 11' and the inner liner 133. It is seen that the tendons slide through channels 137 in the vertebrae.

Figure 31:
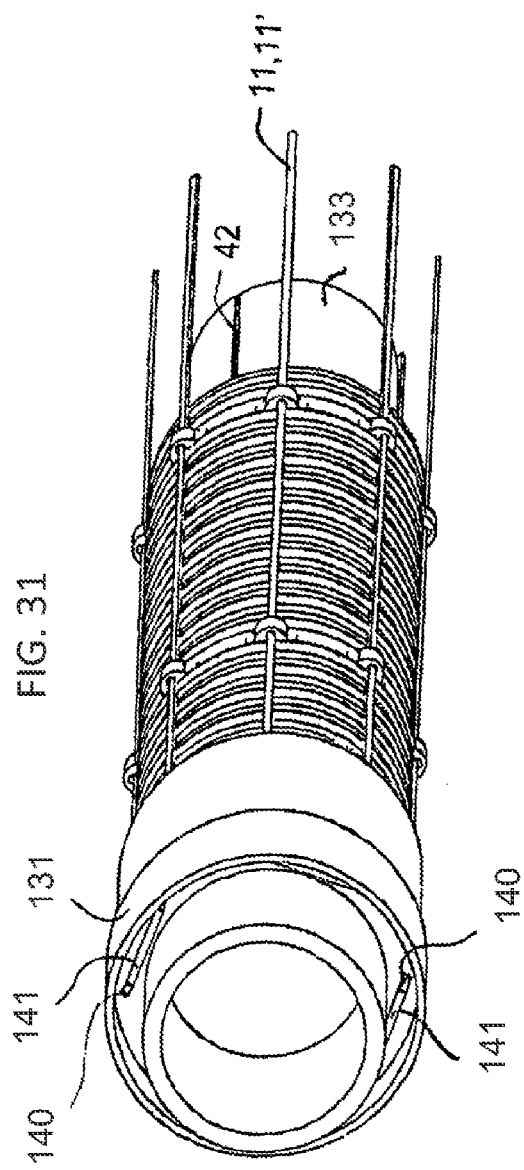
FIG. 31 is a view of the insertion device similar to FIG. 30, in which the tip has been removed.
Figure 31A:
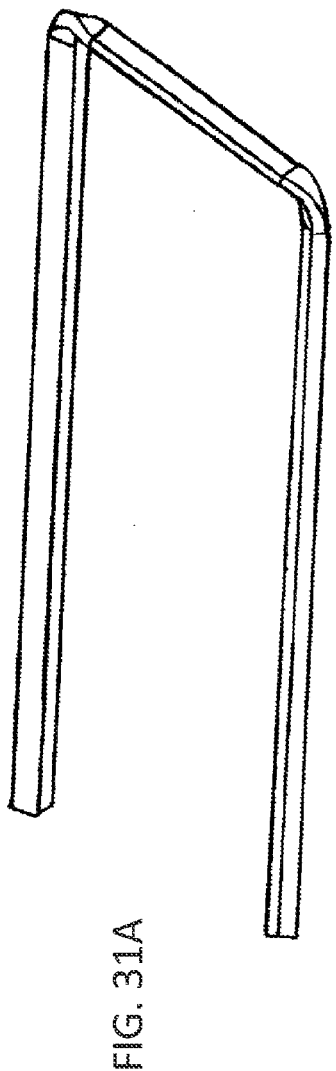
FIG. 31A is an enlarged, perspective view of a U-shaped tendon.

In FIG. 31, not only the outer jacket 105 but also the tip 107 have been removed to show how the tendons 11, 11' are anchored in the termination bushing 131. As can been seen, each tendon 11, 11' passes through a respective hole 140 in the termination bushing 131. Each two tendons together have a U-shape in the form of a large staple having a crosspiece 141 extending between two of the holes 140. This avoids the necessity of welding ends of tendons to a terminating vertebra or ring. The U-shaped tendons and crosspiece are best seen in FIG. 31A.

In FIG. 32, not only the outer jacket 105 and the tip 107 but also the termination bushing 131 have been removed to show a portion of the inner liner 133 which is sealed on the inner surface of the termination bushing 131 for vacuum sealing and smooth movement of the instrument or scope 44. The crosspieces 141 of the tendons 11, 11' as well as the seam 42 of the inner liner are also clearly shown.

FIG. 33 is a cross-sectional view of the insertion device 100 which is taken through the flexible tip restrictor 132, as seen in the direction of the vertebra 13. Therefore, the outer jacket 105, the vertebra 13 with the tendons 11, 11', the corrugated tube 130 with the peaks and valleys and the tip restrictor 132, can be seen.

Figure 34:
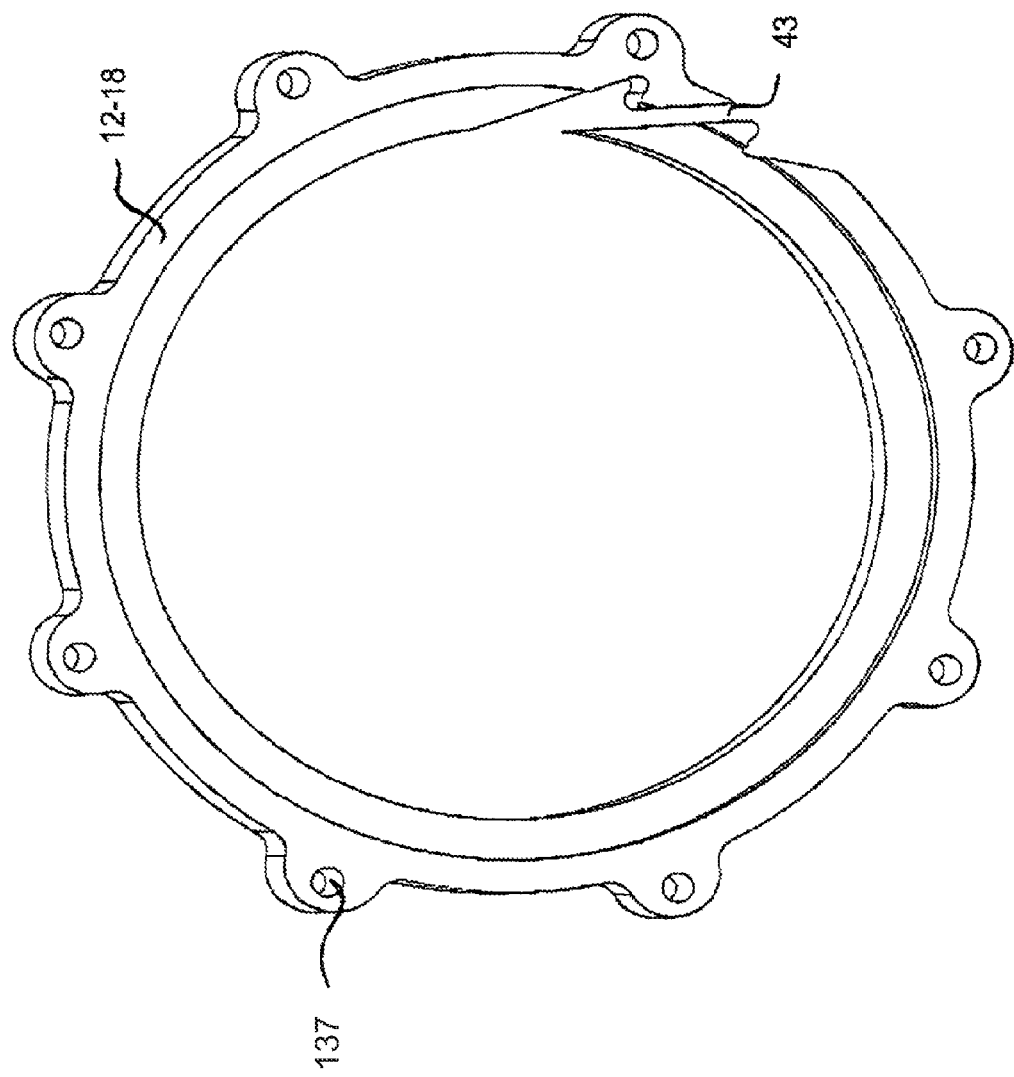
FIG. 34 is a further enlarged, perspective view of a snap vertebra of the insertion device.
Figure 35:
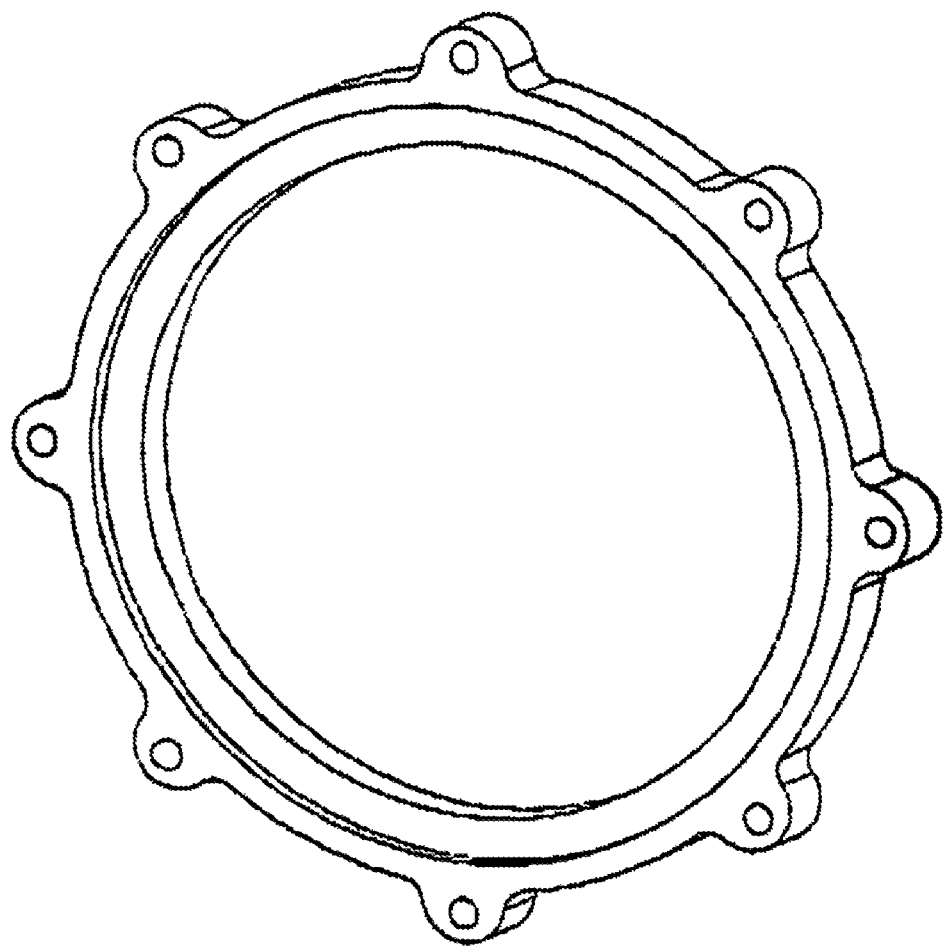
FIG. 35 is a perspective view of a continuous vertebra of the insertion device.

Representative vertebrae 12-18 are shown in FIGS. 34 and 35. The vertebra of FIG. 34 is a so-called latch ring constructed for snap installation. The vertebra is formed of elastic material which permits it to be expanded at a parting line and opened at a gap 43, so that it can be snapped over the corrugated tube 130 between two peaks thereof. Therefore, the vertebra can be installed at any location desired along the corrugated tube for support of the tendons. The vertebra shown in FIG. 35 is intended to be placed at an end of the corrugated tube 130, where no expansion and snapping into place are required.

The operation of the variably flexible insertion device 100 will now be described below by making reference to the above-described figures. If the steerable embodiment is used, the device 100 is flexed against the stiffness of the corrugated tube 130, for example upon traversing the rectosigmoid junction, by sliding one or more of the knobs 136. In either the steerable or non-steerable embodiment, if it is desired to maintain that flexed condition for guiding an endoscope, such as a colonoscopy, vacuum is applied at the connection or nipple 135. When suction is applied to create the vacuum, it causes the inner sleeve 133 and the outer jacket 105 to approach each other with the corrugated tube 130 and the tendons 11, 11' sandwiched and frictionally locked therebetween. Therefore, the vacuum connection or nipple 135 acts as a device for transitioning the hollow body 104, 107, 119, 105, 133, 130 between a relatively flexible condition and a relatively stiff condition through the application of a vacuum. As long as the vacuum is applied, the device 100 maintains its flexed condition. The positions of the knobs 136 in FIGS. 20, 21, 23 and 24 show that in the flexed condition, the tendons 11' at the outer periphery of the bend become shorter and the tendons 11' at the inner periphery of the bend become longer, since they are all fixed in place at the termination bushing 131.

The tendons or wires are passive elements which are not in tension at any time. The tendons float within the hollow body when it is in the flexible condition, except where they are fixed to termination vertebrae or the termination bushing 31 at the distal end. The tendons are frictionally locked by the inner sleeve 133 and the outer jacket 105 when the hollow body is in the stiff condition. However, in both the relatively flexible condition and the relatively stiff condition, the tendons have no active control imposed on them and are not pulled or constrained.

When it is desired to resume flexibility of the device 100, the vacuum is vented or replaced by air at ambient or positive pressure. This causes the inner sleeve 133 and the outer jacket 105 to release the tendons and allows the stiffness of the corrugated tube 130 to place the device 100 into its normally flexible condition.

In each surgical procedure using the device, the knobs and tendons are used to steer the insertion device within the body as needed, while the corrugated tube allows the device to be twisted as needed.

Figure 36:
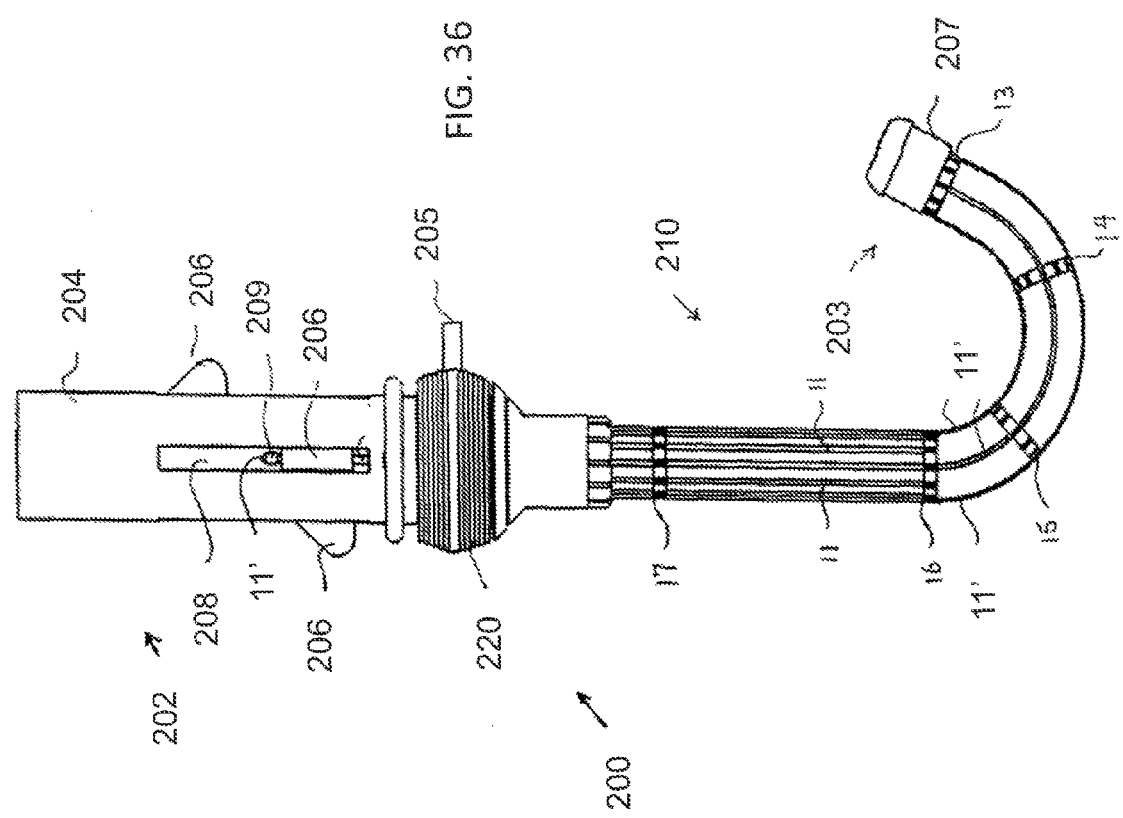
FIG. 36 is a diagrammatic, side-elevational view of a steerable, variably-flexible insertion device according to another exemplary embodiment of the invention, which has been steered to the right.
Figure 37:
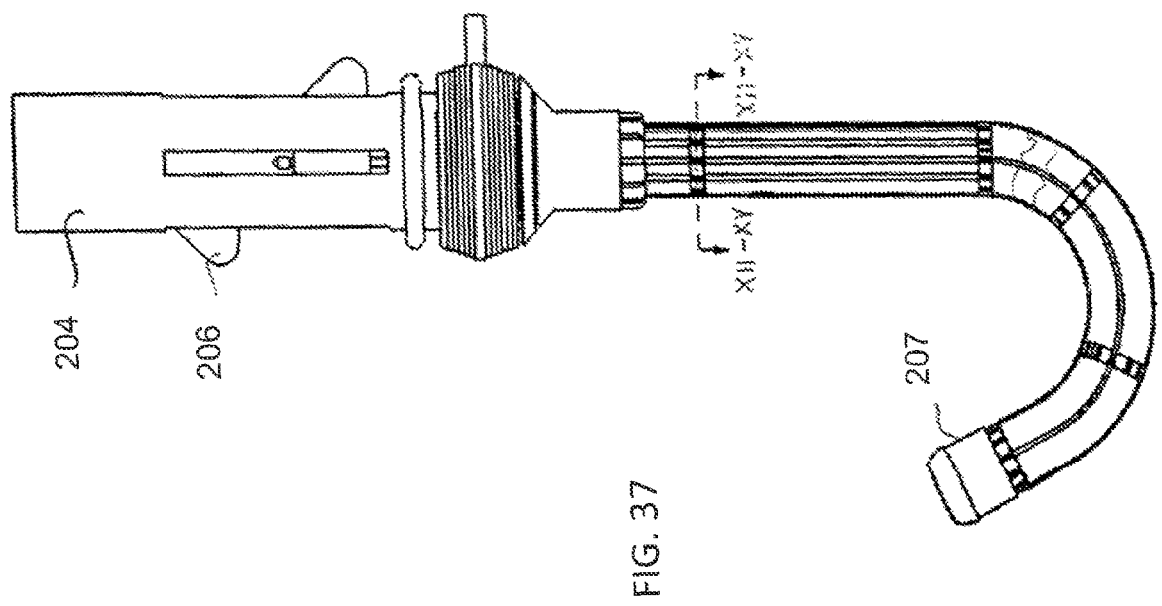
FIG. 37 is a view similar to FIG. 36, of the insertion device steered to the left.
Figure 38:
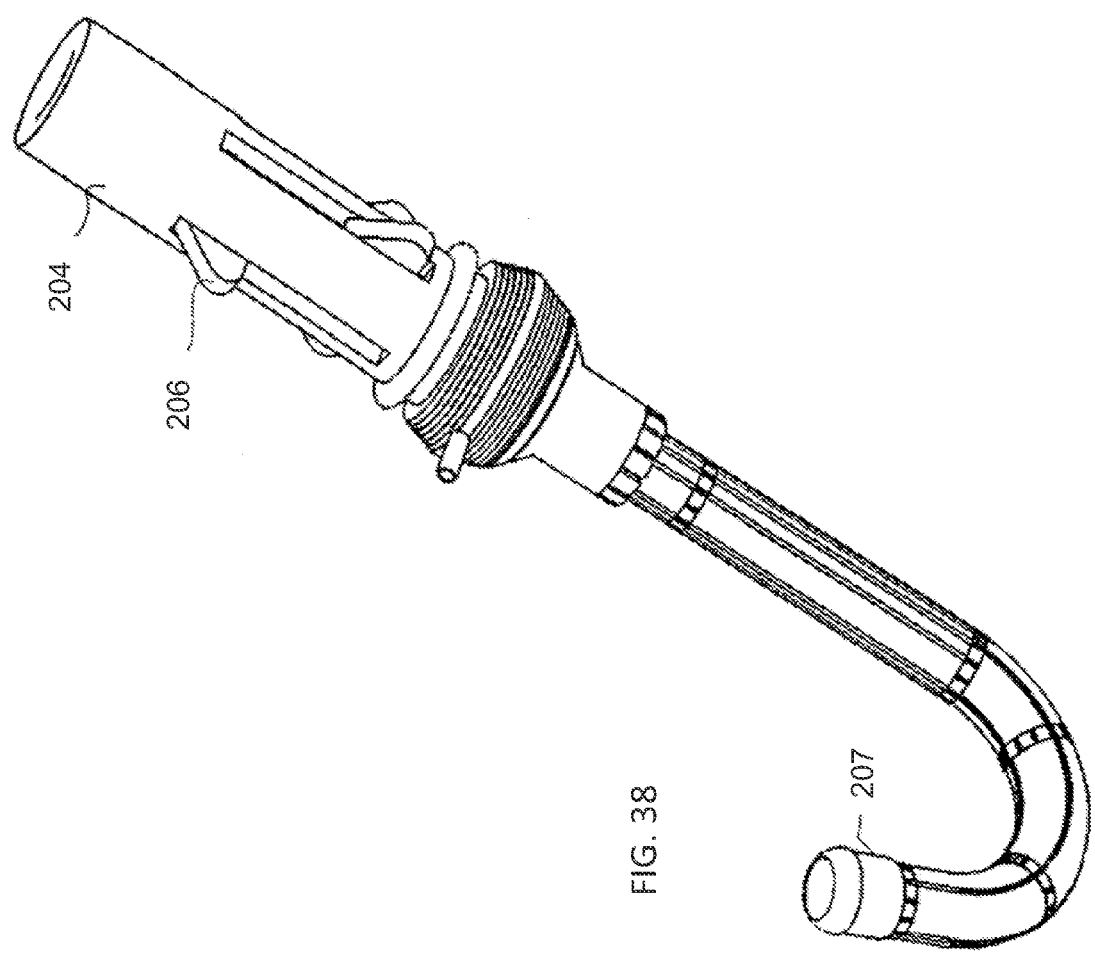
FIG. 38 is a perspective view of the insertion device of FIGS. 36 and 37.
Figure 45:
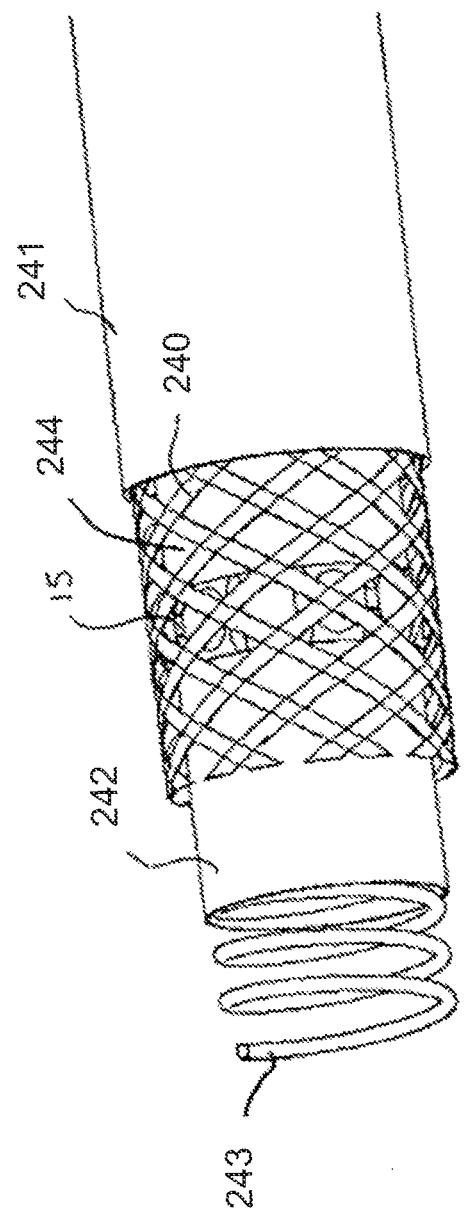
FIG. 45 is an enlarged, fragmentary, perspective view of the torque braid between an outer jacket and an inner sleeve covering a coil of the insertion device of the embodiment of FIG. 36.

Referring back to the figures of the drawings in detail and, in particular, to FIG. 36 thereof, there is seen a steerable, variably-flexible insertion device 200 according to another exemplary embodiment of the invention. The insertion device 200 has a hollow body with a proximal end 202 for manipulation by an operator and for receiving an instrument such as an endoscope or a colonoscope. The insertion device 200 also has a distal end 203 for insertion into a patient and for protrusion of the instrument. A handle 204 of the hollow body for control by the operator is disposed at the proximal end 202. The handle 204 has a vacuum connection or nipple 205 for controlling stiffness of the device, as will be explained below. An outer jacket 241 of the hollow body, which is disposed between the handle 204 and a tip 207 of the hollow body at the distal end 203, is not shown in FIG. 36. The outer jacket 241, which is shown in FIG. 45, provides a flexible section with a given length extending beyond the handle 204. Whereas FIG. 36 shows the hollow body steered to the right, FIG. 37 shows it steered to the left and FIG. 38 shows the hollow body in perspective.

A steering assembly 210 of the device 200 includes five vertebrae 13-17 shown as being disposed along the hollow body. However, more or fewer vertebrae can be provided in dependence on the length, diameter and use of the hollow body. Eight tendons are shown as being equally spaced apart about the circumference of the hollow body. A first four of those tendons, identified as non-steering tendons and indicated by reference numeral 11, extend only between the handle 204 and the vertebra 17 where they are fixed in place. A second four of those tendons, identified as steering tendons and indicated by reference numeral 11', are spaced apart by 90° circumferentially and extend between the handle 204 and the distal-most vertebra 13 where they are fixed in place. Once again, a greater or lesser number of tendons may be used, as needed. The tendons may have a rounded or flattened cross section or a flattened cross section twisted along its length. The vertebrae to which the tendons are fixed may be referred to as weld rings since the tendons may be welded thereto. For example, all of the tendons 11' are fixed to the vertebra 13, such as by welding. At the vertebra 16, for example, the steering tendons 11' are permitted to slide, but the non-steering tendons 11 are welded or otherwise fixed in place. When welding is used for fixation, the tendons and vertebrae are normally made of stainless steel. However, the tendons and vertebrae may also be formed of plastic which is bonded or adhesively connected where desired. Both metal and plastic tendons and vertebrae may be used in one device.

Figure 39:
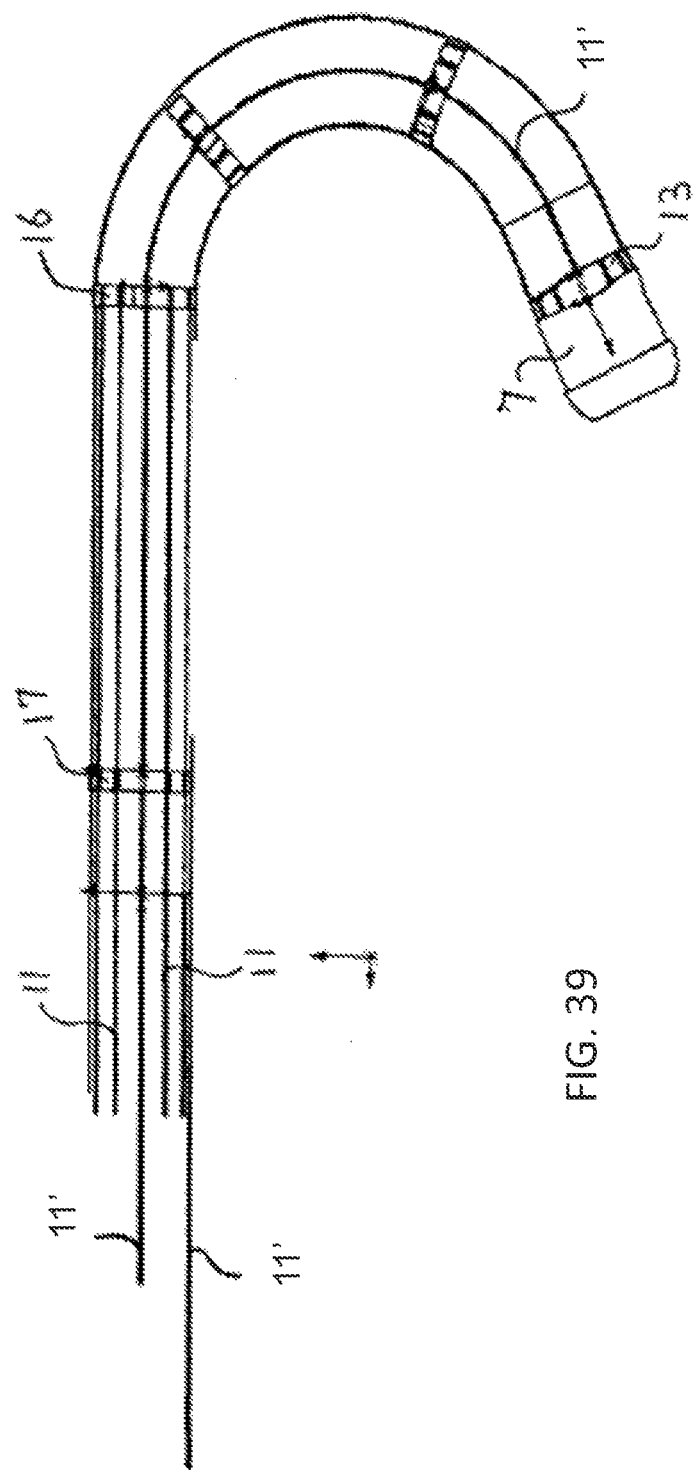
FIG. 39 is a fragmentary, side-elevational view of a steering assembly of the insertion device of the embodiment of FIG. 36.

Four knobs 206 are each slideably disposed within a respective slot 208 in the handle 204. Each of the steering tendons 11' extend between the vertebra 13 and a respective one of the knobs 206. Each steering tendon 11' extends through a respective knob 206 and is connected to a respective stop 209. When a knob 206 is slid proximally, it pushes a stop 209 and pulls a steering tendon 11' to steer the hollow body. In the condition shown in FIG. 36, the knob 206 at the right has been slid proximally so that the tip 207 of the hollow body has been steered to the right. In the condition shown in FIG. 37, the knob 206 at the left has been slid proximally so that the tip 207 of the hollow body has been steered to the left. A similar result shown in FIG. 38 has been accomplished by sliding one of the knobs 206 proximally. When the knobs 206 are forced distally, the knobs can freely slide independently of the steering tendons 11' to prevent buckling of the steering tendons 11'. It will be readily understood that if two of the knobs are slid proximally, the tip 207 will move in a direction between the two directions that each one of the knobs would have moved the tip if moved individually. FIG. 39 shows the device 200 with the handle 204 removed, from which it can be seen that the steering tendons 11' of the steering assembly continue toward the handle from the tip 207, whereas the non-steering tendons 11 stop.

Figure 40:
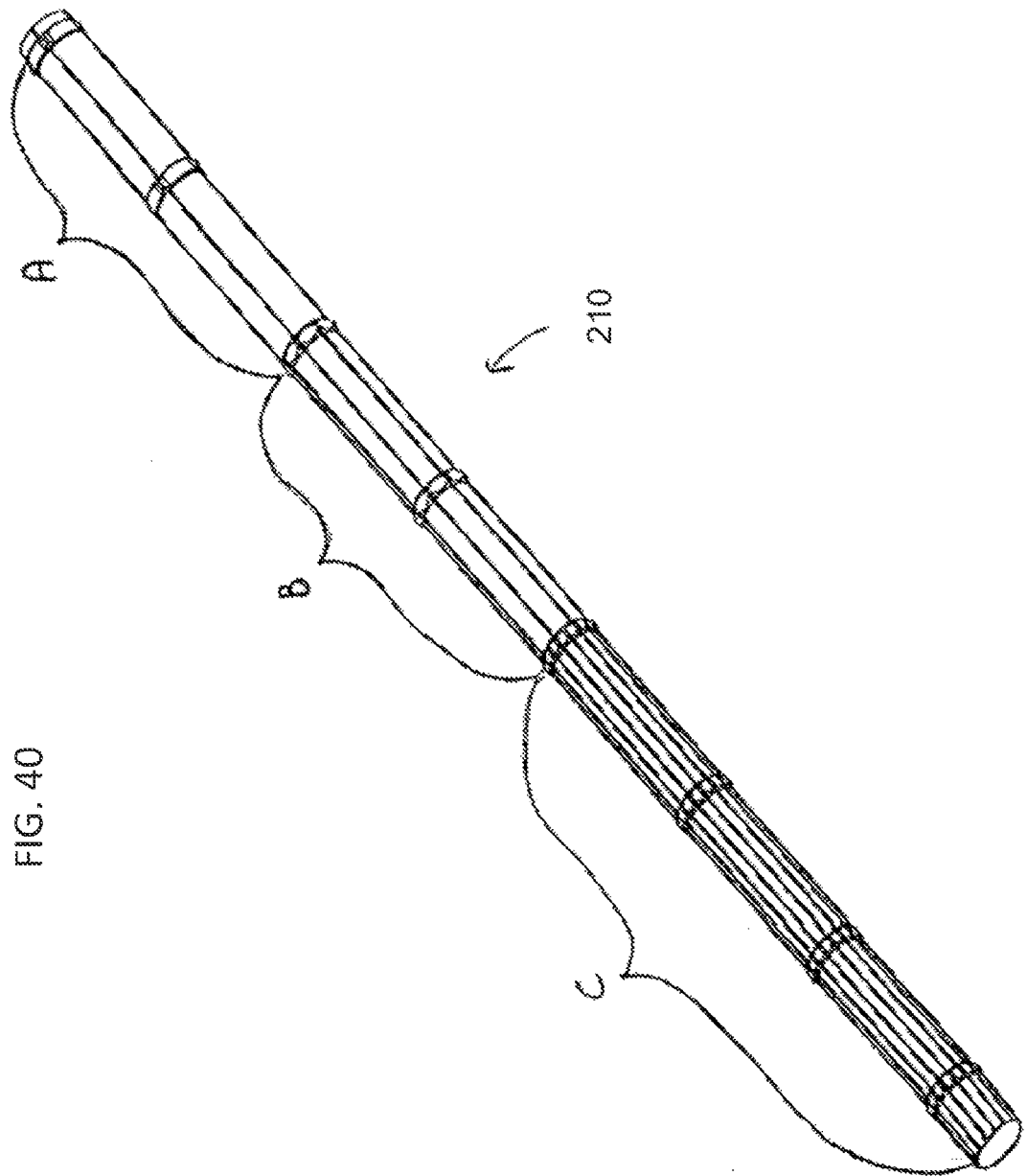
FIG. 40 is a perspective view of a stiffness zone assembly of the insertion device of the embodiment of FIG. 36.

It is also possible, as shown in FIG. 40, to provide stiffness zones within the steering assembly 210. For example, a stiffness zone A closest to the distal tip 207 has four tendons, a stiffness zone B has eight tendons and a stiffness zone C closest to the handle 204 has sixteen tendons. A zone with more tendons will be stiffer than a zone with fewer tendons. The number of tendons and their location within the zones as well as the number of zones can be increased or decreased, depending on the application of the device. The vertebrae are also shown. The four tendons in the zone A are all fixed at the upper most vertebra but are free to slide elsewhere. Four of the eight tendons in zone B, which do not extend to zone A, are fixed at the vertebra between zones A and B but are free to slide elsewhere. Similarly, eight of the sixteen tendons in zone C, which do not extend into zones A and B, are fixed at the vertebra between zones B and C but are free to slide elsewhere.

Figure 41:
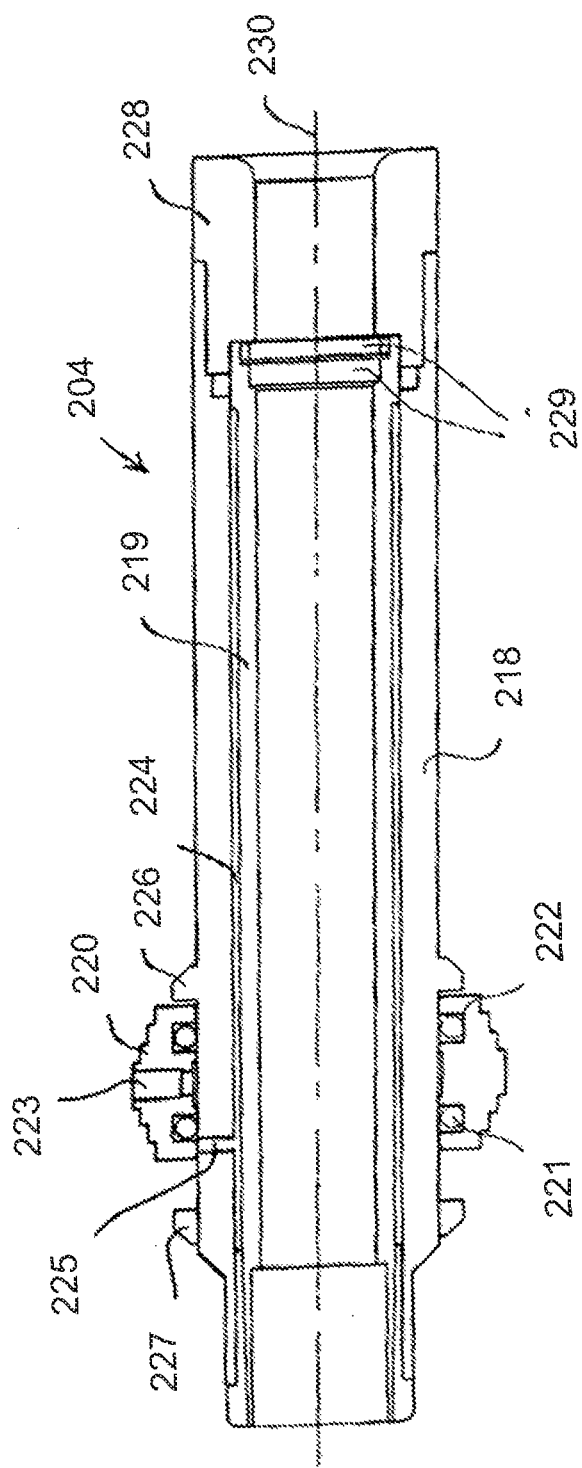
FIG. 41 is a longitudinal-sectional view of a sliding tire valve and side tube assembly of the insertion device of the embodiment of FIG. 36.

FIG. 41 shows a cross-sectional view of the handle 204 of FIGS. 36-38, in which the connection or nipple 205, knobs 206 and slots 208 are not shown. The handle 204 has an inner handle 219 disposed within an outer handle 218, defining an annular vacuum plenum volume 224 therebetween which extends in longitudinal direction of the handle 204. A vacuum inlet/outlet hole or port 225 is formed in the body of the outer handle 218 and communicates with the volume 224. A sliding so-called tire valve thumb grip 220 encircles the outer handle 218 and is sealed thereto by O-ring seals having O-rings 221 in recesses 222 in the grip 220. The grip 220 also has a vacuum inlet/outlet 223 for the connection or nipple 205. When the grip 20 is slid toward an annular stop 226 as shown, the vacuum inlet/outlet 223 is not in alignment with the vacuum inlet/outlet hole 225. However, when the grip 220 is slid toward an annular stop 227, the vacuum inlet/outlet 223 and the vacuum inlet/outlet hole 225 are aligned, providing communication between the connection or nipple 205 and the volume 224. Therefore, during operation, the grip 220 is slid toward the stop 227 to apply vacuum to stiffen the hollow body or to vent the vacuum to the atmosphere or supply air at atmospheric pressure to make the hollow body flexible again. The grip 220 is slid toward the stop 226 to maintain the stiffened or flexible condition of the hollow body attained by vacuum or venting or air supply through the connection or nipple 205.

And end cap 228 is inserted into a proximal end of the outer handle 218 for insertion of an instrument, such as an endoscope or a colonoscope. End caps with various sized openings may be used in dependence on the instrument being used. The instrument passes through the hollow body and emerges at the distal tip 207. A diaphragm seal or so-called septum 229 is disposed between the end cap 228 and the inner handle 219. A dot-dash line 230 represents an instrument inserted through the handles.

FIGS. 42 and 43 show a handle 204 with an outer vacuum valve handle 235 which is ergonomically configured with a so-called handlebar shape to be gripped by the hand of an operator of the device. A tire valve thumb grip 220 is also provided in the embodiment of FIGS. 42 and 43, but has been omitted for clarity. The outer handle 235 is an alternative to the outer handle 218. As can be seen from the cross section of FIG. 43, a vacuum source may be connected to a port 236 in the outer handle 235 and the vacuum inlet/outlet 223 of the tire valve thumb grip 220 may communicate with a vacuum inlet/outlet hole 237 leading to an annular vacuum plenum volume 239 between the outer handle 235 and an inner handle 238. When the tire valve thumb grip 220 is slid so that the vacuum inlets/outlets 223 and 237 are misaligned, vacuum is supplied from the port 236 to the vacuum plenum volume 239. When the tire valve thumb grip 220 is slid so that the vacuum inlets/outlets 223 and 237 are aligned, the plenum 239 is vented to the atmosphere. An end cap 234 is also shown.

Figure 44:
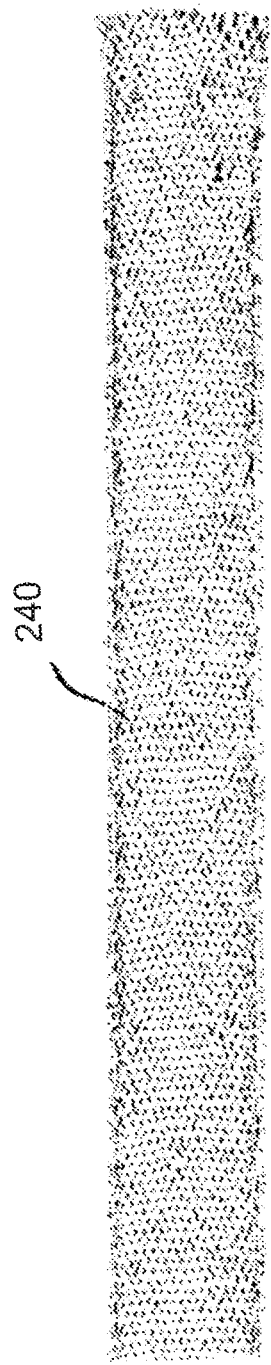
FIG. 44 is an elevational view of a torque braid of the insertion device of the embodiment of FIG. 36.

FIG. 44 illustrates a torque sheath or braided inner liner 240 of the insertion device 200. The torque braid 240 is a woven tube formed of fabric, plastic, metal or a combination thereof, such as a metallized material. Steel or a polymer, such as polyethylene terephthalate or PET (sold under the trademark MYLAR) or PEEK (polyether ether ketone) are particularly useful. The purpose of the torque braid 240 is to transmit torque applied by the operator of the device at the proximal end 202 along the length of the hollow body up to the tip 207. Therefore, the torque braid must be non-linearly compliant, that is it has a limited elongation in the linear direction.

As is shown in the perspective view of FIG. 45, the torque braid 240 may be disposed in a space 244 between an outer jacket 241 and an inner sleeve 242. In the illustrated embodiment, the torque braid 240 is disposed above the vertebra 15, but the tendons have been omitted for clarity. The torque braid 240 may be placed in various locations, as will be described below with reference to FIGS. 47-50. The purpose of the torque braid 240 is to allow twisting of the hollow body as well as steering of the hollow body by the tendons while inserting the insertion device into the body. The torque braid 240 is typically provided over the full length of the hollow body, but may also be omitted at the tip 207 for additional flexibility or doubled, for instance, near the handle 204 for additional stiffness.

FIG. 45 also shows a coil 243 of the hollow body which is provided within the inner sleeve 242 of the hollow body for supporting the inner sleeve. The coil may be a wire which is TEFLON- or hydrophilic-coated to ease insertion of an endoscope or colonoscope. The stiffness or spring constant k of the coil 243 tends to maintain the device 200 in a straight condition and is used to maintain the round cross section of the device 200 while it is flexed.

Figure 46:
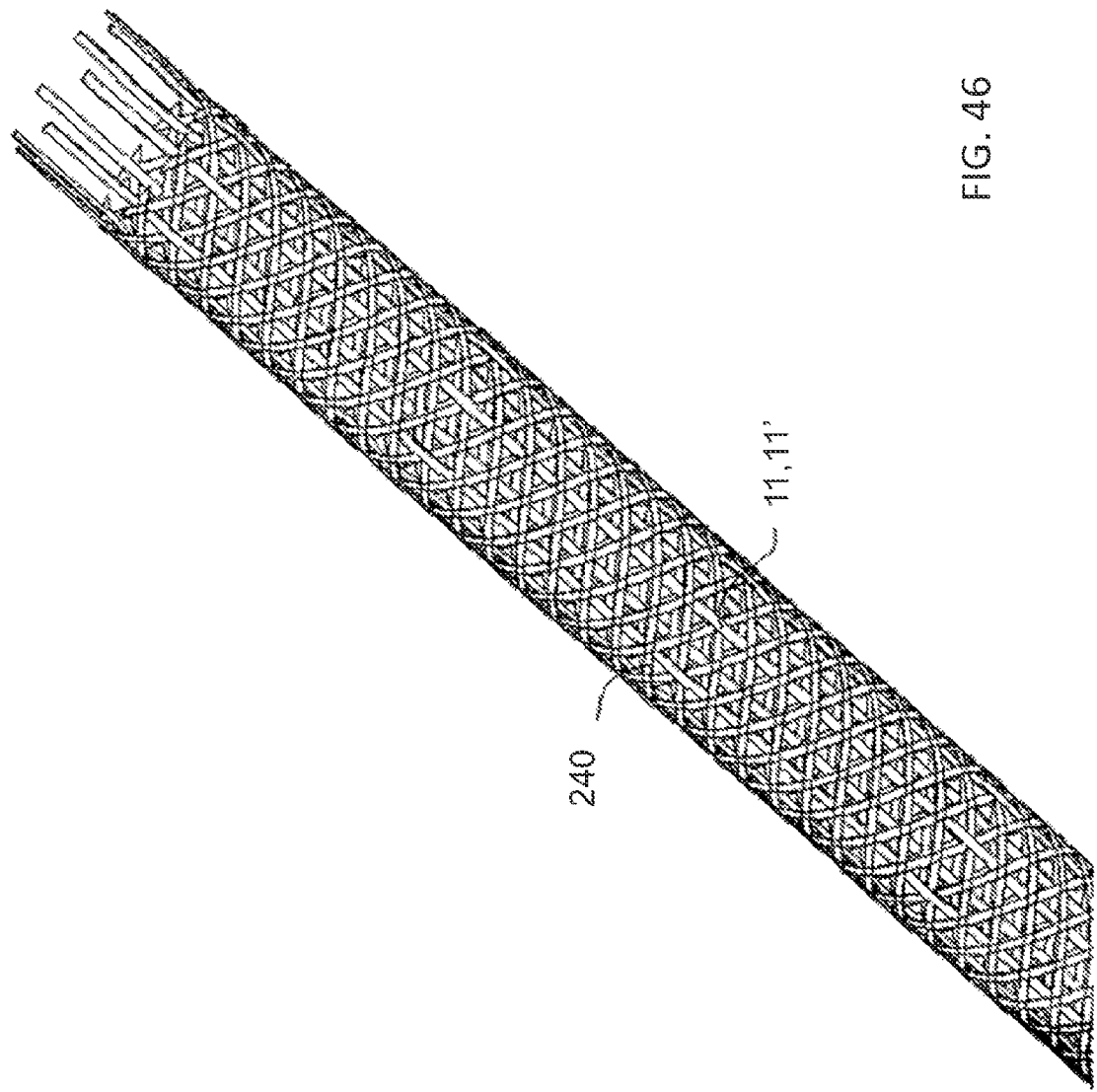
FIG. 46 is a fragmentary, perspective view showing tendons intermittently woven through the torque braid.

FIG. 46 shows an alternative embodiment of the torque braid 240 and the tendons 11, 11', in which the tendons are intermittently woven through the torque braid to eliminate the need for the vertebrae 13-17. The tendons 11, 11' travel under the torque braid 240 for about 2 inches and then are woven through one loop of the torque braid 240 to create weave points. This is repeated along the length of the device. The weave points act like the vertebrae in "attaching" the tendons 11, 11' to the body of the device but letting the tendons slide through. Using the torque braid in this way eliminates the need for the vertebrae thus decreasing the outer diameter of the device, lowering the cost of the device and simplifying the structure thereof. It is noted that the tendons are shown as being flexed as they weave through the torque braid for clarity of the illustration. In actuality there will be some amount of flex in both the torque braid and the tendons, but mostly on the part of the torque braid. The tendons could also be woven in the opposite way, that is laid on top of the braid and woven down into it.

FIGS. 47-50 are cross-sectional views of the device, in which the torque braid 240 is placed in various locations. In each of the figures, as seen from the exterior toward the interior, the insertion device 200 includes the outer jacket 241, the space 244, the vertebrae 13-17 (reference numeral 15 is used as an example), the inner sleeve 242 and the coil 243, although the latter is merely shown in outline form for the sake of clarity. It is also seen that the vertebrae 13-17 have channels 245 formed therein permitting movement of the tendons 11, 11' which are not fixed in place.

Figure 47:
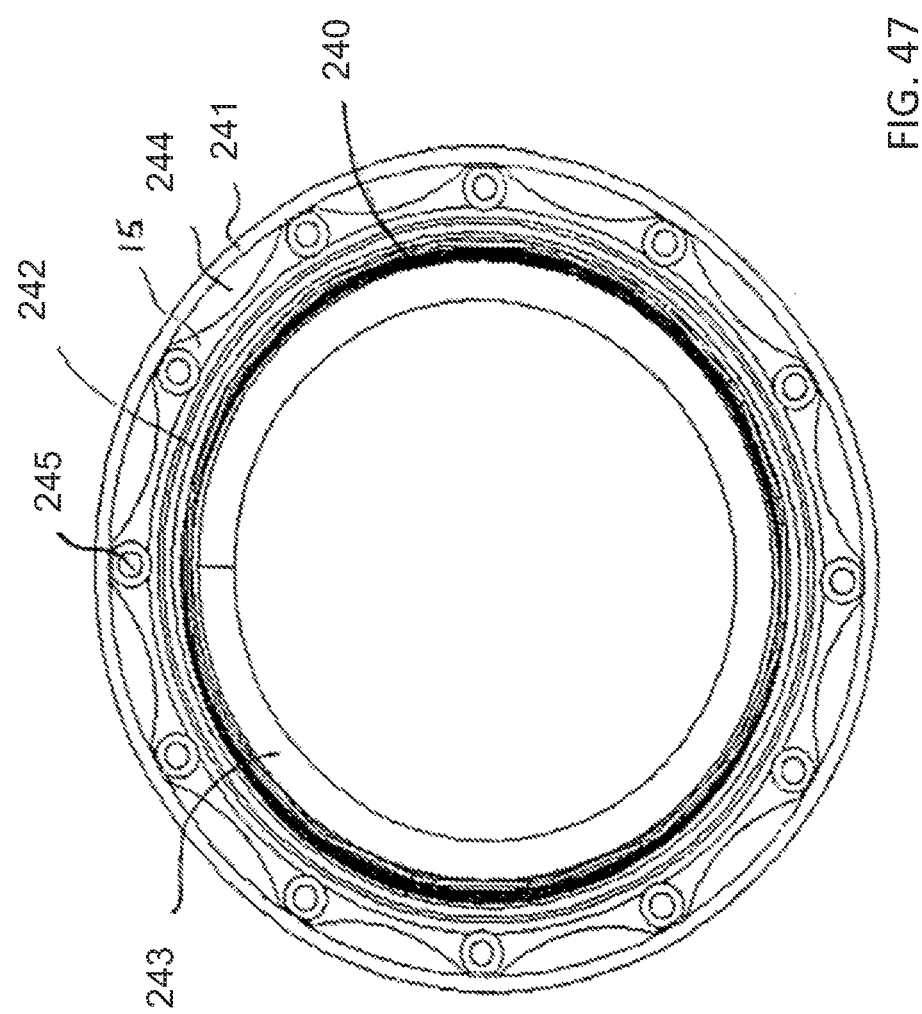
FIGS. 47, 48, 49, and 50 are cross-sectional views of the insertion device, which are taken along a line XII-XV of FIG. 37, in the direction of the arrows, but with the torque braid in various locations.
Figure 48:
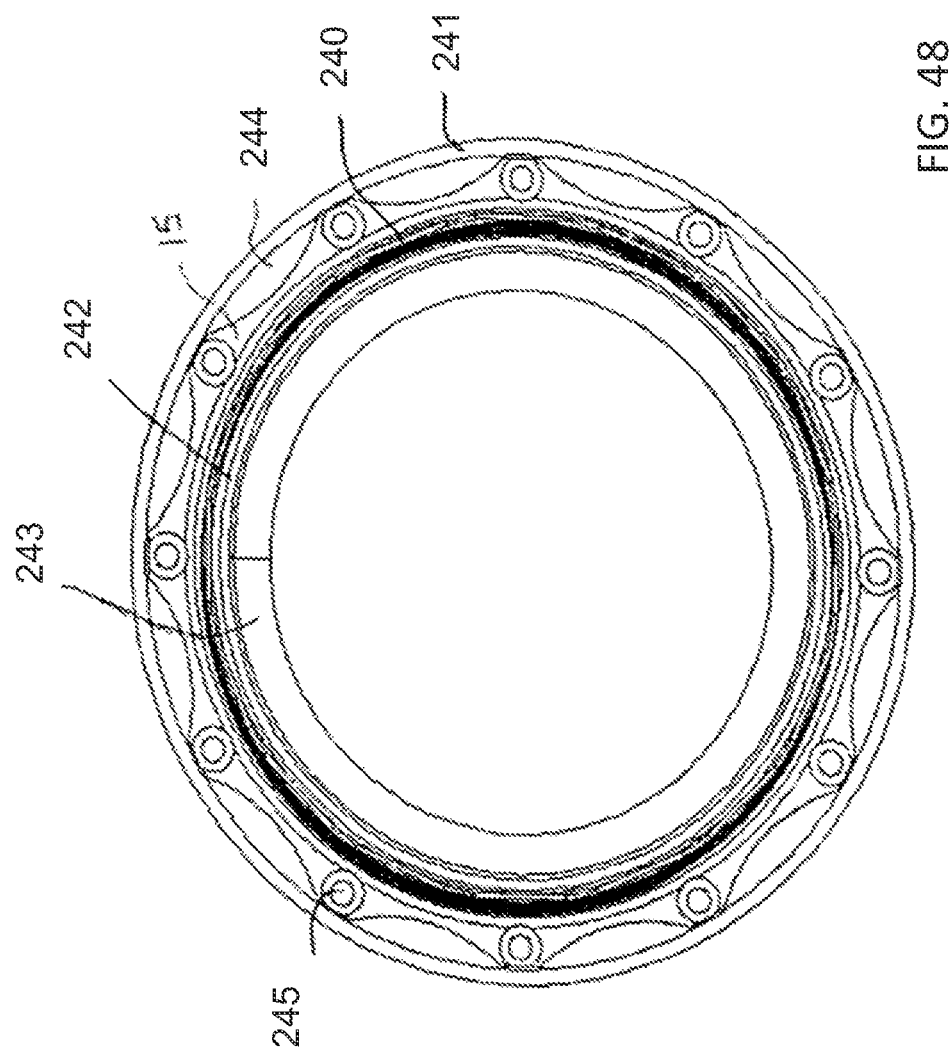
Figure 49:
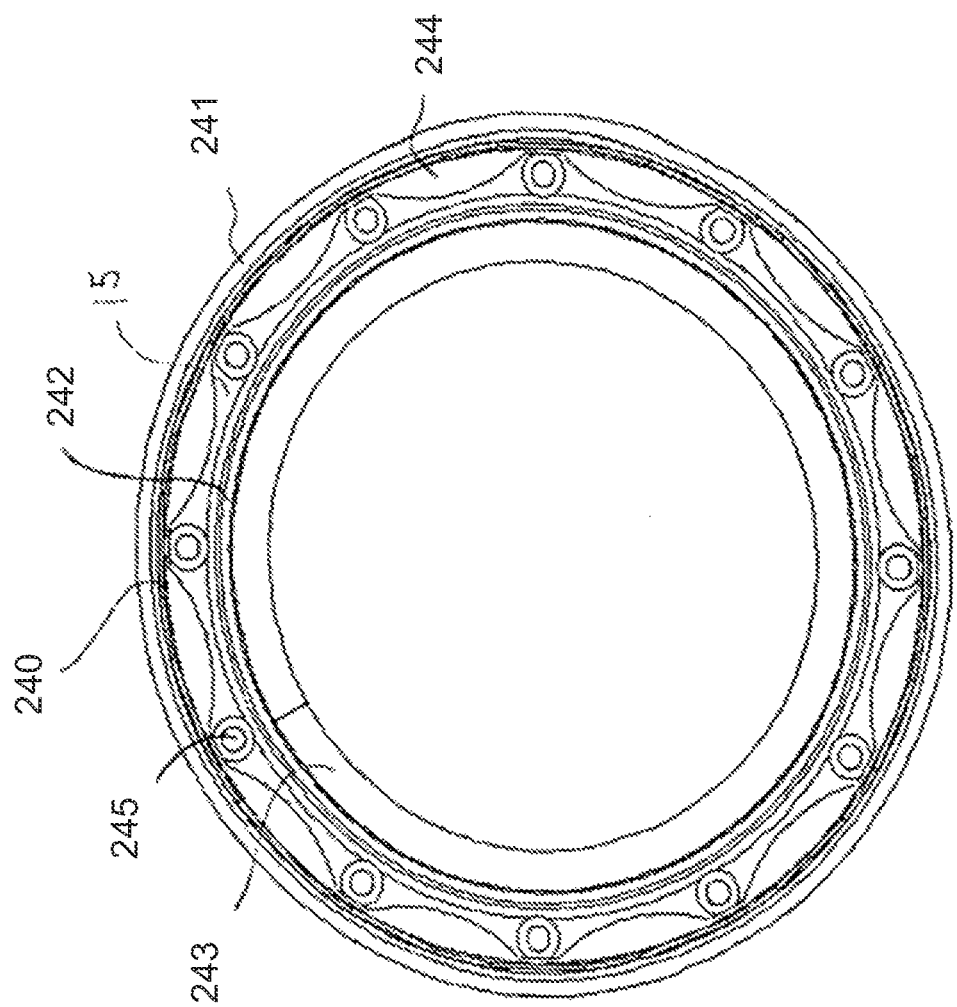
Figure 50:
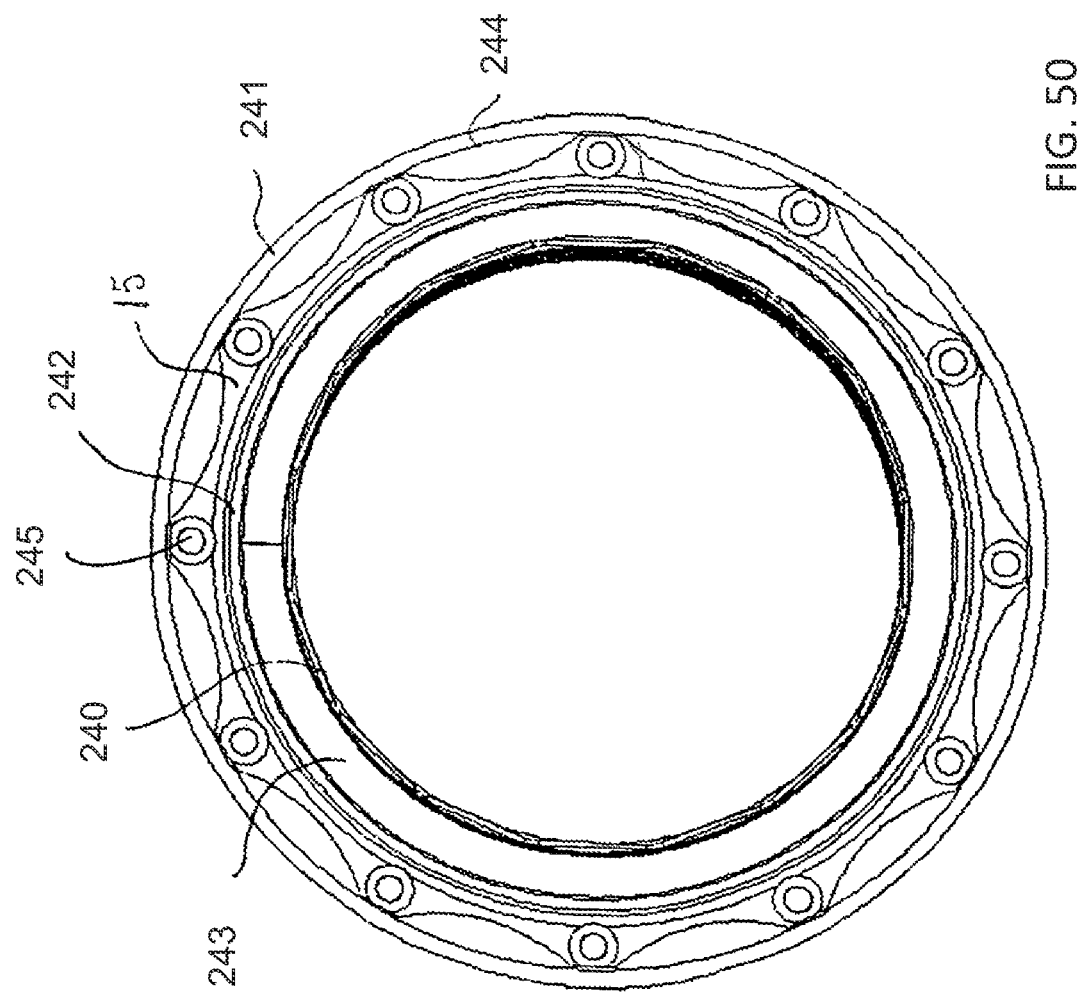

In the embodiment of FIG. 47, the torque braid 240 is disposed between the coil 243 and the inner sleeve 242. In the embodiment of FIG. 48, the torque braid 240 is disposed between the inner sleeve 242 and the vertebra 15. In the embodiment of FIG. 49, the torque braid 240 is disposed between the vertebra 15 and the outer jacket 241. In the embodiment of FIG. 50, the torque braid 240 may be disposed within the coil 243.

The operation of the variably flexible insertion device 200 will now be described below by making reference to the above-described figures. The device 200 is flexed against the stiffness or spring constant k of the coil 243, for example upon traversing the rectosigmoid junction, by sliding one or more of the knobs 206. If it is desired to maintain that flexed condition for guiding an endoscope, such as a colonoscope, vacuum is applied at the connection or nipple 205 in the embodiment of FIG. 41 or at the vacuum port 236 in the embodiment of FIG. 43. When suction is applied to create the vacuum, it causes the inner sleeve 242 and the outer jacket 241 to firmly contact each other with the tendons 11, 11' sandwiched and frictionally locked therebetween. Therefore, the vacuum connection or nipple 205 or the vacuum port 236 acts as a device for transitioning the hollow body 204/235, 207, 219/238, 241, 242, 243 between a relatively flexible condition and a relatively stiff condition through the application of a vacuum. As long as the vacuum is applied, the device 200 maintains its flexed condition. The positions of the knobs 206 in FIGS. 36-38 show that in the flexed condition, the tendons 11' at the outer periphery of the bend become shorter and the tendons 11' at the inner periphery of the bend become longer, since they are all fixed in place at the first vertebra 13.

The tendons or wires are passive elements which are not in tension at any time. The tendons float within the hollow body when it is in the flexible condition, except where they are fixed to vertebra, such as at the distal end. The tendons are frictionally locked by the inner sleeve 242 and the outer jacket 241 when the hollow body is in the stiff condition. However, in both the relatively flexible condition and the relatively stiff condition, the tendons have no active control imposed on them and are not pulled or constrained.

When it is desired to resume flexibility of the device 200, the vacuum is vented or replaced by air at ambient or positive pressure. This causes the inner sleeve 242 and the outer jacket 241 to release the tendons and allows the stiffness or spring constant k of the coil 243 to place the device 200 into its normally flexible condition.

In each surgical procedure using the device, the knobs and tendons are used to steer the insertion device within the body as needed, while the torque braid allows the device to be twisted as needed.

Referring back to the figures of the drawings in detail and, in particular, to FIGS. 51 and 52 thereof, there is seen a torque-transmitting, variably-flexible, locking insertion device 300 according to the invention having a working length. The insertion device 300 has a hollow body with a proximal end 302 for manipulation by an operator and for receiving an instrument 340 such as an endoscope or a colonoscope, shown in FIG. 63. The insertion device 300 also has a distal end 303 for insertion into a patient and for protrusion of the instrument. A handle 304 of the hollow body for control by the operator is disposed at the proximal end 302. An outer jacket or sleeve 305 of the hollow body extends to a tip 306, which may be formed of rubber, at the distal end 303. As will be explained below, the handle 304 has an end cap 308, an actuator or bobbin 309 for locking an instrument, a sliding valve or slider 310 and a forward stop 311. The handle 304 also has a vacuum connection or nipple 312 for controlling stiffness of the device, as will be explained below as well. A corrugated tube 315 in the region of the distal tip 306, which is illustrated in other figures, extends to the coupler 335.

Figure 54:
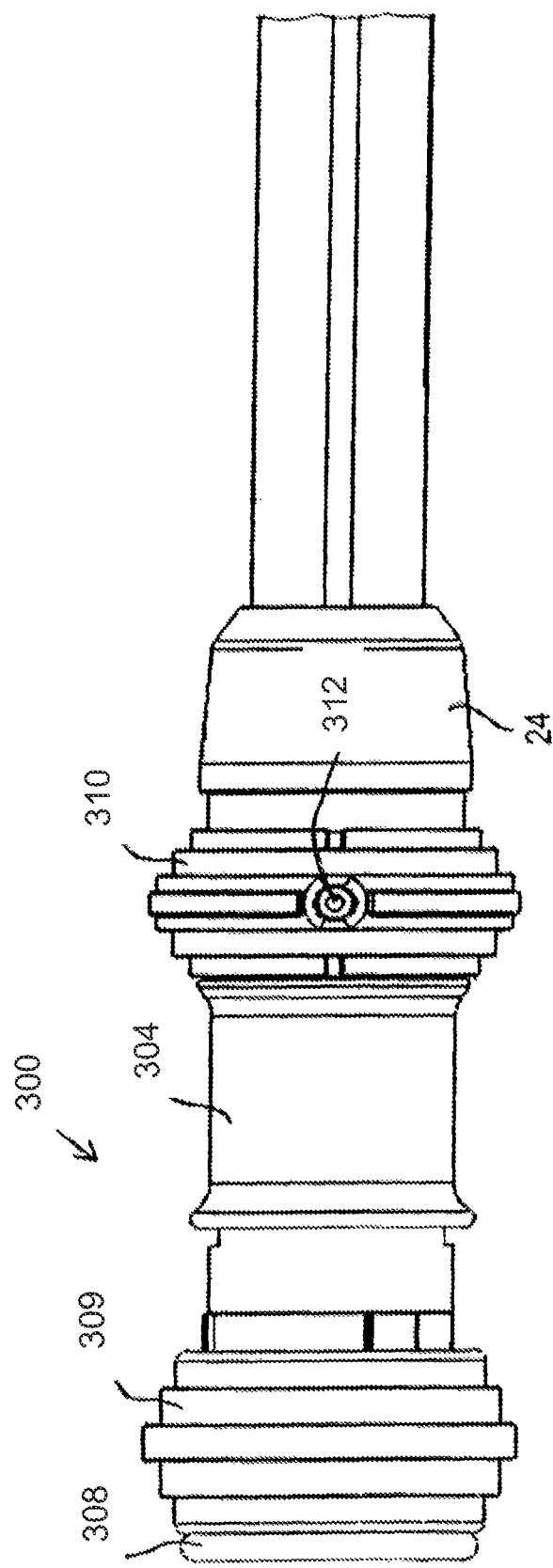
FIG. 54 is a fragmentary, further enlarged, top-plan view of the proximal end of the insertion device of the embodiment of FIG. 51.
Figure 55:
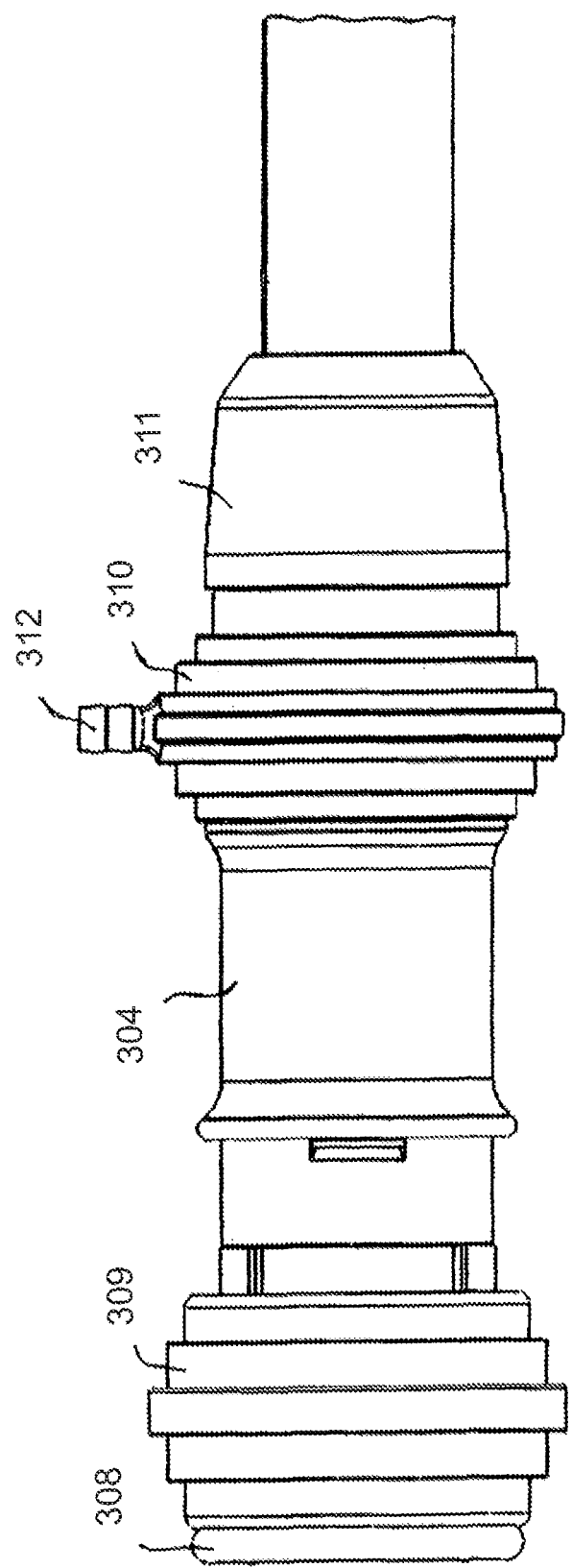
FIG. 55 is an even further enlarged, fragmentary, side-elevational view of the proximal end of the insertion device of the embodiment of FIG. 51.

FIGS. 53, 54 and 55 are enlarged perspective, top and side views showing the insertion device 300, from which the end cap 308, the actuator or bobbin 309, the handle 304, the sliding valve or slider 310 with the nipple 312, the forward stop 311 and the strain relief retainer, can be seen more clearly. FIG. 53 also shows the outer jacket 305 and the distal tip 306.

Figure 56:
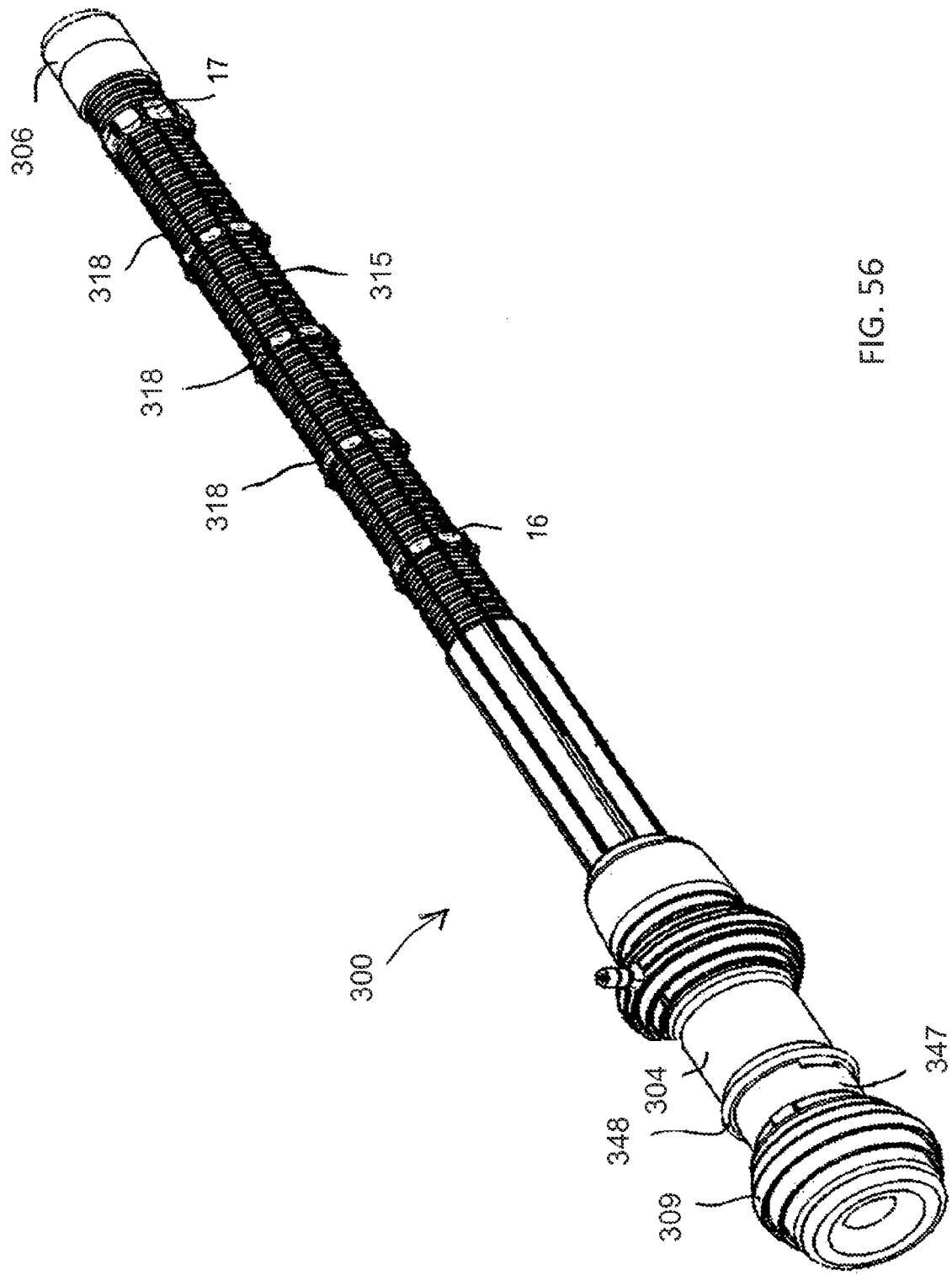
FIG. 56 is a perspective view of the insertion device of the embodiment of FIG. 51 with an outer jacket removed.
Figure 57:
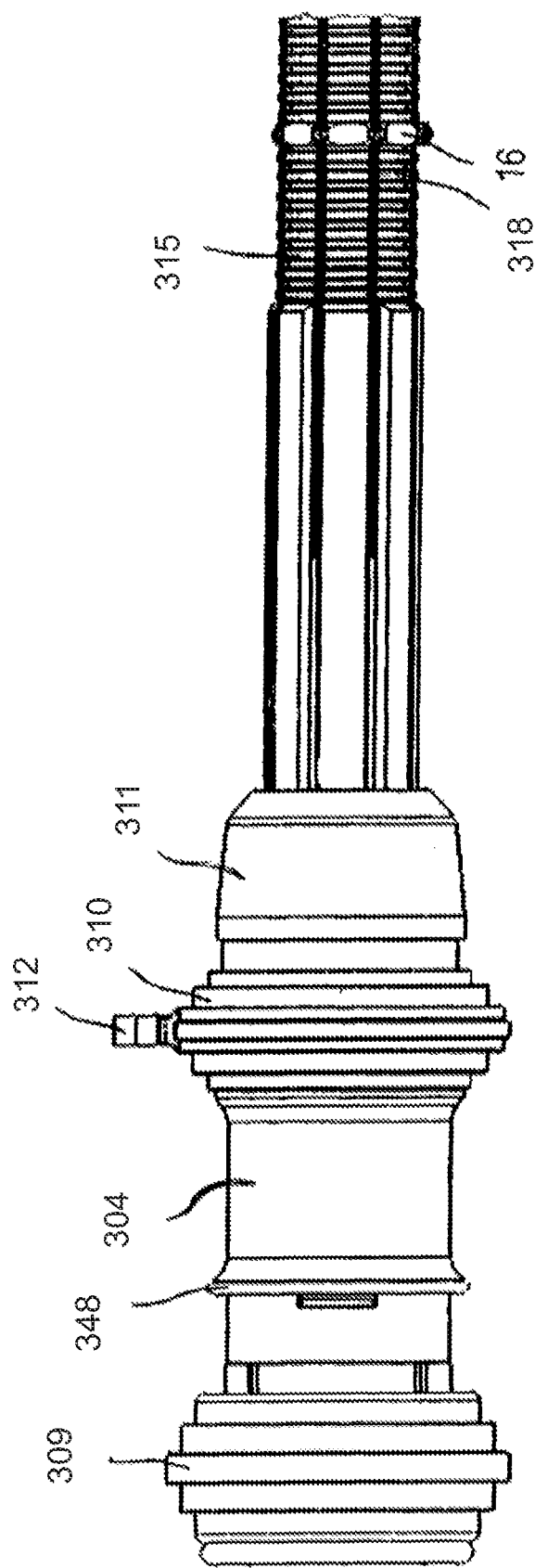
FIG. 57 is a fragmentary, enlarged, side-elevational view of the proximal end and part of the working length of the insertion device with the outer jacket removed.
Figure 59A:
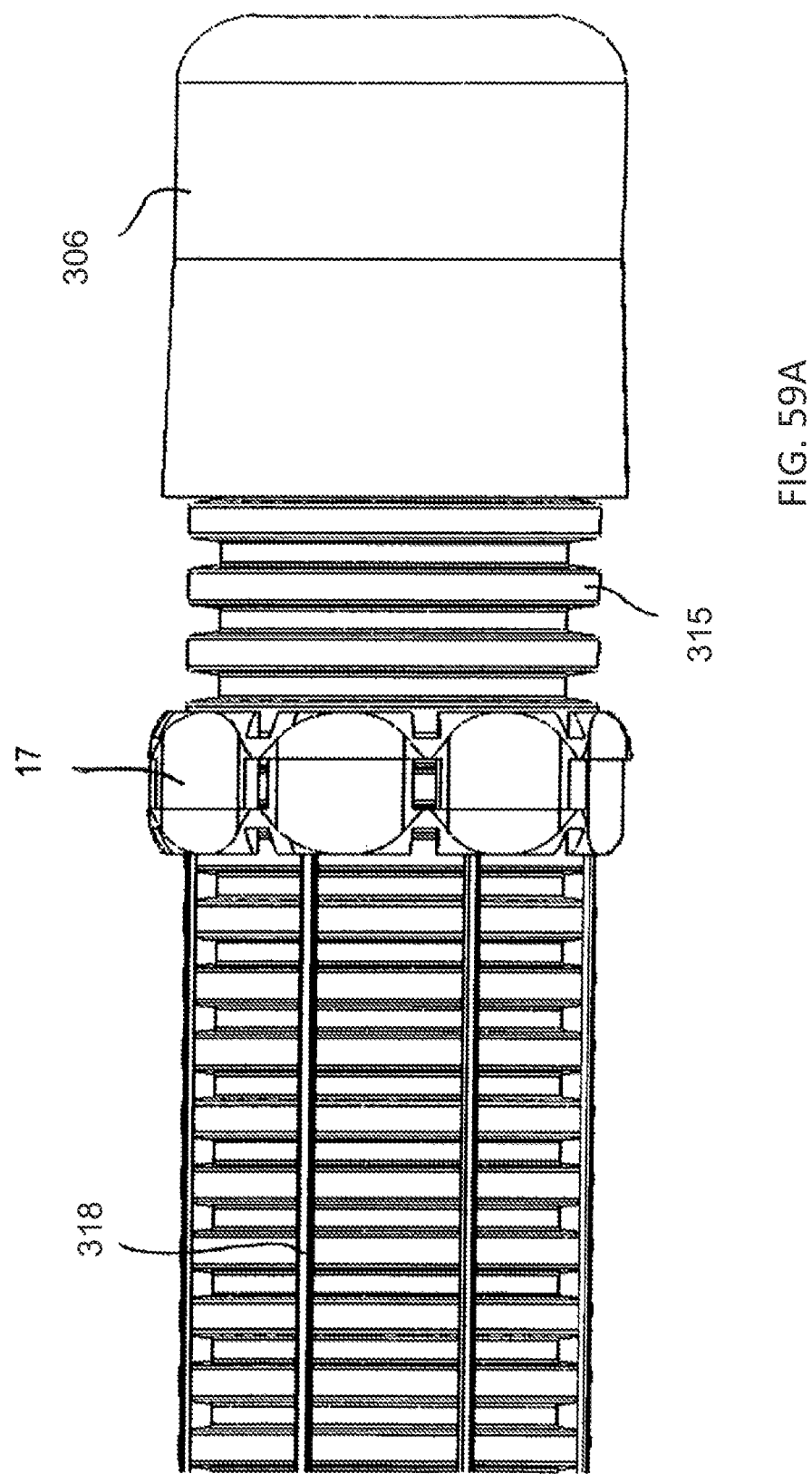
FIGS. 59A and 59B are even further enlarged, fragmentary, elevational views of a distal end of the insertion device in which a locking ring is respectively shown and omitted for clarity and in which the outer jacket has been removed.
Figure 59B:
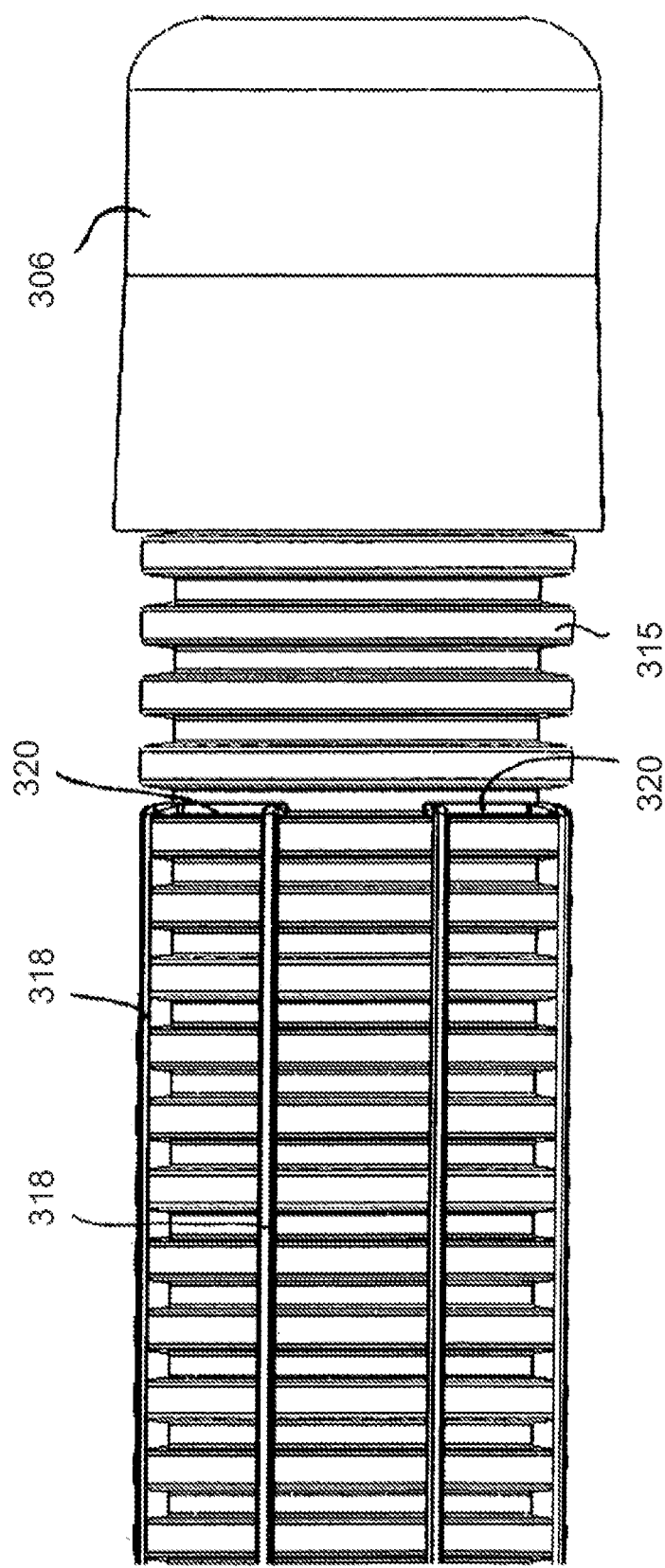
Figure 60B:
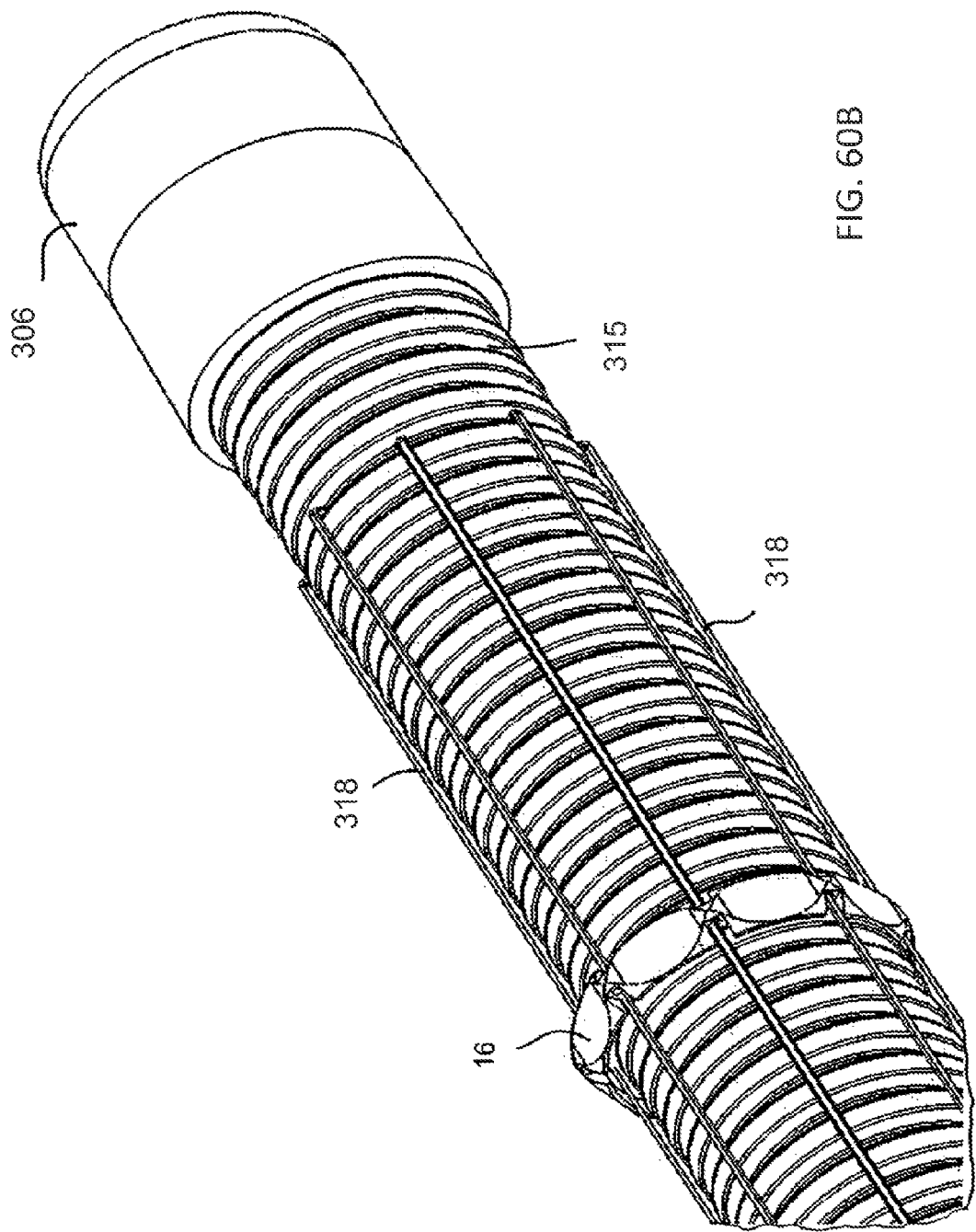
Figure 61A:
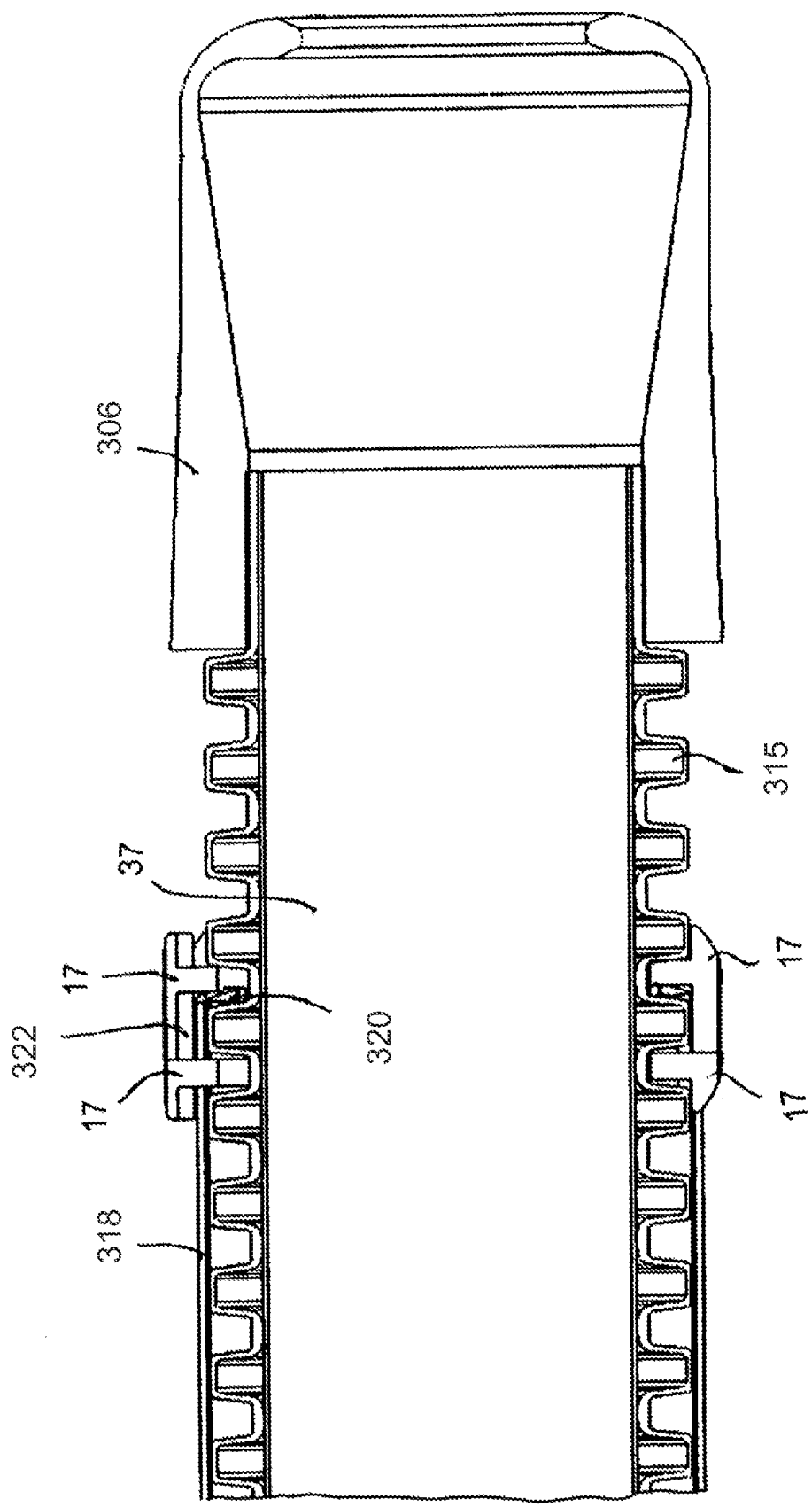
Figure 61C:
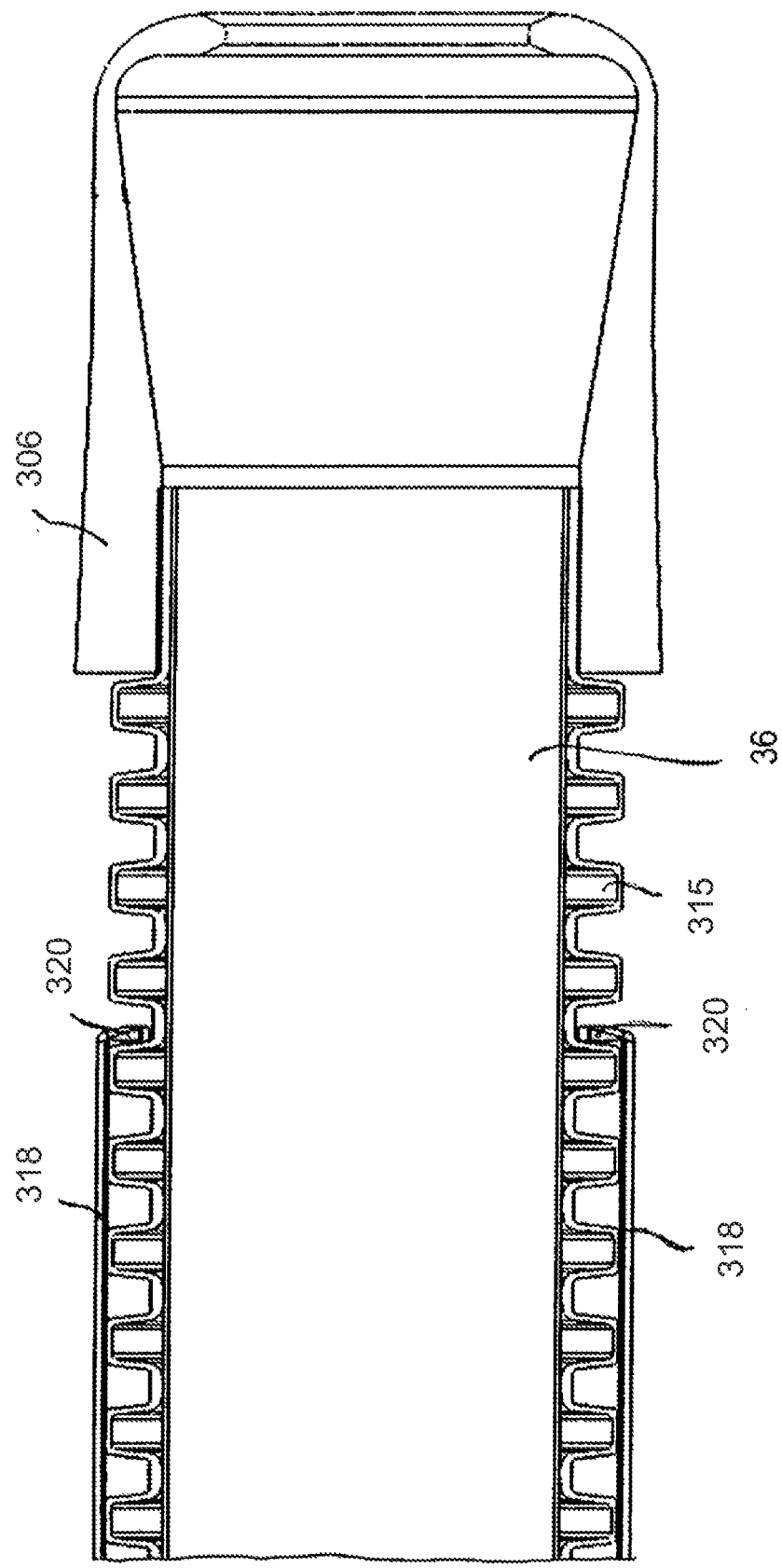

FIGS. 56 and 58 are perspective views of the entire insertion device 300 and FIG. 57 is a fragmentary side view of the proximal end and part of the working length of the insertion device, in which the outer jacket 305 has been removed. It can therefore be seen that the corrugated tube 315 extends distally beyond the strain relief retainer to the tip 306 and that vertebrae 16 are clipped between several of the corrugations. Although only five vertebrae are shown in FIGS. 56 and 58, as many as twelve or more may be provided, depending on the working length and the application for which the insertion device is intended. The vertebrae may have slits formed radially therein to aid in slipping them over the corrugated tube. The last vertebra in the distal direction is a locking ring or termination vertebra 17. Whereas FIGS. 56 and 57 show the insertion device in the unlocked condition, FIG. 58 shows it in the locked condition, which will be discussed in more detail below. FIGS. 56, 57 and 58 also show staples or tendons 318 extended axially along the outer periphery of the corrugated tube 315.

Figure 62:
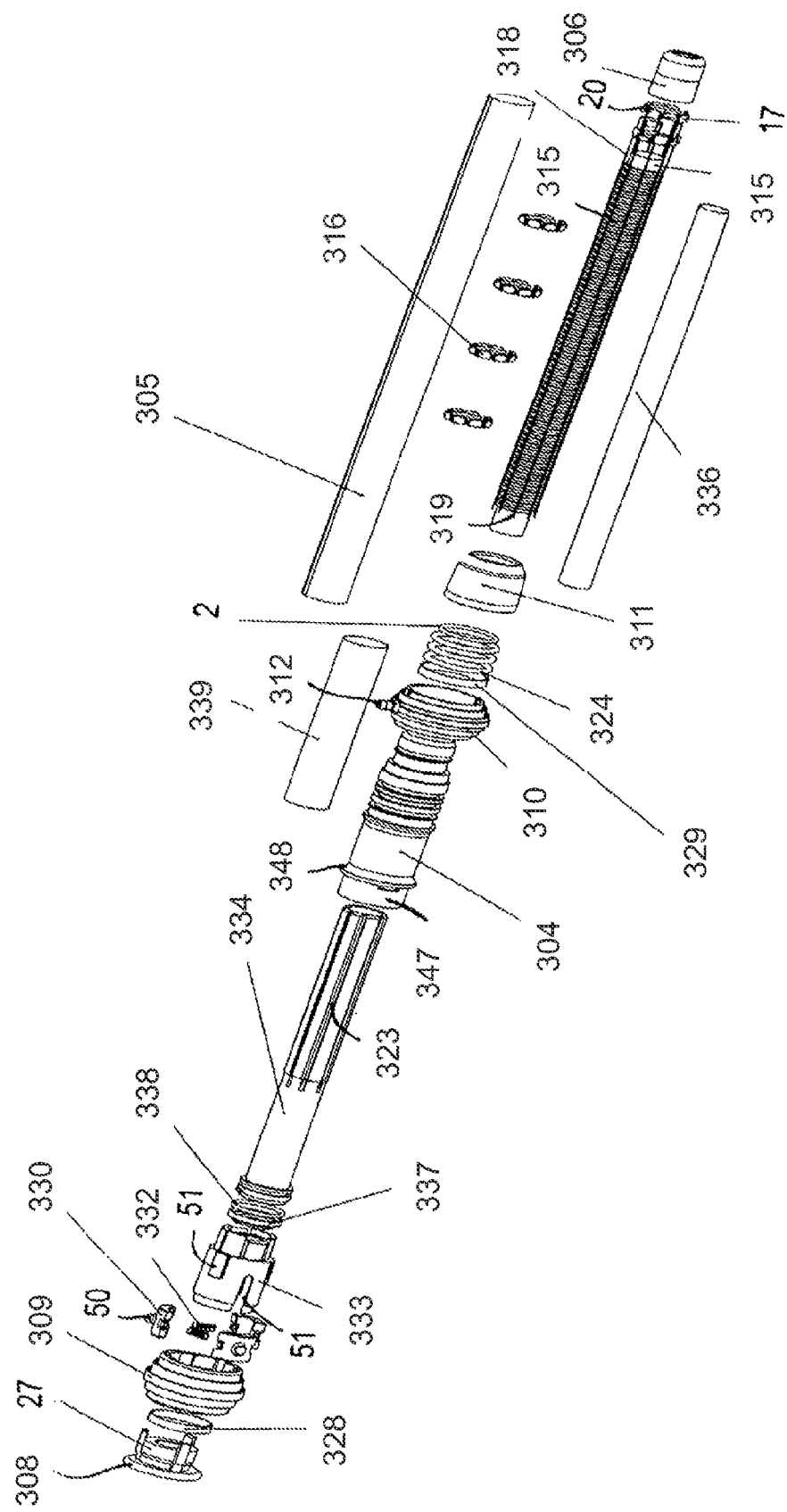
FIG. 62 is an exploded, perspective view of the insertion device of the embodiment of FIG. 51.

As is seen in the fragmentary side, perspective and longitudinal-sectional views of FIGS. 59A and 59B, 60A and 60B and 61A, 61B and 61C, the tendons or staples 318 are looped through holes or slits 322 in the vertebrae 16 and the locking ring 17. The locking rings 17 have been omitted in FIGS. 59B and 60B to show details of the tendons or staples 318. The tendons or staples 318 have ends 319 extending proximally, as shown in FIG. 62. The tendons or staples 318 may be fixedly connected to the locking ring 17, such as by adhesive, weldments or solder joints. However, FIGS. 59B and 61A, 61B and 61C show that the tendons or staples 318 have a U-shape with legs passing through the holes 322 in the vertebrae 16 and cross pieces 320 disposed just distally beyond the locking ring 17. It can be seen particularly clearly in FIG. 61A that the cross pieces 20 of the tendons or staples 318 are captured and prevented from migrating distally by two locking rings 17 between which the cross pieces H are sandwiched in a valley or trough between two peaks or crests of the corrugated tube 315.

The number and location of the tendons or staples 318 and the vertebrae 16 axially and circumferentially may be chosen in such a way as to vary the stiffness of the insertion device 300 in zones. For example, more tendons or staples 318 and/or more vertebrae 16 may be placed in one zone along the working length than in another zone. The zone with more tendons or staples and/or vertebrae will be stiffer. Additionally, some of the tendons or staples may not extend over the entire working length and some may be fixed to vertebrae along the working length, all of which also varies stiffness in zones. As the insertion device flexes, some of the tendons or staples which are not fixed to particular vertebrae slide in the holes or slits 322.

Figure 63:
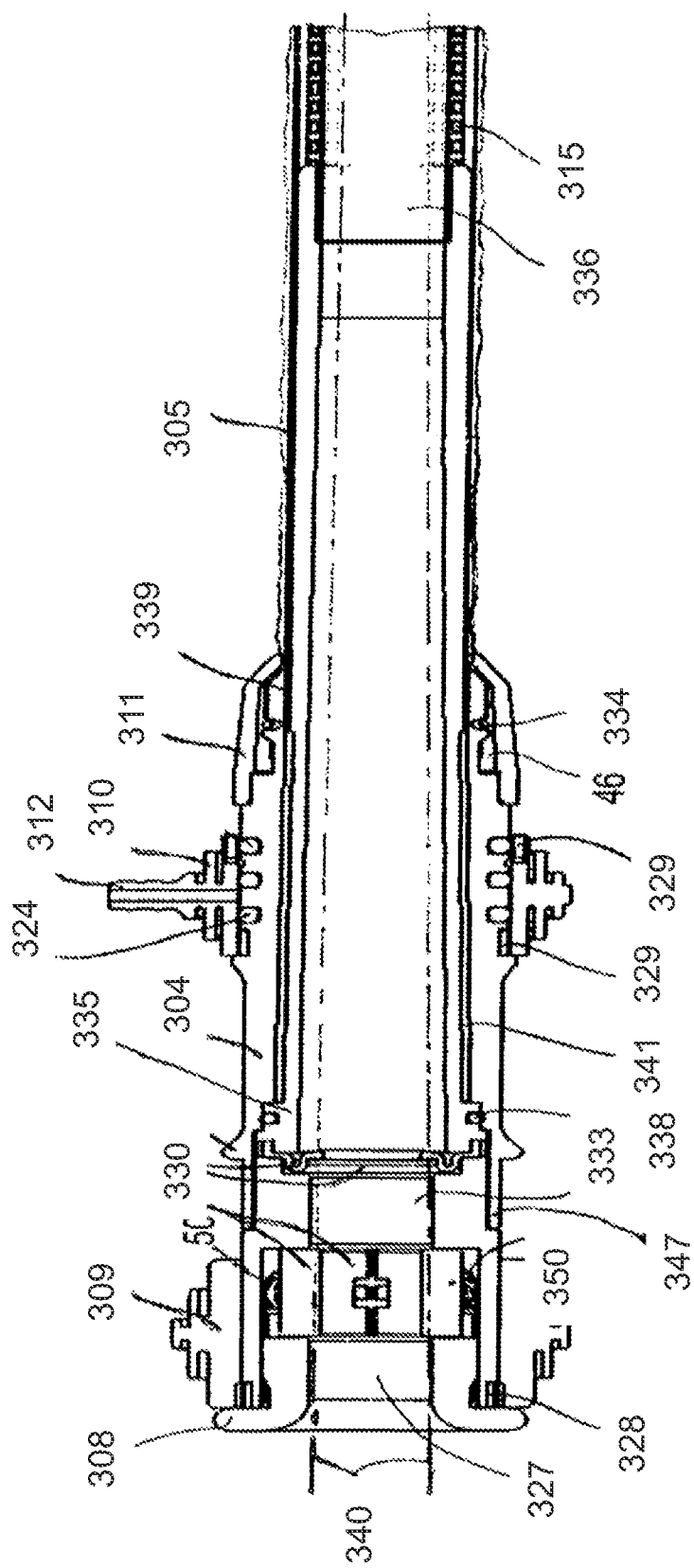
FIG. 63 is a fragmentary, longitudinal-sectional view of the proximal end and part of the working length of the insertion device of the embodiment of FIG. 51.

The exploded view of FIG. 62 and the assembled sectional view of FIG. 63 show the end cap 308 at the proximal end, which surrounds a rear bushing 316. It may be seen that a marker band 328 is disposed between the actuator or bobbin 309 and the end cap 308. A clamping plate 330, which is also disposed within the actuator or bobbin 309, has three partial-plates 331a, 331b, 331c between which three springs 332 are disposed. A body tube 333, having slots 51, is disposed distally of the clamping plate 330.

A coupler 335, having grooves 323 extended axially on the periphery thereof, carries a septum seal 337 and an O-ring 338 provides a seal between the coupler 335 and the handle 304, which is slid over the coupler 335. Other marker bands 329 are disposed between the handle 304 and the sliding valve or slider 310 and the forward stop 311 is disposed over the distal end of the handle 304. O-rings 324 provide a seal between the slider 310 and the handle 304. An O-ring 334 is disposed between the forward stop 311 and the handle 304. It may also be seen that a heat shrink tubing 339 covers the coupler 335 and an inner liner or sleeve 336 is disposed within the corrugated tube 315. Moving distally, the corrugated tube 315 carrying the vertebrae 16, the tendons or staples 318, the locking ring 17 and the distal tip 306, is shown as well.

The inner sleeve 336 provides a surface over which the instrument 340 will pass smoothly within the corrugated tube 315. The corrugated tube 315 may be formed of nylon or another suitable material. The inner sleeve 336 may be made from a sheet of polyester film, which has an adhesive coating on one side. The inner sleeve 336 is rolled around an inflatable mandrel and heated in an oven, to form a bonded seam and is sealed to an inner surface of the corrugated tube 315. The corrugations of the corrugated tube 315 have peaks and valleys, as mentioned above. As viewed from within the corrugated tube 315, the inner sleeve 336 adheres to the peaks and extends somewhat into the valleys of the corrugations as dimples. Therefore, as the insertion device bends, the inner sleeve 336 stays tight along the corrugations on the outside of the bend and crinkles at the inside of the bend. The peaks and valleys of the corrugations also need not be of equal length along the length of the corrugated tube 315. For example, 70% of the length may be peaks and 30% valleys or 80% of the length may be peaks and 20% valleys. These variations will add to the adhesion of the inner sleeve 336 to the corrugated tube 315 and reduce the formation of dimples. However, a 50/50 corrugation ratio is shown in the figures.

The outer jacket 305 may be formed of polyurethane or another suitable material which is similarly a flat sheet that is rolled and seamed. The outer jacket 305 extends to the distal tip 306 and the inner sleeve 336 terminates with the end of the corrugated tube 315, the ends of which are "cuffed" to allow attachment of components.

Figure 64:
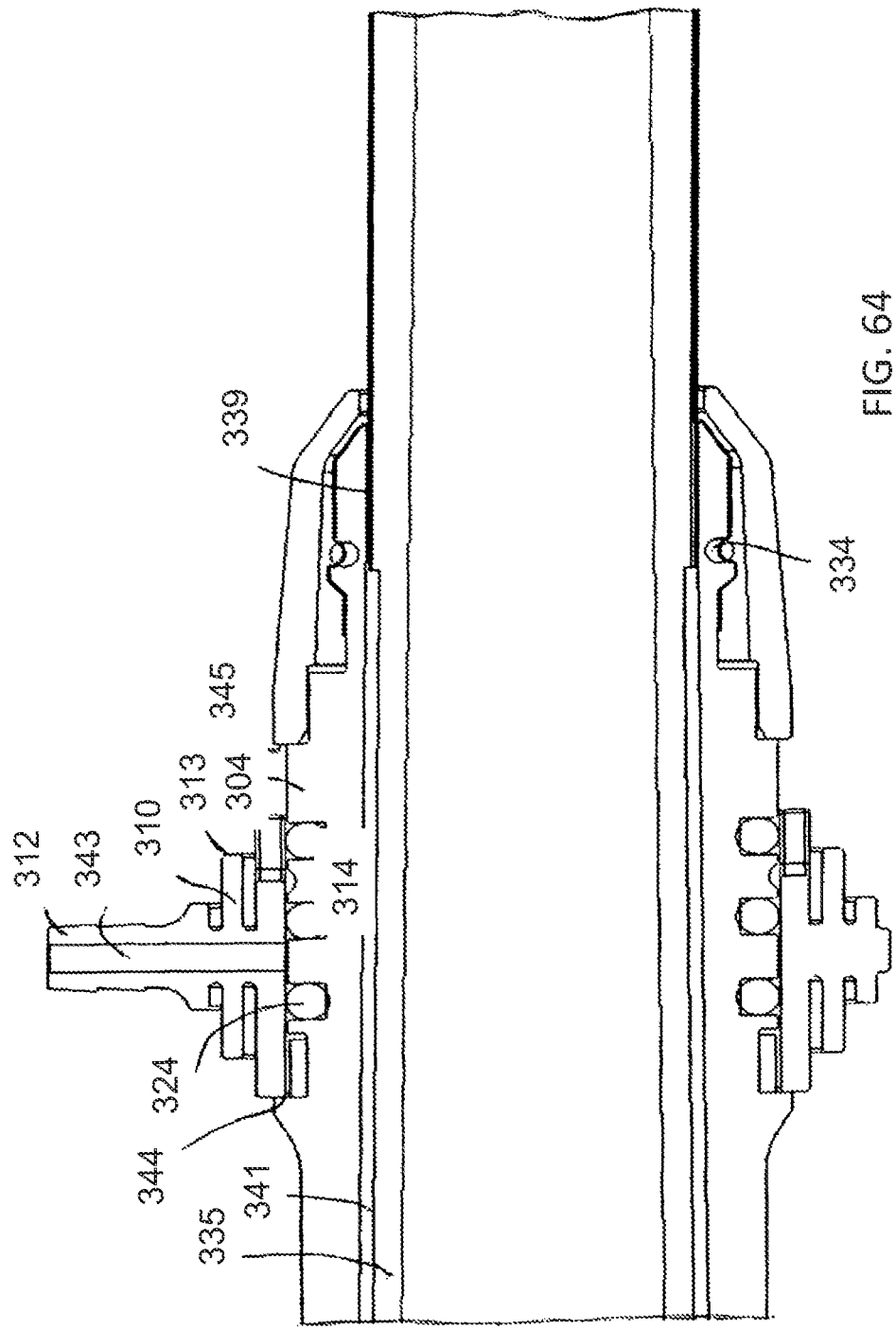
FIG. 64 is a greatly enlarged, fragmentary, side-longitudinal-sectional view of a proximal section of the insertion device of the embodiment of FIG. 51.
Figure 65:
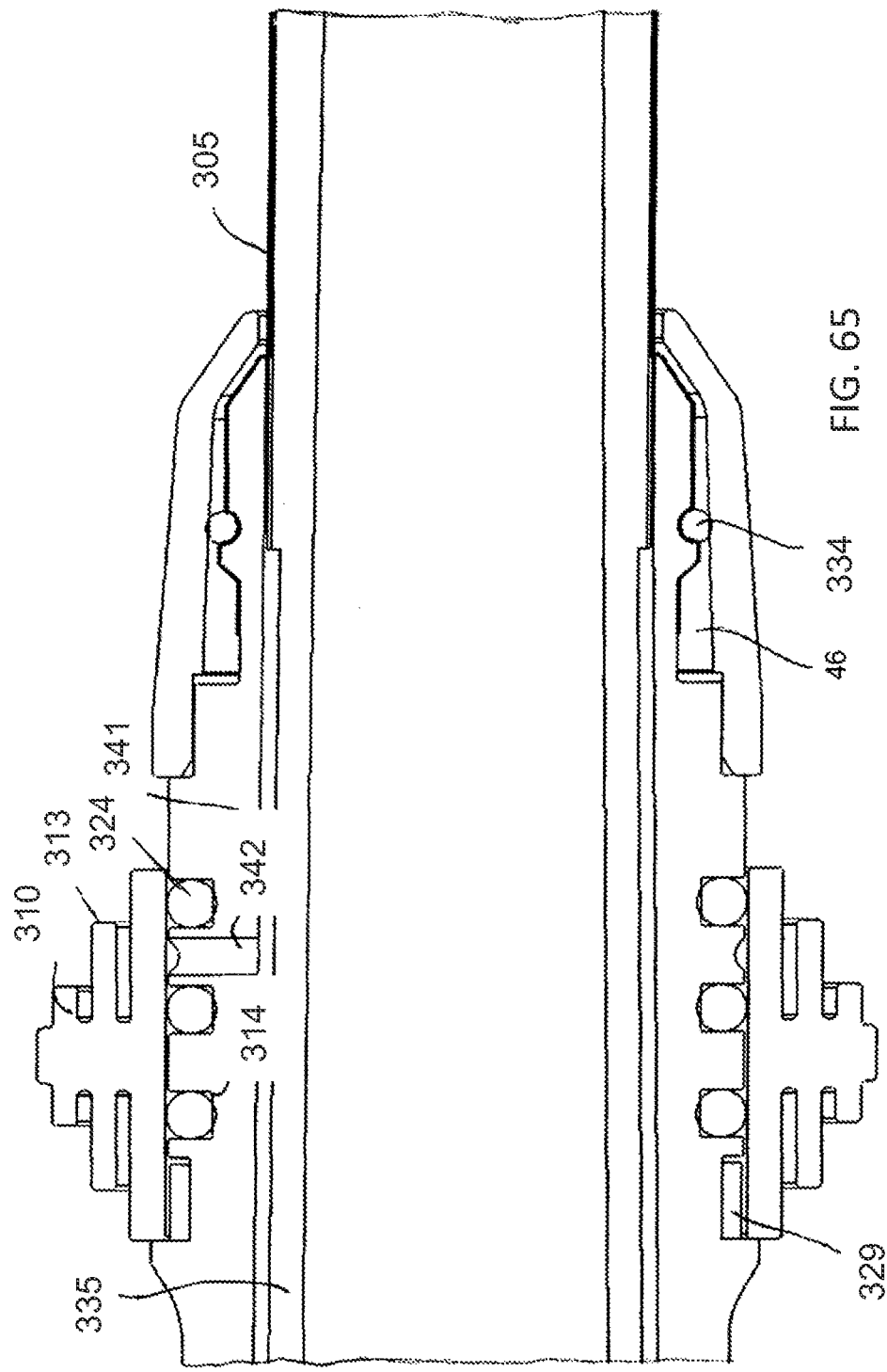
FIG. 65 is a fragmentary, top-longitudinal-sectional view of the proximal section of the insertion device of the embodiment of FIG. 51.

The sectional views of FIGS. 64 and 65 show greater detail of the construction of the slider or sliding valve 310 having the nipple 312. The slider 310, which encircles the handle 304, has a sliding so-called tire valve thumb grip 313 and is sealed thereto by the O-rings 324 which are disposed in recesses 314 in the handle 304.

It may be seen that the handle 304 and the coupler 335 define an annular vacuum plenum volume 341 therebetween which extends in longitudinal direction of the handle 304. The O-ring 2 provides a seal at the proximal end of the volume 341. A vacuum inlet/outlet hole or port 342 is formed in the body of the handle 304 and communicates with the volume 341. The sliding valve or slider 310 also has a vacuum inlet/outlet 343 for the connection or nipple 312. When the slider 310 is slid toward an annular stop 344, the vacuum inlet/outlet 343 is not in alignment with the vacuum inlet/outlet hole 342. However, when the slider 310 is slid toward an annular stop 345, the vacuum inlet/outlet 343 and the vacuum inlet/outlet hole 342 are aligned, providing communication between the connection or nipple 312 and the volume 341. Therefore, during operation, the slider 310 is slid toward the stop 345 to apply vacuum to stiffen the hollow body. The slider 310 is slid toward the stop 344 to vent the vacuum to atmospheric pressure making the hollow body flexible again.

When vacuum is applied to the volume 341 in the manner described above, the outer jacket 305 and the corrugated tube 315 approach each other with the staples or tendons 318 sandwiched and frictionally locked therebetween. Therefore, the vacuum connection or nipple 312 acts as a device for transitioning the hollow body 304, 306, 335, 305, 336, 315 between a relatively flexible condition and a relatively stiff condition through the application of a vacuum. As long as the vacuum is applied, the insertion device 300 maintains its condition, whether flexed or straight. When it is desired to resume flexibility of the insertion device 300, the vacuum is vented or replaced by air at ambient or positive pressure. This causes the corrugated tube 315 and the outer jacket 305 to release the tendons or staples 318 and the corrugated tube 315 and allows the inherent stiffness of the corrugated tube 315 to place the insertion device 300 into its normally flexible condition.

The tendons, staples or wires 318 are passive elements which are not in tension at any time. The tendons or staples float within the hollow body 304, 306, 335, 305, 336, 315 when it is in the flexible condition, except where they are fixed to the locking rings 17. The tendons or staples are frictionally locked by the corrugated tube 315 and the outer jacket or sleeve 305 when the hollow body is in the stiff condition. However, in both the relatively flexible condition and the relatively stiff condition, the tendons or staples have no active control imposed on them and are not pulled or constrained.

Figure 66:
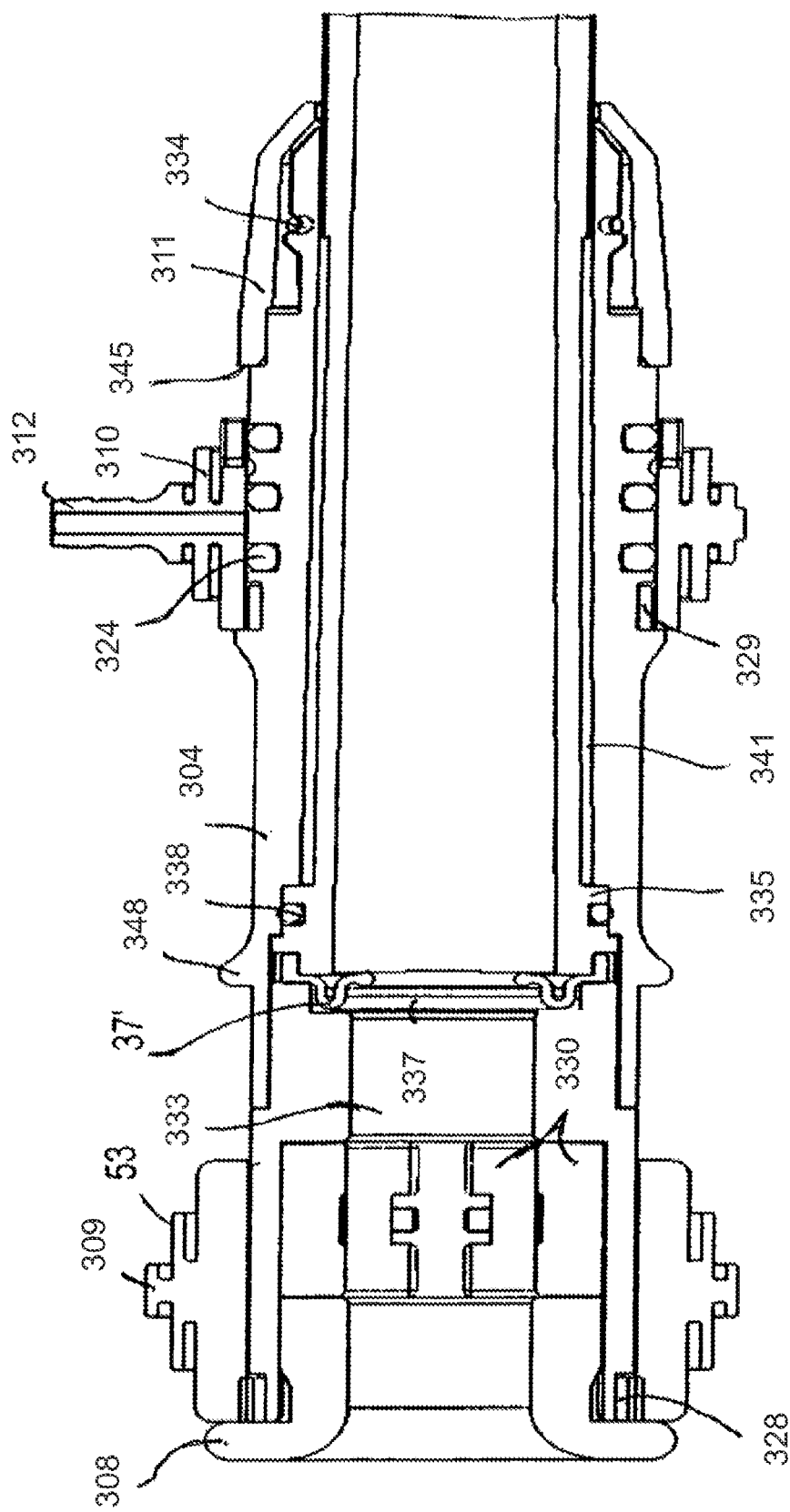
FIG. 66 is a fragmentary, side-longitudinal-sectional view of the proximal end of the insertion device of the embodiment of FIG. 51.

As mentioned above, a comparison between FIGS. 56 and 58 reveals that the actuator or bobbin 309 in FIG. 56 is adjacent the end cap 308 in a non-actuated condition, while in FIG. 58 the actuator or bobbin 309 is in an actuated condition, in which it has been moved over an extension 347 of the handle 304 and against a collar 348 of the handle 304. FIGS. 66 and 68 also show the actuator or bobbin 309 in the non-actuated condition, whereas FIG. 67 shows the actuator or bobbin in the actuated condition, but in greater detail.

As is seen in FIGS. 62-63, 66-68 and 69A, 69B and 69C, the three partial-plates or partial-shells 331a, 331b, 331c of the clamping plate 330 have detents 350 protruding therefrom. FIGS. 67, 68 and 69A, 69B and 69C in particular show that the springs 332 bias the partial-plates and therefore the detents 350 through slots 351 in the body tube 333 and into corresponding recesses 352 in the inner peripheral surface of the actuator or bobbin 309 in the non-actuated condition. When a sliding, so-called tire valve thumb grip 353 of the actuator or bobbin 309 is pushed by the operator of the device and the actuator or bobbin is slid distally toward the collar 348 of the handle 304, the detents 350 slide out of the recesses 352 against the force of the springs 332. This causes the partial-plates 331a, 331b, 331c to move toward each other radially and against the instrument 340, such as an endoscope or a colonoscope represented by a dot-dash line in FIG. 63, for holding the instrument in place. When the actuator or bobbin 309 is slid proximally, the detents 350 once again fall into the recesses 352 due to the force of the springs 332, so that the partial-plates 331a, 331b, 331c move radially outwardly and release the instrument 340. Therefore, the actuator or bobbin 309 and the clamping plate 330 form a locking and unlocking device to be activated by the operator for locking the handle 304 to and unlocking the handle 304 from the instrument 340.

Figure 67:
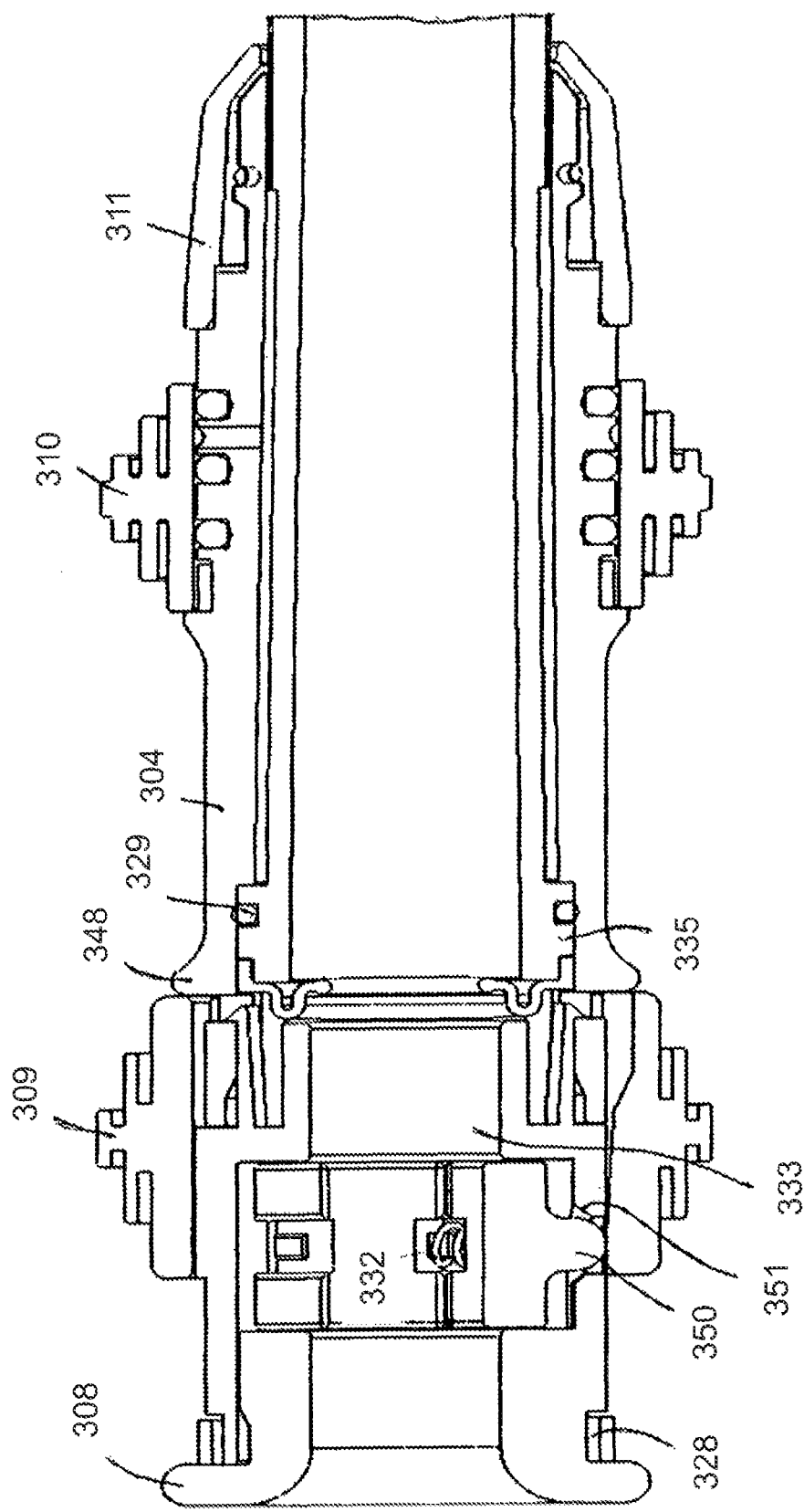
FIG. 67 is a fragmentary, top-longitudinal-sectional view of the proximal end of the insertion device of the embodiment of FIG. 51 in the actuated condition.
Figure 68:
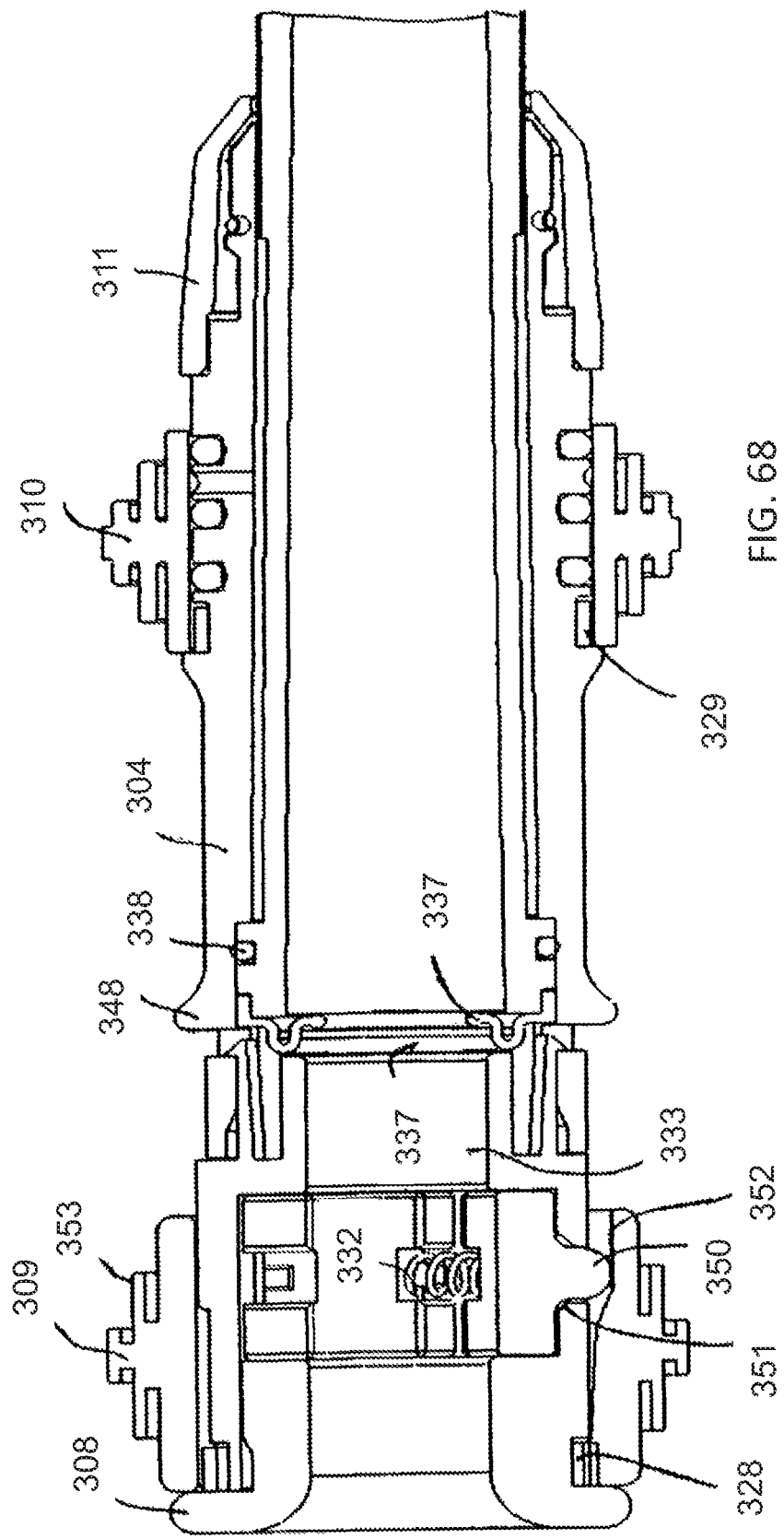
FIG. 68 is a fragmentary, top-longitudinal-sectional view of the proximal end of the insertion device similar to FIG. 67, in a non-actuated condition.

FIGS. 66, 67 and 68 also show the septum seal or valve assembly 337 in greater detail, as well as the end cap 308 which is inserted into the proximal end of the handle. End caps 308 with various sized openings may be used in dependence on the instrument being used. The instrument passes through the hollow body and emerges at the distal tip 306. It may be seen that the septum seal or septum valve assembly 337 has a diaphragm 337' resting in a recess in the coupler 335.

A comparison of FIGS. 69A, 69B, 69C and 69D also shows that in FIG. 69A merely the handle 304 with the extension 347 and the collar 348 as well as the partial-plates 331a, 331b, 331c are shown, while the body tube 333 has been slid over the partial-plates in FIG. 69B, the end cap 308 has been added at the proximal end in FIG. 69C and the actuator or bobbin 309 has been added distally of the end cap in FIG. 69D.

What is claimed is:

1. A torque-transmitting, variably-flexible device, comprising:
 a hollow body having:
  a proximal end and a distal end; and
  a given length;
 a torque-transmitting element that extends substantially entirely over the given length of the hollow body and transmits torque from the proximal end towards the distal end of the hollow body;
 a steering element that steers the distal end of the hollow body, the steering element being comprised of steering tendons disposed within the hollow body, wherein at least some of the steering tendons are individually adjustable in length for steering the distal end of the hollow body; and
 stiffening tendons disposed within the hollow body to selectively maintain the hollow body in a relatively stiff condition, wherein the stiffening tendons are unassociated with the steering element of the device.

2. The device according to claim 1, wherein:
 the proximal end of the hollow body has an entrance for receiving an instrument; and
 the distal end of the hollow body has a tip for protrusion of the instrument.

3. The device according to claim 1, wherein the torque-transmitting element is a torque braid.

4. The device according to claim 1, further comprising vertebrae disposed within the hollow body for guiding the steering tendons.

5. The device according to claim 4, wherein some of the vertebrae have channels formed therein permitting movement of some of the steering tendons.

6. The device according to claim 1, further comprising a transitioning device selectively transitioning the hollow body between a relatively flexible condition and the relatively stiff condition.

7. The device according to claim 6, further comprising a coil disposed within the hollow body, the coil tending to maintain the hollow body with an approximately round cross section and in a straight condition when in the relatively flexible condition.

8. The device according to claim 6, wherein the transitioning device is a vacuum-activated device applying suction to the hollow body to place the hollow body in the relatively stiff condition.

9. The device according to claim 8, wherein suction applied by the vacuum-activated device frictionally locks the stiffening tendons in place to selectively maintain the hollow body in the relatively stiff condition.

10. The device according to claim 9, wherein the stiffening tendons are not under tension in both the relatively flexible and relatively stiff conditions.

11. The device according to claim 9, wherein the stiffening tendons vary in number along the hollow body for providing zones of varying stiffness.

12. The device according to claim 11, wherein the number of stiffening tendons is greater toward the distal end than toward the proximal end for increasing stiffness at the distal end.

13. The device according to claim 9, wherein the hollow body has an outer jacket and an inner sleeve defining a space therebetween, the stiffening tendons are at least partly disposed in the space, and the vacuum-activated device applies suction to the space for frictionally locking the stiffening tendons in place.

14. The device according to claim 13, wherein the vacuum-activated device is a vacuum connection communicating with the space.

15. The device according to claim 14, wherein the hollow body has a handle at the proximal end, the handle has an outer handle and an inner handle defining a vacuum plenum volume therebetween communicating with the space, and the handle has a vacuum port communicating with the vacuum plenum volume.

\* \* \* \* \*